(12) United States Patent
Bacich et al.

(10) Patent No.: US 12,370,078 B2
(45) Date of Patent: Jul. 29, 2025

(54) APPARATUS AND METHOD FOR DELIVERY AND/OR REMOVAL OF OCCLUSIONS IN THE BODY

(71) Applicant: NEXT Life Sciences, Inc., San Luis Obispo, CA (US)

(72) Inventors: Steven R. Bacich, Half Moon Bay, CA (US); Matthew Thomas Yurek, San Diego, CA (US); Michael Hartsfield, Poway, CA (US); Jack Greelis, Carlsbad, CA (US); Luke Fox, San Luis Obispo, CA (US)

(73) Assignee: NEXT Life Sciences, Inc., San Luis Obispo, CA (US)

( * ) Notice: Subject to any disclaimer, the term of this patent is extended or adjusted under 35 U.S.C. 154(b) by 0 days.

(21) Appl. No.: 18/792,215

(22) Filed: Aug. 1, 2024

(65) Prior Publication Data

US 2025/0134701 A1    May 1, 2025

Related U.S. Application Data

(60) Provisional application No. 63/593,750, filed on Oct. 27, 2023.

(51) Int. Cl.
*A61F 6/22* (2006.01)
(52) U.S. Cl.
CPC .................... *A61F 6/225* (2013.01)
(58) Field of Classification Search
CPC .......... A61F 6/225; A61F 5/003; A61F 6/206; A61F 6/06; A61F 6/02; A61F 6/20; A61F 6/146; A61B 17/12022; A61B 17/12027; A61B 17/12045; A61B 17/12099; A61B 17/12131; A61B 2017/12127; A61B 2017/22051; A61B 17/12109; A61B 2017/22001; A61M 25/10; A61M 29/00; A61M 25/104; A61L 27/52; A61L 2430/36

See application file for complete search history.

(56) References Cited

U.S. PATENT DOCUMENTS

| 4,509,504 A | 4/1985 | Brundin |
| 6,030,397 A | 2/2000 | Monetti et al. |
| 8,784,413 B2 | 7/2014 | Govari et al. |

(Continued)

FOREIGN PATENT DOCUMENTS

GB            2517962 A    *  3/2015   ............. A61B 1/042

*Primary Examiner* — Ophelia A Hawthorne
(74) *Attorney, Agent, or Firm* — Levine Bagade Han LLP

(57) ABSTRACT

Delivery systems for providing occlusive hydrogels in a tube lumen or void space within the body including but not limited to a reproductive tract such as the vas deferens or fallopian tubes for contraception are described. The delivery systems contain mechanisms that confirm proper placement of the system in the bodily lumen prior to the delivery of the occlusive material. The systems also can contain a confirmatory mechanism that demonstrates the blockage or occlusion in the bodily lumen has been achieved following the deposition of the occlusive material. Another aspect of this application is to provide a removal system that delivers dissolving material, agitates, aspirates, and confirms the patency of the bodily lumen following the removal of the occlusive material if so desired by the patient for the return to fertility.

20 Claims, 55 Drawing Sheets

(56) References Cited

U.S. PATENT DOCUMENTS

| | | |
|---|---|---|
| 9,861,515 B2 | 1/2018 | DePinto et al. |
| 9,949,664 B2 | 4/2018 | Ludwin et al. |
| 10,155,063 B2 | 12/2018 | Herr et al. |
| 10,456,292 B2 | 10/2019 | DePinto et al. |
| 10,751,124 B2 | 8/2020 | Eisenfrats et al. |
| 10,791,950 B2 | 10/2020 | Mest |
| 11,779,372 B2 | 10/2023 | Lee-Sepsick et al. |
| 11,839,460 B2 | 12/2023 | Palushi et al. |
| 11,903,570 B2 | 2/2024 | Cummins et al. |
| 11,904,068 B2 | 2/2024 | Herr et al. |
| 11,937,910 B2 | 3/2024 | Olson |
| 2003/0109837 A1 | 6/2003 | McBride-Sakal |
| 2005/0192616 A1 | 9/2005 | Callister et al. |
| 2012/0253120 A1 | 10/2012 | Callister et al. |
| 2017/0231499 A1 | 8/2017 | Gimzewski et al. |
| 2018/0185096 A1 | 7/2018 | Eisenfrats et al. |
| 2020/0237388 A1 | 7/2020 | Eisenfrats et al. |
| 2022/0155341 A1 | 5/2022 | Song et al. |
| 2022/0168461 A1 | 6/2022 | Herr et al. |
| 2023/0346583 A1 | 11/2023 | Grover et al. |

\* cited by examiner

APPARATUS AND METHOD FOR DELIVERY AND/OR REMOVAL OF OCCLUSIONS IN THE BODY

CROSS-REFERENCE TO RELATED APPLICATIONS

This application claims the benefit of priority to U.S. Provisional Application No. 63/593,750 filed Oct. 27, 2023, which is incorporated herein by reference in its entirety for all purposes.

BACKGROUND

This application has particular utility for systems providing the delivery of occlusive devices for contraception in the vas deferens of the male reproductive system or the fallopian tubes of the female reproductive tract for contraception. The systems and methods described herein can be used for occlusive devices in all bodily lumens. Hydrogels can perform as an occlusive device when injected into bodily lumens since they can conform to the intraluminal environment, have known biocompatibility, and in some cases, form a gel that is resilient since the body is dynamic, and durable to maintain its occlusive property. The hydrogels described herein are particularly suited for contraception since after occlusion, a reversal procedure can be performed. Reversibility of an occlusive device or hydrogel results in the return of patency of the vas deferens and fallopian tubes. By allowing the passage of sperm in the vas deferens, or sperm and eggs in fallopian tubes, will allow for the return to fertility.

The injection of occlusive devices and hydrogels in a reproductive tract is typically done by a physician using a hypodermic needle system that penetrates the wall of the bodily lumen. In practice, the distal end of the needle opening could inadvertently miss the lumen and result in the delivery of the hydrogel in an unintended location. In this situation the hydrogel will be ejected into an interstitial space or some cases, miss the bodily lumen altogether.

Once entry into the bodily lumen is achieved, the needle can remain in the lumen throughout the remainder of the procedure. For patients that are awake without general anesthesia, any unintentional movement by the patient or physician can alter the positioning of the needle system. The sharp distal end of the needle can inadvertently protrude into unintended locations in particular outside of the vas deferens. The sharp end of the needle can perforate the vas deferens or penetrate into the posterior wall of the vas deferens, after the initial penetration through the anterior wall during the injection process. Additionally, the sharp distal end of the needle could embed within the wall of the vas deferens in an interstitial location. This is particularly true for the vas deferens with muscular walls and surrounding fascia but with internal lumens that represent primarily potential spaces with soft mucosal lining or epithelium within the internal potential space. For the delivery system, the continued presence of a sharp needle within the bodily lumen increases the risk that the injection of the hydrogel could occur within an unintended location of the bodily lumen.

SUMMARY

A method of confirming intraluminal access of a lumen in a body is disclosed. The method can include inserting a sheath into the body, advancing a probe relative to the sheath by an advancing distance into the lumen, and/or confirming the sheath has access to the lumen if the advancing distance is greater than or equal to a threshold distance.

A device is disclosed that can have a sheath and a probe. The probe can be advanceable from a retracted configuration to an advanced configuration relative to the sheath. When the probe is in the retracted configuration, a first distance can be between the probe and the sheath. When the probe is in the advanced configuration, a second distance greater than the first distance can be between the probe and the sheath. The first distance can be less than a threshold distance. When the second distance is greater than or equal to the threshold distance, the advanced configuration of the probe can be an indicator to a user that the device has access to a target site.

A method of removing a first material from a body lumen is disclosed. The method can include inserting a sheath into the body lumen, advancing a probe into the body lumen relative to the sheath, agitating the first material in the body lumen with the probe, irrigating a second material into the body lumen, and/or removing the first material from the body lumen.

A method of removing a first material from a body lumen is disclosed. The method can include inserting a sheath into the body lumen, inserting a probe into the body lumen, agitating the first material in the body lumen with the probe, irrigating a second material into the body lumen, and/or aspirating the first material and the second material from the body lumen.

A method of removing a first material, a second material, and/or a third material from a body lumen is disclosed. The method can include inserting a sheath into the body lumen, inserting a probe into the body lumen, agitating the first material in the body lumen with the probe, irrigating the second material into the body lumen, and/or removing the first material, the second material, and/or the third material from the body lumen.

A device is disclosed that can have a sheath, a probe, a first material, and/or a first opening. The device can have a first configuration and a second configuration. More of the first material can be distal the first opening when the device is in the second configuration than when the device is in the first configuration. The first material can be closer to a second material when the device is in the second configuration than when the device is in the first configuration. The probe can have a retracted configuration and an advanced configuration. More of the probe can be distal the first opening when the probe is in the advanced configuration than when the probe is in the retracted configuration. When the probe is in the advanced configuration, the probe can be movable from a first position to a second position. When the device is in the second configuration and the probe is in the first position, the probe can be in contact with the first material. When the device is in the second configuration and the probe is in the second position, the probe can be in contact with the first material or a gap can be between the probe and the first material. A distal terminal end of the probe can be the same distance or a different distance from the first opening when the probe is in the second position than when the probe is in the first position.

Systems disclosed herein can contain mechanisms that confirm proper placement of the system in the bodily lumen prior to the delivery of the occlusive material would be advantageous and facilitate better clinical outcomes. Systems can have one or more confirmatory mechanisms that demonstrate that the blockage or occlusion in the bodily lumen has been achieved following the deposition of the occlusive material.

A removal system is disclosed that can remove the luminal occlusion in a minimally invasive manner and confirms the patency of the bodily lumen following the removal of the occlusive material itself. In both the male or female applications, the availability of a long-lasting, non-hormonal, reversible contraception that can be delivered or removed in a minimally invasive manner meets an important unmet clinical need. The systems described herein can be configured for both ease of use by the healthcare provider and are designed to provide a confirmation of luminal placement and occlusion at the time of placement. At the time of removal, the systems can confirm intraluminal placement and return to patency once the hydrogel occlusion has been removed.

The system can minimally invasively penetrate bodily lumens and simplify the number of user steps in the procedure.

Systems for the delivery and removal of occlusive materials are described herein. The systems can have hypodermic needles and syringe systems in which occlusive agents such as hydrogels are injected into the bodily lumen. Syringe systems can contain handles for greater mechanical action for injecting viscous materials or two-part systems.

Systems for the delivery and removal of occlusive materials can also be provided without a hypodermic needle, or part of a hypodermic needle. The delivery and removal systems can be inserted using a catheter once a blunt dissection of the anterior wall of the vas deferens or fallopian tube is performed.

The systems described herein can be applied percutaneously and subcutaneously without exposing and isolating the vas deferens.

For the descriptions supplied herein, the vas deferens and fallopian tubes can be used or applied interchangeably for the delivery and removal of the occlusive hydrogel.

The use of a cylindrically shaped needle or hypodermic needle for insertion into the bodily lumen is disclosed herein. Hypodermic needles can have hollow, cylindrical tubing with a sharpened bevel at the distal end. These needles can be made from stainless steel with varying degrees of flex depending upon the gauge of needle. The dimensional tubing diameter and wall thickness define the needle gauge. Higher gauge needles are defined by smaller outer diameters. For the injection of hydrogels into the vas deferens for male contraception, the needle gauges range from 21 G to 25 G with a 23 gauge as a nominal size insertion needle.

For male contraception, the physician can first identify and isolate the vas deferens. This can be accomplished by manually palpating the scrotum until the muscular wall of the vas deferens determined. The location and guidance to the vas deferens can be facilitated by imaging systems such as ultrasonography, computed tomography, and magnetic resonance (MR) imaging to assist in identifying the vas deferens. A ring clamp can be used to retain the vas deferens underneath the scrotal skin and separate from the spermatic cord. In the 'no scalpel' technique, sharpened curved dissecting forceps are used to provide blunt dissection of the scrotal skin with the goal of reaching the retained vas deferens and minimizing bleeding. The curved pinchers are also used for additional blunt dissection by removing the surrounding fascia from the vas deferens until the appropriate length of vas deferens is elevated outside the scrotum for access for the remainder of the vasectomy procedure. The curved pinchers are also used for additional blunt dissection on the anterior wall of the vas deferens to allow for access to the lumen of the vas deferens. Following the ligation or occlusion of the vas deferens, the exposed and isolated portion of the vas deferens is then tucked back into the scrotum and the procedure is repeated on the contralateral side of the scrotum for the other vas deferens. Using the curved pinchers to apply blunt dissection of the anterior wall of the vas deferens can also minimize the amount of vas deferens that needs to be exposed and isolated. Alternatively, the application can be performed percutaneously. Once the vas deferens procedure has been completed and the absence of bleeding is confirmed, a simple bandage can be applied to the scrotal entry sites.

The following are descriptions of insertion of the system into the bodily lumen.

For the delivery of hydrogels in the vas deferens for male contraception, the use of hydrogels offers the opportunity of percutaneous delivery through the scrotal skin, thereby minimizing the level of invasiveness for the procedure. By minimizing surgical injury or trauma, patient recovery and comfort is enhanced.

Variations of delivery instruments are described herein. The delivery instruments can place occlusive devices within the lumen of a reproductive tract and/or deliver removal agents for the return to patency of the reproductive tract. The intended target for the delivery instrument can be the lumen of the reproductive tract. Unintended placement of the occlusive device or removal agent can render the procedure unsuccessful.

For the delivery of hydrogels in the fallopian tube for female contraception, the use of transcervical approach with a catheter, or a hysteroscope and catheter, offers a non-incisional insertion into the proximal portion of the fallopian tube. Alternatively, a hydrogel can be delivered by use of an ultrasonically guided transvaginal needle, or with other imaging modalities such as computed tomography and magnetic resonance (MR) imaging, through the wall of the vagina and directly into the fallopian tube. Another approach would be a laparoscopic entry into the fallopian tube.

When performing a procedure on the vas deferens, ring clamps can be used for lifting or holding the vas deferens tissue. A half-pipe or side-support system can be used to stabilize and maintain the vas deferens in a linearly straight form. The half-pipe or side-support system is configured to stabilize the vas deferens tissue for injection by a straight penetrating tool such as a needle, or a half needle described below. Alternatively, for anatomical variations, an inguinal or laparoscopic approach can be used to access the vas deferens.

Holding and isolating the vas deferens with vacuum pressure with suction holder attached to the anterior wall of the vas deferens is disclosed herein.

A ring clamp for isolating and holding the vas deferens can have an angle miter tool for guiding the specific angle of entry for an access device and catheter.

The system can provide intraluminal insertion into a bodily lumen with a minimal profile and minimizing user steps. The system can allow for the passage of multiple instrumentation within a central lumen of delivery or removal system without the need for back exchanges or removal of needles or probes from the access system. As an example, when using a hypodermic needle for insertion and passage of a guidewire, once entry into the bodily lumen is established, the hypodermic needle needs to be threaded back in a retrograde direction so that the needle can be removed from the guidewire. Once the hypodermic needle is removed from the guidewire, other instrumentation or catheters can be deployed over the guidewire. Eliminating the need for a back exchange can reduce the number of user steps and any instability caused by these additional movements and actions.

A split needle insertion system with two-hemispherical sections is described. The hemispherical sections can be split apart in a radial direction from the co-linear central axis. As the needle is split apart, other instrumentation can be passed through the central axis without requiring a back exchange.

The hemispherical sections can be rotated along their central axis to form an opening in the insertion needle. In either configuration, the portions of the split do not have to be equal in size, only cylindrical at insertion and a second configuration with an opening. Multiple sections that split or rotate apart greater than two are possible.

A half-needle insertion system for insertion into a bodily lumen is described. The half needle can reduce the profile at entry and shield or contain a probe within the half needle section. This can be done with the half needle cut at the equator of its cylindrical shape, the half needle above the equator, or the half needle below the equator. The half needle can have a curved shape, for example, to allow for more oblique angles of insertion or entry into a bodily lumen.

The system can have a deflecting lancet or trocar for probe insertion. The lancet or trocar can be spring loaded for entry.

The system can enter the vas deferens with a hemispherical transection of the vas deferens tube to physically expose the lumen.

The system can enter the vas deferens following a blunt dissection of the anterior wall for access to the lumen of the vas deferens.

For the insertion of occlusive devices into a bodily lumen, positive confirmation of intraluminal access would be a significant improvement to the success of the procedure. Intraluminal placement into a bodily lumen can be confirmed. A spring-loaded retractable lancet ensures a specific depth of penetration into a bodily lumen. The system can have a spring-loaded probe that can traverse into the lumen of the vessel as a confirmatory method of insertion.

A confirmatory method can utilize the injection of media for hydro-distension before and after probe insertion. The injection of media as a confirmation step can be quantified by a specific translation of a probe into the vas deferens. The probe has a flexible tip and will coil or back out if placed outside the true lumen of the vas deferens. The translation of the probe or guidewire for a predetermined distance can denote or signal true or confirmed lumen entry. This translation distance, referred to as distance "L" can be 5 cm in length of probe travel from the end of the access sheath to the distal tip of the probe. A range of 1 cm to 15 cm is also possible for the "L" distance.

The probe can be hydrophilic coated for added lubricity thereby reducing friction. The probe can be coated with other lubricity agents like silicone oil or MDX solutions. The distal end of the probe can be configured straight in its natural state or pre-formed in a "J" shape.

The continuation of the procedure cannot occur unless the translation distance of the probe has been accomplished. The delivery or removal system handle contains a lock out latch that can only be released once the probe reaches the prescribed translation distance. The remaining steps that could not be performed without satisfactorily completing the "L" distance with the probe include a) advancement of the access sheath over the probe, b) the injection of media into the bodily lumen, and c) the injection of the occlusive device. The requirement that the probe traversed the "L" distance provides a quantifiable threshold for intraluminal confirmation prior to further intervention in the bodily lumen. The lock out latch mechanism prevents the end user from defeating the "L" distance threshold.

The injection of media for hydro-distension before and after probe insertion can be used to confirm intraluminal placement. The amount of force required to inject the media can be quantified as a determinant for true lumen placement. Flow rate and volume can be measured with or without a force measurement.

The injection of media for hydro-distension before and after probe insertion can be visualized by using ultrasound or radiographic means.

The injection of media for hydro-distension before and after probe insertion can also be confirmed with lavage that flows through the vas deferens and out through the urethra.

The step of injecting media into the vas deferens or bodily lumen can be used for clearing the bodily lumen of material and preparing for subsequent hydrogel insertion.

After the insertion of the occlusive device or hydrogel, the injection of media can assist in the gelation or curing of the hydrogel.

Once the occlusive device or hydrogel is placed within the bodily lumen, probe insertion with flexible tip can be used for confirming occlusion of the lumen.

Traversing the probe the required "L" distance can use a spring mechanism for the translation of probe. The spring mechanism applies a consistent advancement force without the variability of the end user. Essentially higher advancement forces by the end user on a probe for confirmation could not be done with a spring mechanism for probe advancement.

The proximal end of the probe can be coupled to a force measurement system to display the amount of force required to traverse "L" distance for intraluminal placement confirmation.

The sharp distal end of the insertion system can be removed before further manipulation in the bodily lumen.

After confirmation of intraluminal placement, the needle can be split in two-halves in a radial direction. Once split, the two-halves can be retracted, and the access sheath can be passed over the probe without requiring a back exchange.

The two-halves of the split needle can be configured in which one half rotates about the central axis of the cylinder thereby creating an opening in the needle configuration. The remaining section can be retracted and the access sheath advanced over the probe without requiring a back exchange.

A half needle design can minimize the insertion profile and provides a shape that can be both retracted and minimized for further instrumentation in the central lumen of the access system. Once confirmation of intraluminal placement is achieved with the probe, the half needle can be retracted and placed into a location of the handle housing without needing a back exchange or further manipulation by the end user.

The bodily lumen can be prepared for hydrogel delivery. The injection of media such as normal saline, phosphate buffered saline, Ringer's lactate, or other media can be used for clearing the bodily lumen of remnant materials and fluids. The injection can prepare the bodily lumen for hydrogel insertion by opening the luminal cavity, wetting the intraluminal surfaces, supplying further lubricity, mechanical distension in the potential space of the lumen, supply or alter the internal pH, supply additional proteins, electrolytes, surfactants, wetting agents, or fluids that improve the bioadhesive properties of the hydrogels and make the intraluminal environment more uniform for widespread clinical use and hydrogel implantation. The media can also be a gas such as $CO2$ or other gases that are acceptable for use in the body.

Gas media can also be applied to dry or reduce the amount of fluids in the intraluminal environment of the vas deferens.

The injection of media can also assist in the gelation of the hydrogel after delivery sheath insertion. The media in the intraluminal environment can accelerate the cure rate of the hydrogel in vivo.

The hydrogel can be delivered. The access and delivery system can be configured with a hydrogel cartridge with plunger. The hydrogel cartridge can also have a flexible tip plunger to allow for the distal tip of the plunger to exit the delivery sheath.

For injection of the hydrogel into the bodily lumen, antegrade delivery is defined as inserting the delivery sheath and injecting the hydrogel forward into the bodily lumen. Retrograde delivery is defined by a retraction of the delivery sheath during the injection process. The delivery sheath can be used for retrograde delivery facilitated by simultaneous retraction of the delivery sheath during injection.

Occlusion of the bodily lumen can be confirmed after hydrogel delivery and removal of the system from the bodily lumen. The injection of media can be used for confirming occlusion using force, pressure, flow rate, or volume measurement to confirm occlusion.

The injection of media can be employed immediately after the injection of the hydrogel for creating space inside the bodily lumen to prevent excess material or tail of the hydrogel to exit the bodily lumen.

A method for preventing the tail of the hydrogel from exiting the bodily lumen can utilize simultaneous rotation of delivery sheath during retraction to prevent the tail of hydrogel from exiting. The simultaneous rotation can be supplied by a motor applying rotary forces to the delivery sheath.

Once an occlusive device or hydrogel is inserted into a bodily lumen, future identification of the delivery site of the occlusive hydrogel in the bodily lumen may prove to be difficult. The insertion site may heal with minimal scarring or trauma at the site of entry. For the vas deferens or fallopian tube, a tag or identifier can be applied for future identification of the entry site. The entry site can be tagged with a visual tattoo on the external surface of the vas deferens or fallopian tube.

The site of insertion into the vas deferens or fallopian tube can be tagged with an external clip that is also visible via ultrasound or radiographic imaging, for example for future identification of the delivery of the occlusive hydrogel in the bodily lumen. The clip may or may not occlude the vas deferens or fallopian tube, and can mark the site of insertion that can be identified in the future.

The site of insertion into the vas deferens or fallopian tube can be tagged with a circumferential band around the vas deferens or fallopian tube, for example to permanently identify the site of insertion for future identification of the delivery of the occlusive hydrogel in the bodily lumen. The circumferential band can be slightly elastomeric and is not restrictive to occlude the bodily lumen and does not create tissue necrosis or a chronic inflammatory event.

The hydrogel occlusion can be removed from a bodily lumen. At the time of removal of the occlusive hydrogel (or reversal, both terms apply), the mode of isolating the vas deferens or cannulating the fallopian tube can be the same.

At the time of removal, insertion can occur into the bodily lumen. At the time of removal, a more proximal entry site may be required for the "L" distance requirement of the probe to be satisfied. The "L" distance requirement can be reduced at the time of removal. As an example, the "L" distance at the time of removal can be 1 cm, 2 cm or 3 cm, as opposed to a larger "L" distance requirement at the time of delivery or injection.

At the time of removal, the embodiments for confirmation of intraluminal placement, and the embodiments for placement of intraluminal sheath and removal of the sharp implement, have been described. In this instance, the intraluminal sheath is termed the removal sheath and can be configured the same as the delivery sheath.

The removal sheath can have multiple lumens for both irrigation and aspiration. The probe for intraluminal confirmation can be housed or applied in either the irrigation or aspiration lumen.

At the time of removal, media can be delivered to confirm occlusion of the bodily lumen with the hydrogel using a force, pressure, flow rate, or volume measurement system to quantify occlusion.

The probe can be advanced to confirm occlusion in the bodily lumen by force measurements experienced during the advancement of the probe by encountering the intraluminal occlusion. The prevention of further translation of the probe in the lumen can be used to confirm occlusion in the bodily lumen.

The process of removal of the hydrogel can include instillation of a dissolving media into the bodily lumen with concurrent irrigation and aspiration. Dissolving media can be sodium bicarbonate solution composed of 8.4% sodium bicarbonate, or a range of 2% to 10%, or a larger range of 1% to 15% of sodium bicarbonate to dissolving media such as water. The concentration of sodium bicarbonate can range from 4% to 10%, or a larger range of 1% to 15%. The instillation can be performed with a two-lumen, co-linear concentric sheath system.

The two-lumen sheath system can have a central lumen for probe passage and irrigation with an eccentric lumen for aspiration that is proximal to the distal end of the irrigation lumen.

The sodium bicarbonate can be administered at body temperature (37° C.) or a higher temperature than body temperature to accelerate the reaction to the hydrogel. The elevated temperature can range from 37.1° C. to 44° C., and is controlled to not create a localized tissue reaction or protein denaturation in the vas deferens.

The irrigation and aspiration can be controlled to ensure that the intraluminal pressure within the bodily lumen does not exceed 3 psi during continuous irrigation and aspiration. The maximum intraluminal pressures can range from 0.0 psi to 6 psi.

The probe can be configured to provide mechanical agitation to the occlusive hydrogel during the irrigation and aspiration process to accelerate the mechanical breakdown and surface contact causing dissolution of the hydrogel by the sodium bicarbonate solution. Mechanical agitation can be provided by an ultrasonic generation source connected to the proximal end of the probe.

Mechanical agitation can be provided by a vibratory generation source connected to the proximal end of the probe.

Mechanical agitation can be provided by a motor providing rotational motion and is connected to the proximal end of the probe.

Mechanical agitation can be further enhanced by protrusions, bristles, brushes, indentations, coils, loops, and angulations of the probe to further enhance the mechanical agitation of the probe on the occlusive hydrogel.

An external vibratory source can be applied to the bodily lumen during instillation of the dissolving media or sodium bicarbonate solution to enhance the agitation and action of the dissolving media.

The removal system can also supply a lavage of sodium bicarbonate at the completion of the removal step. Additional lavage media options include saline, phosphate buffered saline, Ringer's lactate, and other biocompatible media suitable for the reproductive tract.

The removal system can have pressure relief valves to ensure that the intraluminal pressure of the vas deferens is controlled. Examples of pressure ranges are from 1 psi to 10 psi, or 3 psi as a nominal value.

The irrigation and aspiration function of the removal system can be monitored as a function of time. Examples of time durations are 1 minute to 10 minutes of irrigation and aspiration, or 4 minutes as a nominal time duration.

Alternatively, the irrigation and aspiration function of the removal system can be performed using a predetermined volume of sodium bicarbonate solution, of other dissolving solution, and terminating the step when the fluid volume is exhausted. Examples of fluid volumes include 10 cc to 250 cc, or 50 cc as a nominal fluid volume.

At the conclusion of the irrigation and aspiration function of the removal system, a final irrigation lavage can be performed with the visual confirmation of effluent from the patient's urethra to signify a patent vas deferens.

The advancement of the removal system guidewire or probe past the hydrogel implantation site is another confirmation that the occlusive hydrogel has been removed.

Additionally, the advancement of the removal system catheter past the hydrogel implantation site over the wire is another confirmation that the occlusive hydrogel has been removed.

The removal system can be configured to have a force or flow measurement system to confirm or quantitate the restoration of patency in the bodily lumen during lavage.

The delivery or removal systems can be introduced into the lumen of the reproductive tract by a wrap around sheath designed to penetrate the vas deferens or fallopian tube. The wrap around sheath can also contain a needle or other sharp implement to facilitate penetration into the lumen. Once entry into the lumen is achieved and confirmed by the advancement of the probe, the wrap around sheath can be retracted, peeled away, or removed from the delivery or removal system.

BRIEF DESCRIPTION OF THE DRAWINGS

The drawings shown and described are exemplary variations and non-limiting. Like reference numerals indicate identical or functionally equivalent features throughout.

FIG. 1A shows the typical location of the vas deferens in the scrotum, however anatomical variations are possible.

FIG. 1B illustrates the vas deferens positioned in a ring clamp for percutaneous insertion.

FIG. 1C illustrates an isolated vas deferens that is visible through the scrotal skin.

FIGS. 17A to 17F illustrates the injection of media for hydro-distension into the vas deferens. FIG. 17A shows the injection of media for hydro-distension into the vas deferens before and after probe insertion to lavage the lumen for clearing the bodily lumen of material and preparing for hydrogel insertion.

FIG. 17B shows the injection of media for hydro-distension before and after probe insertion to confirm intraluminal placement by a force, flow rate, or volume measurement of the media injection.

FIG. 17C shows the injection of media for hydro-distension before and after probe insertion in combination with ultrasound or radiographic imaging for confirmation of intraluminal placement.

FIG. 17D shows the injection of media for hydro-distension before and after probe insertion by confirming lavage through the urethra.

FIG. 17E shows the injection of a primer media for assisting in the gelation of the hydrogel.

FIG. 23A shows split needle removal after confirmation of intraluminal placement.

FIG. 24B illustrates the retraction of the probe back into handle. FIG. 24C shows a variation of the delivery system. FIG. 24D illustrates the steps of placing the delivery system within the vas deferens. FIG. 24E shows another handle configuration of the delivery system. FIG. 24F shows that the trocar can be removed from the central lumen prior to probe delivery. FIG. 24G illustrates a handle slide for retracting the trocar. FIG. 24H illustrates the steps of delivery of the probe and hydrogel into the vas deferens. FIG. 24I shows a variation of the delivery system. FIG. 24J illustrates a variation of the method of placing the delivery system and hydrogel into the vas deferens.

FIG. 25A shows the injection of media for clearing the bodily lumen of material and preparing for hydrogel insertion after delivery sheath insertion.

FIG. 25B shows injection of media for assisting in the gelation of the hydrogel after delivery sheath insertion.

FIG. 30A shows the injection of media, gas, or air for confirming occlusion using a force measurement system. The injection of media can also be used for initiating gelation of the hydrogel.

FIG. 33A shows a system where the site of insertion into the vas deferens can be tagged with a visual tattoo on the external surface of the vas deferens.

FIG. 33B shows a system for future identification of the delivery of the occlusive hydrogel in the bodily lumen where the site of insertion into the vas deferens can be tagged with an external clip that is also visible via ultrasound or radiographic imaging. The clip does not occlude the vas deferens, but only marks the site of insertion that can be identified in the future.

FIG. 33C shows a system for future identification of the delivery of the occlusive hydrogel in the bodily lumen where the site of insertion into the vas deferens can be tagged with a circumferential band around the vas deferens to permanently identify the site of insertion. The circumferential band is slightly elastomeric and is not restrictive to occlude the bodily lumen and does not create tissue necrosis.

FIG. 34A illustrates the removal system with irrigation and aspiration holes. FIG. 34B shows the handle of the removal system in a cross-sectional view. FIG. 34C shows a variation of the dual lumen removal system with rotating handle. FIG. 34D shows the dual lumen removal system with rotating handle in a cross-sectional view.

FIG. 48B shows a close-up view of the wraparound penetrating sheath. FIG. 48C shows the probe through the distal opening of the wrap around penetrating sheath. FIG. 48D shows the wrap around penetrating sheath slightly retracted with both the probe and intraluminal catheter through the distal opening of the wrap around penetrating sheath. FIG. 48E shows the wrap around penetrating sheath completely retracted and separate from the delivery or removal handle.

FIGS. 49A to 49C illustrate a wrap around penetrating sheath that can have a needle configured at the distal end. FIG. 49A shows the delivery or removal handle with wrap around penetrating sheath with needle. FIG. 49B shows a close-up view of the wrap around penetrating sheath with needle. FIG. 49C shows the wrap around penetrating sheath with needle completely retracted and separate from the delivery or removal handle.

FIG. 50A shows the removal handle with a transparent section identifying the alternating lumens mechanism. FIG. 50B shows the removal system in cross-section with a close-up illustration of the rotation wheel for alternating the lumens.

FIG. 51A shows in cross-section the distal end of the dual-lumen catheter. FIG. 51B shows a side-view of the distal end of the removal catheter with the aspiration hole and irrigation side holes.

DETAILED DESCRIPTION

Figure 1A:
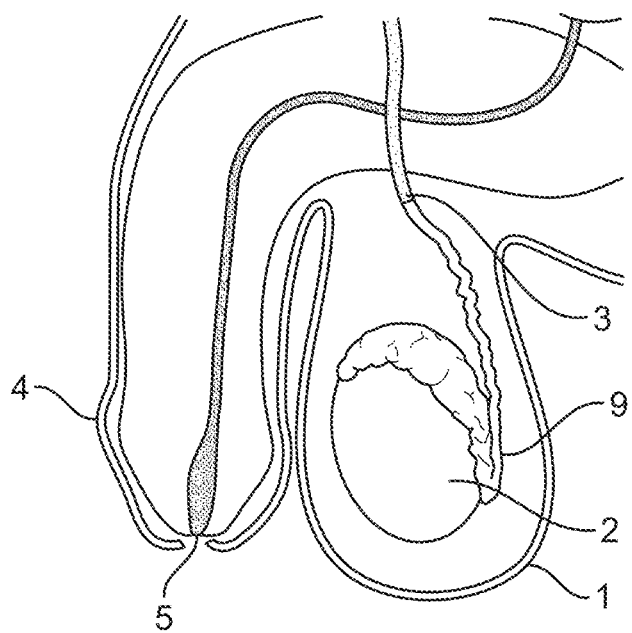
FIGS. 1A to 1C illustrate the anatomical location of the vas deferens in the male reproductive tract.
Figure 1B:
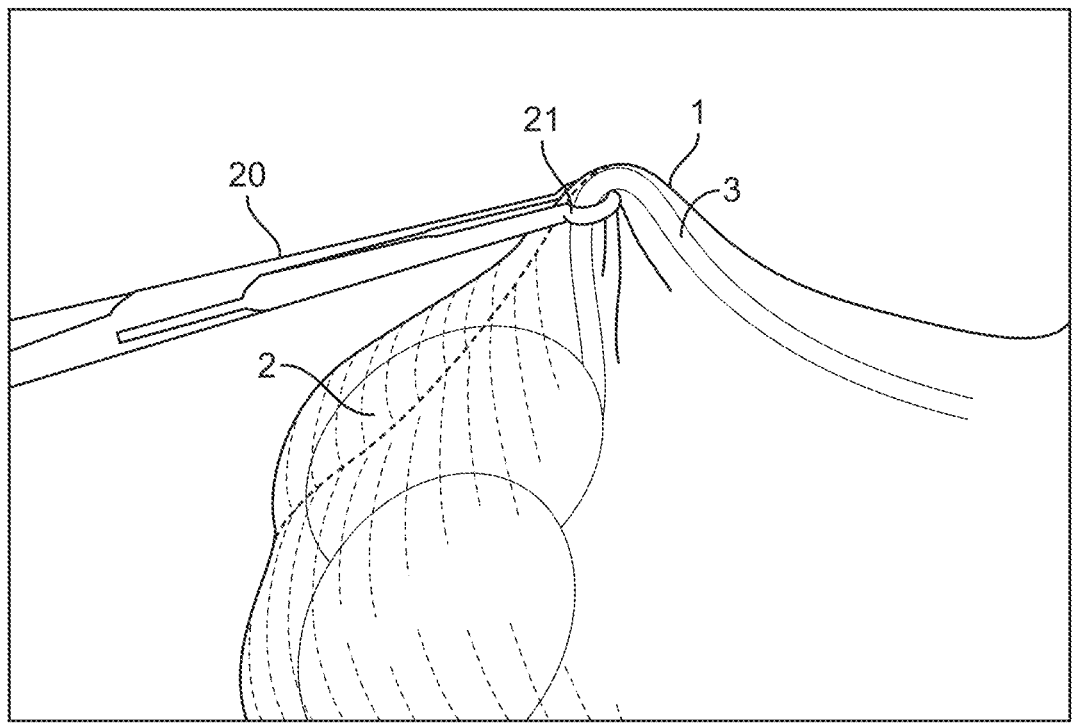
Figure 1C:
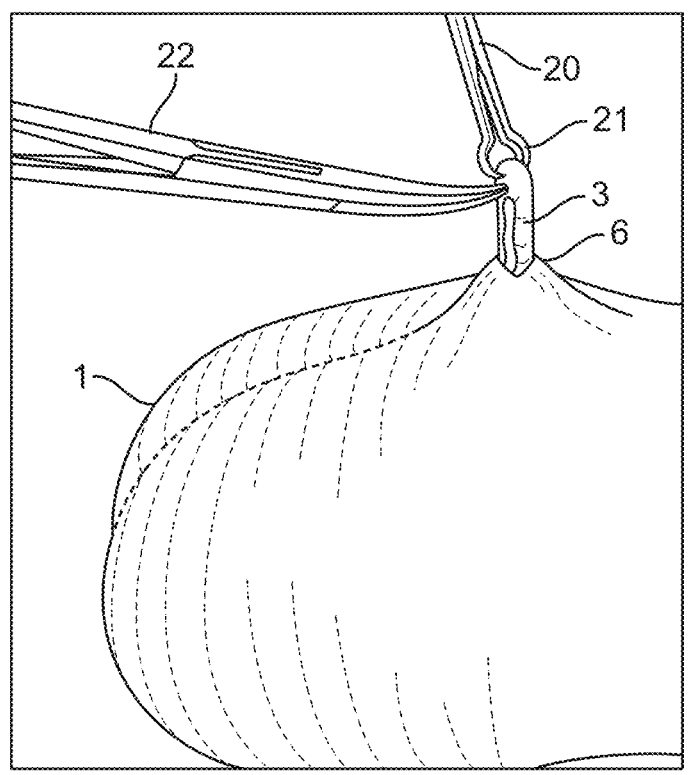

FIGS. 1A to 1C illustrate in a cross-sectional view the typical anatomical location of the vas deferens 3 in the male reproductive tract, however anatomical variations are possible. FIG. 1A shows the location of the vas deferens 3 in the scrotum 1. Sperm produced in the testes 2 and matured in the epididymis 9 traverse the vas deferens 3. In an ejaculation, sperm will be ejected out of the penis 4 through the urethra 5. For male sterilization, vasectomy procedures ligate the vas deferens 3 to prevent the passage of sperm. For male contraception designed to be reversible, occlusion devices made from a hydrogel are placed within the vas deferens 3 to prevent the passage of sperm. These hydrogels can also allow for the passage of fluids but due to their porosity, the sperm cannot permeate through the hydrogel matrix. Some hydrogels can also be designed for removal with the introduction of dissolving agents. Dissolving agents or agents that disassociate the hydrogel include solutions such as sodium bicarbonate solution, dimethyl sulfoxide, or others can be delivered to the vas deferens 3 to remove the occlusive hydrogel. Once dissolved, patency within the vas deferens 3 can be restored for a return to fertility for the male.

FIG. 1B illustrates the isolation of the vas deferens 3 from the scrotum 1 by the placement and positioning of a ring clamp 20. The physician palpates the scrotum 1 to identify and elevate the vas deferens 3 and uses the ring clamp 20 and holding ring 21 to grasp the vas deferens 3. Alternatively, the vas deferens can be identified and isolated by other imaging modalities, not shown in this figure. For the insertion of hydrogels and occlusive devices within the vas deferens 3, the ring clamp 20 is used as a stabilizer for the percutaneous insertion of an occlusive device.

FIG. 1C illustrates an isolated vas deferens 3 that is visible through the scrotum 1 through an opening in the scrotal skin 6. The vas deferens 3 is lifted by the holding ring 21 of the ring clamp 20. Fascia and other tissues are removed by dissecting forceps 22 to further isolate the vas deferens 3. At this juncture, non-percutaneous or direct access to the vas deferens 3 is possible.

Figure 2A:
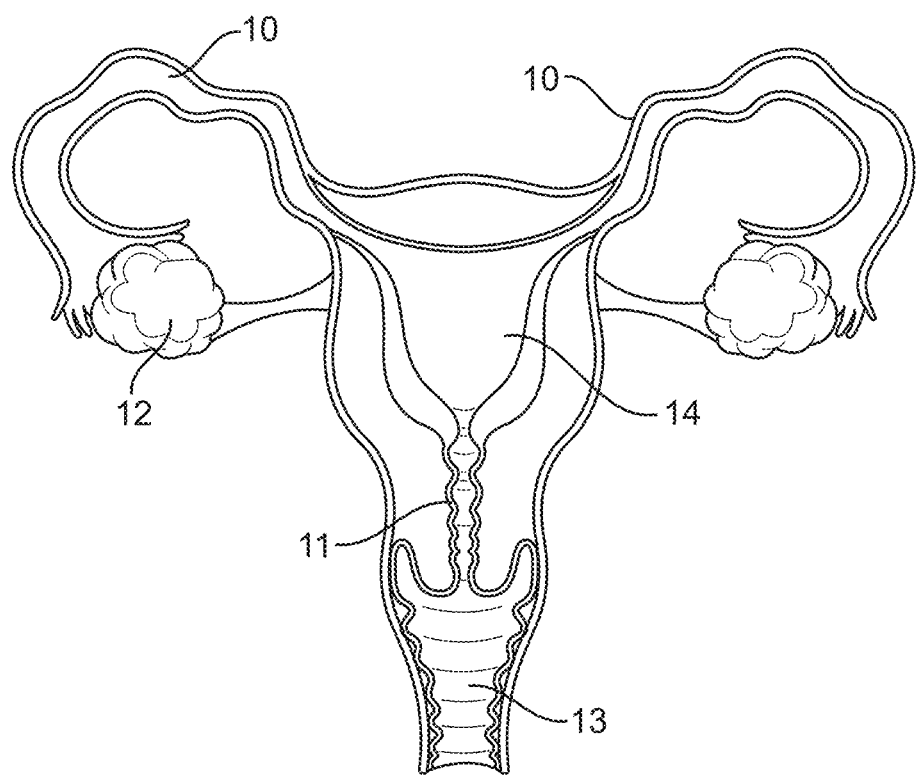
FIG. 2A illustrates the location of the fallopian tube in the female reproductive tract.

FIG. 2A illustrates in a cross-sectional view the location of the fallopian tube 10 in the female reproductive tract. The external opening of the uterus 14 is through the cervix 11 which is located in the vagina 13. At the distal end of the fallopian tube 10 is the ovary 12 in which follicles mature and eggs are emitted. Sperm from the male fertilize the egg within the fallopian tube 10. For female sterilization, the fallopian tubes 10 are ligated. For female contraception in which is intended to be reversable, occlusive devices made from a hydrogel can be placed within the fallopian tubes 10 to inhibit the passage of sperm and thereby prevent the fertilization of an egg.

Figure 2B:
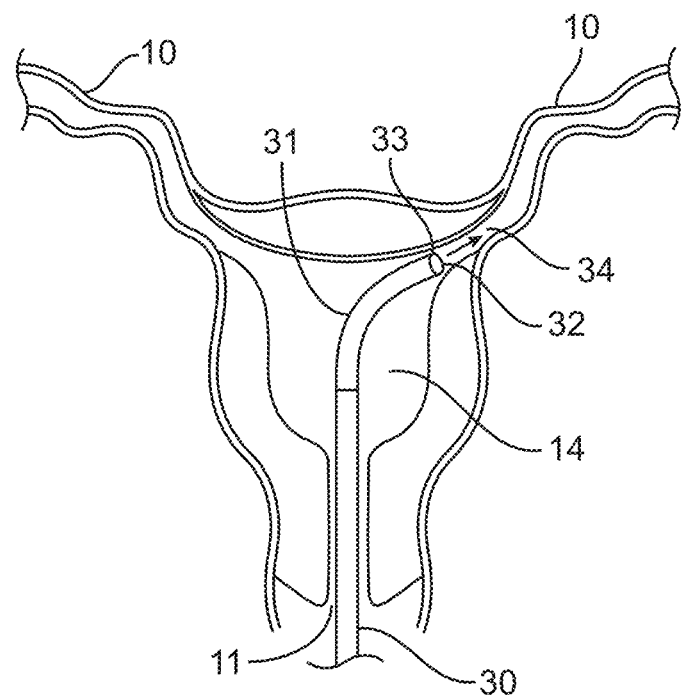
FIG. 2B illustrates the position of a hysteroscopically positioned catheter at the os of the fallopian tube prior to insertion of the hydrogels in the fallopian tube for female contraception.

FIG. 2B illustrates the position of a hysteroscope 30 for the positioning of a delivery catheter 31 at the os 34 of the fallopian tube 10 prior to insertion of the hydrogels for female contraception. The hysteroscope 30 provides an internal image of the uterus 14 and identifies the os 34 for direct insertion of the hydrogel within the fallopian tube 10. Alternatively, the fallopian tube 10 can be accessed directly through a trans-abdominal approach involving laparoscopy or surgical incision.

Figure 3:
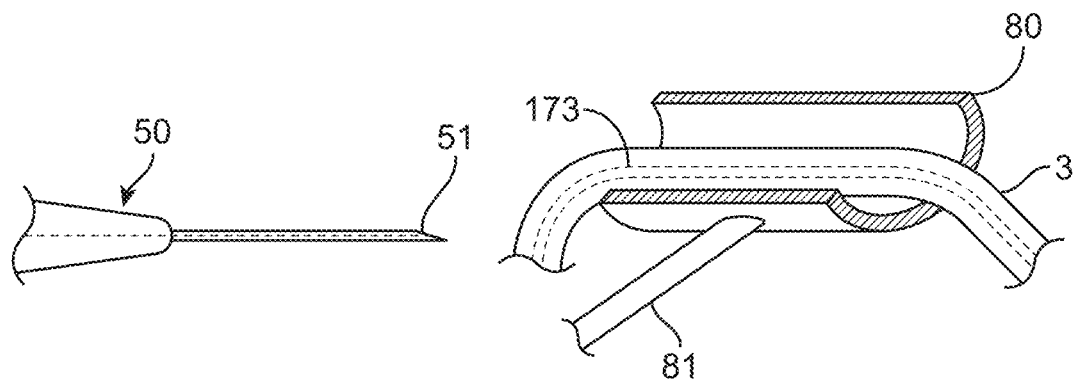
FIG. 3 shows a variation for isolating the vas deferens with half-pipe or side-support system.

FIG. 3 shows that isolating the vas deferens 3 from the scrotum (not shown) can be performed with half-pipe 80 which can provide a side-support system to isolate and stabilize the vas deferens 3. The side support system can circumferentially surround the vas deferens so that direct access with delivery instrument 50 can be made without rotation of the tubular structure of the vas deferens 3. The half pipe 80 also provides a flat platform on the posterior portion of the vas deferens 3 to facilitate a linear insertion of the distal end of delivery instrument 51 into delivery site 173 on the anterior surface of vas deferens 3. While positioned within the side support system 80, the distal end of the delivery instrument 51 can penetrate the anterior wall of the vas deferens 3 for the delivery or removal of occlusive devices.

Figure 4:
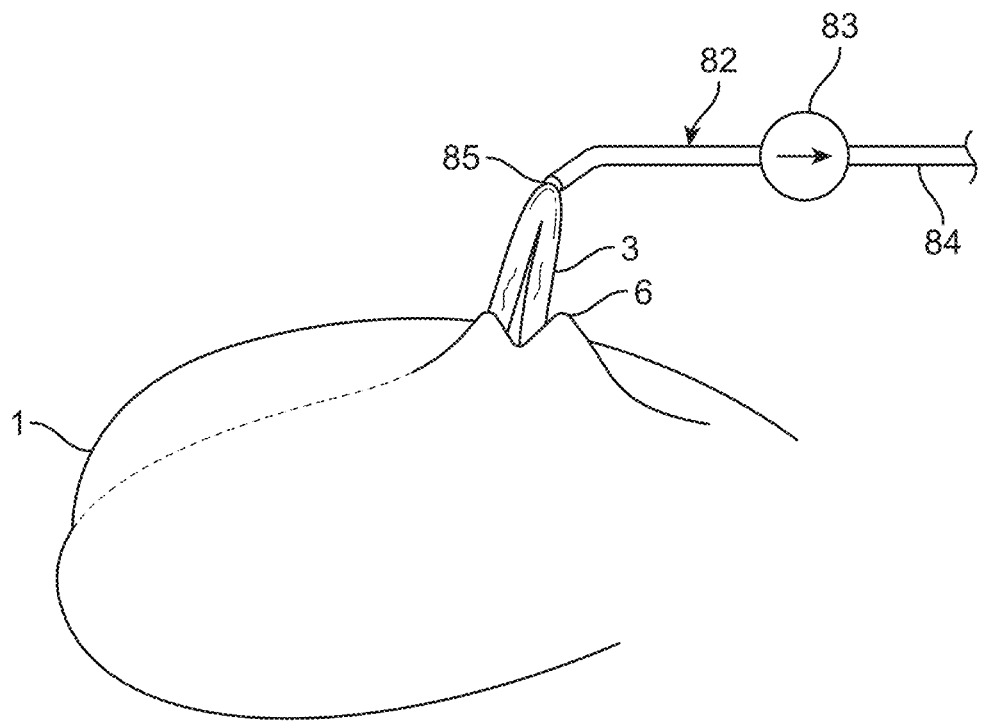
FIG. 4 shows a schematic for isolating the vas deferens with vacuum holding the anterior wall.

FIG. 4 shows in schematic form a holding device 82 for applying negative pressure with a vacuum source 83 via aspiration conduit 84. The distal end 85 of the holding device 82 attaches to the anterior wall of the vas deferens 3 through the scrotal skin opening 6 for isolating the vas deferens 3 from the scrotum 1. Through the negative pressure holding force, the vas deferens 3 is stabilized for subsequent delivery of an occlusive device.

Figure 5A:
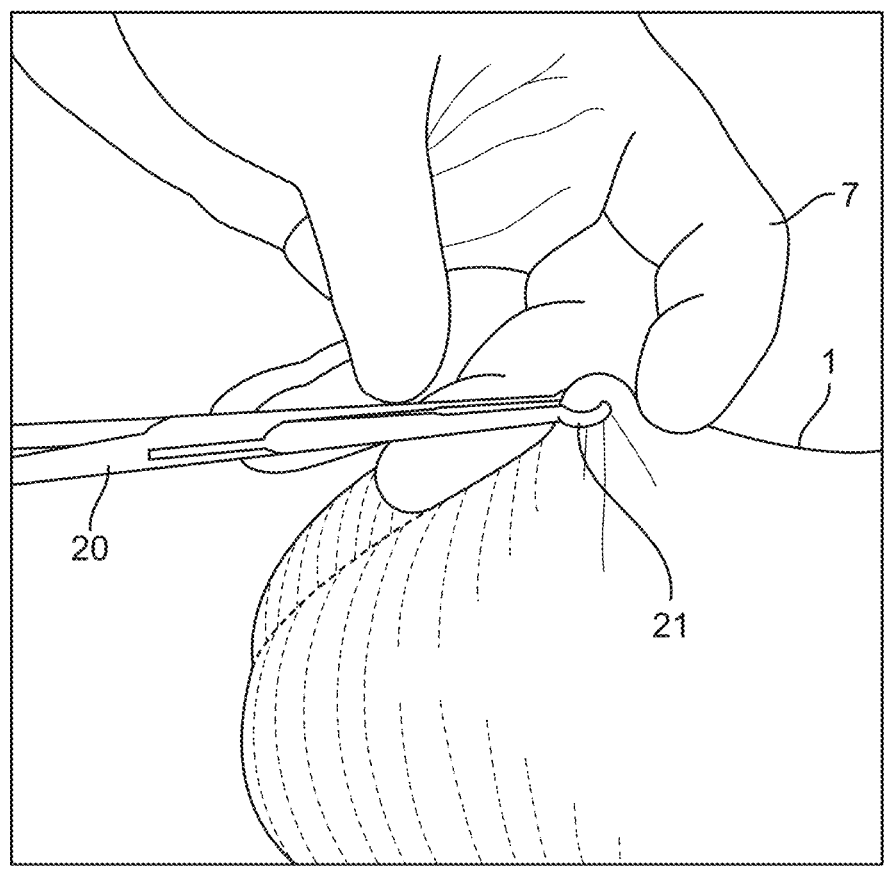
FIG. 5A and FIG. 5B illustrate a variation for isolating the vas deferens with ring clamp and holding mechanism for the delivery and removal system. Note that additional imaging modalities could be employed for identification and isolation of the vas deferens. These modalities are not shown.
Figure 5B:
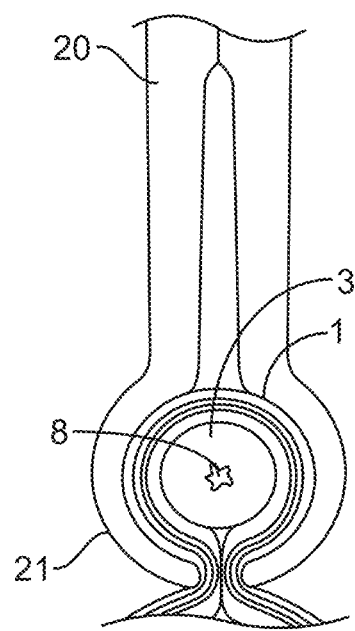

FIG. 5A and FIG. 5B illustrates the technique for isolating the vas deferens 3 with ring clamp 20 for traditional vasectomy procedures. The physician's fingers 2 palpate the vas deferens 3 from the scrotum land holding mechanism for the delivery and removal system.

FIG. 5B shows in a cross-sectional view the structure of the vas deferens 3 within the scrotal skin 1 and contained within the holding ring 21 of ring clamp 20. Within the vas deferens 3 is the intraluminal space or lumen 8. For the delivery of occlusive devices, the lumen 8 is the intended target or location for the placement of the occlusive device. Unintentional placement of the delivery instrument into other portions of the vas deferens 3 wall, fascia, or interstitial spaces can render subsequent delivery of the occlusive device or removal system procedure unsuccessful. The unintended placement can damage the structure of the vas deferens 3 or prevent the potential for reversing the occlusion and a return to fertility in the future. Hence the proper identification and placement of the occlusive device within the lumen 8 is a requirement for both contraception and reversal in the future.

Figure 6:
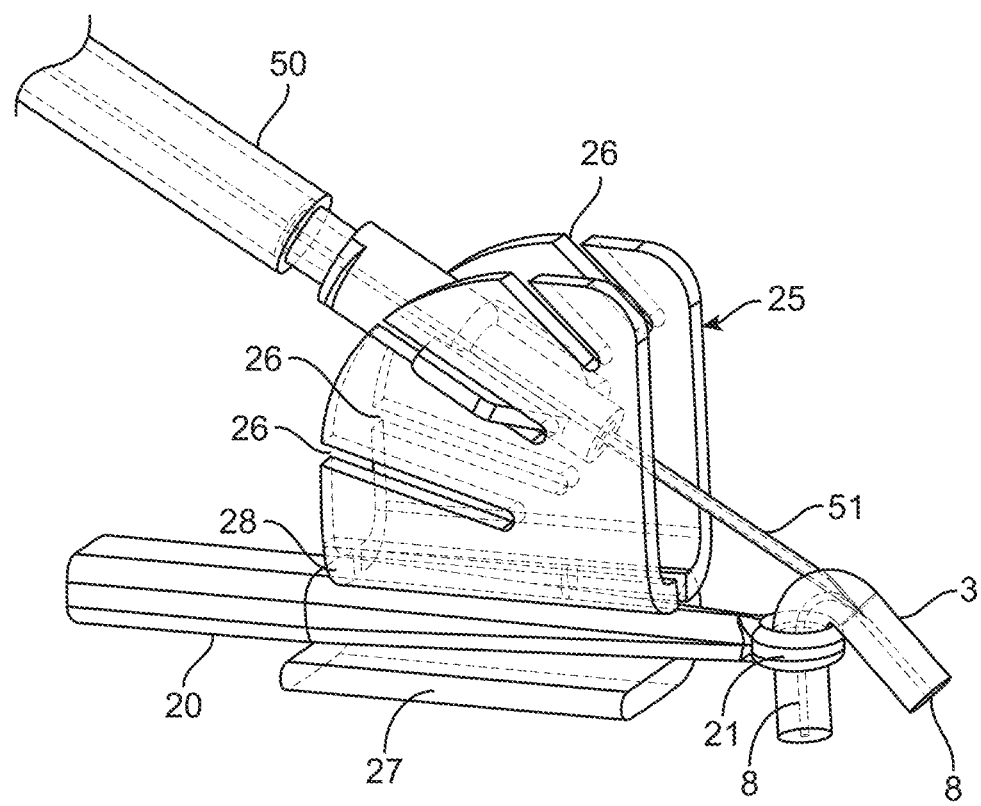
FIG. 6 illustrates a variation for isolating the vas deferens with angle miter for
controlled insertion of the delivery system.

FIG. 6 illustrates that the vas deferens 3 can be isolated with angle miter 25 for
  controlled insertion of a delivery or removal system. Delivery instrument 50 is positioned within a predetermined slot 26 for the controlled angle of insertion of the distal end of the delivery instrument 51 within the vas deferens 3. The angle miter 25 is clipped onto the ring clamp 20 by holder groove 28 and base 27 while holding ring 21 stabilizes the vas deferens 3. Distal end of the delivery instrument 51 is then placed through the anterior wall of the vas deferens 3 and into the lumen 8. Delivery instrument 50 can be used for the placement of an occlusive device or the removal agent. In either situation, the angle miter 25 can facilitate the proper placement into lumen 8.

Figure 7:
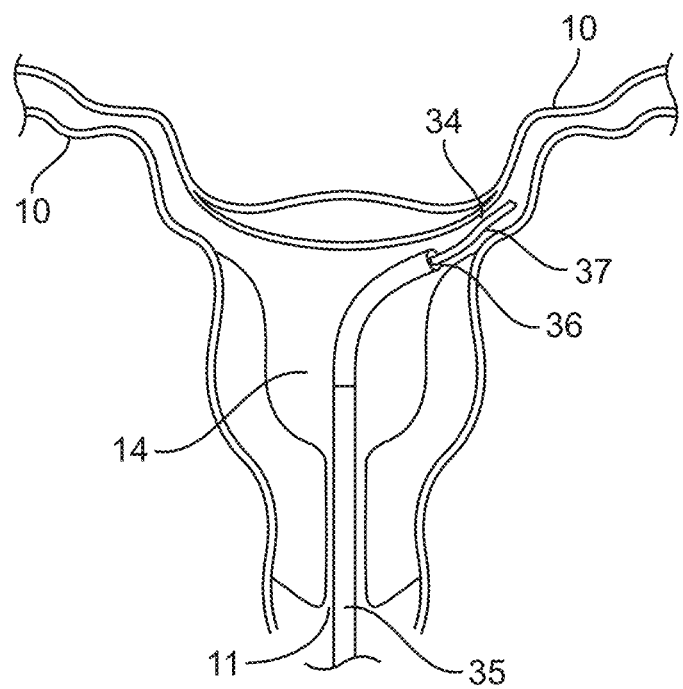
FIG. 7 illustrates a transcervically positioned catheter for intrauterine placement into
the os of the fallopian tube.

FIG. 7 illustrates a transcervically positioned catheter 35 for intrauterine placement into the os 34 of the fallopian tube 10. The catheter 35 is placed through cervix 11 into the uterus 14. Through distal end opening 36 of catheter 35 delivery instrument 37 intubates fallopian tube 10. Once positioned within the fallopian tube 10, the delivery of an occlusion device or removal agent can be performed.

Figure 8:
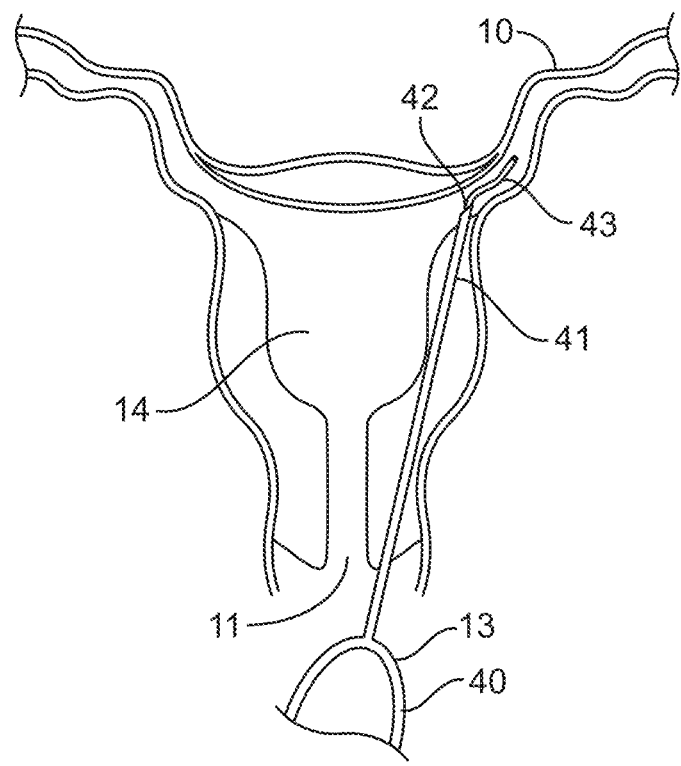
FIG. 8 illustrates a variation for using transvaginal ultrasound to deliver the agent
directly into the fallopian tube.

FIG. 8 illustrates delivering the occlusive device or removal agent directly into the fallopian tube 10 with transvaginal ultrasound. Transvaginal ultrasound transducer 40 is placed into the vagina 13 with transvaginal needle 41 penetrating through the uterus 14 with distal tip of transvaginal needle 42 penetrating directly into fallopian tube 10 with delivery catheter 43. The penetration of the transvaginal needle 41 and location of the fallopian tube 10 is visualized with the aid of ultrasonic imaging (ultrasound console and monitor not shown).

Figure 9:
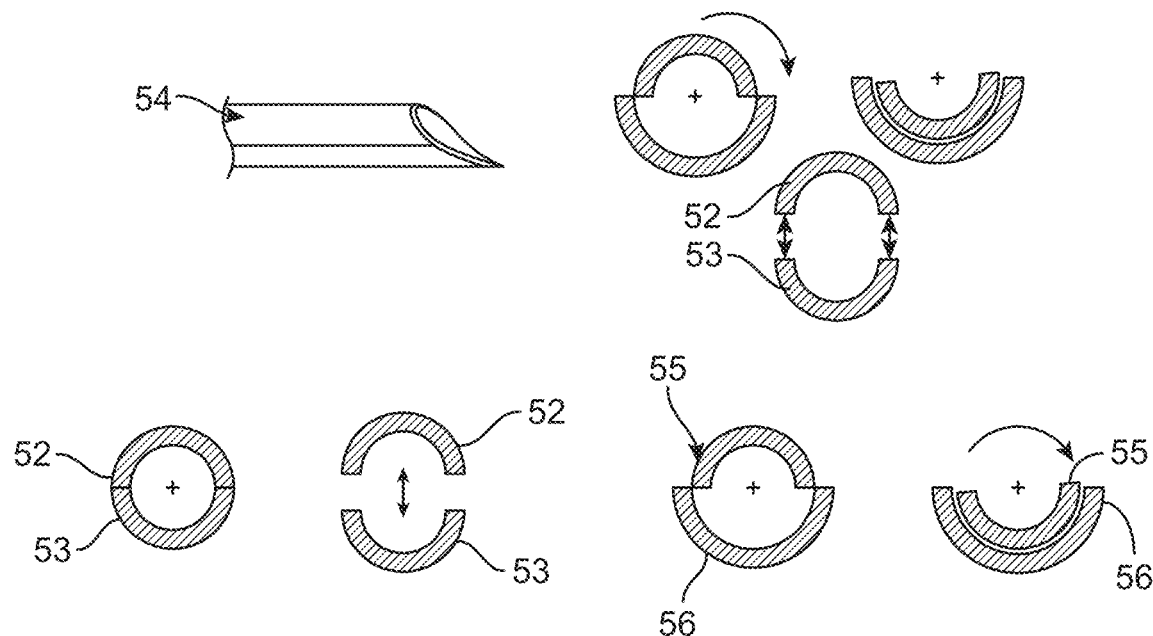
FIG. 9 illustrates a variation for providing intraluminal insertion into a bodily lumen using a split needle insertion system with two-hemispherical sections. The hemispherical sections can be split apart in a radial direction from collinear central axis. The hemispherical sections can be rotated along their central axis to form an opening in the insertion needle. In either configuration, the portions of the split do not have to be equal in size, only cylindrical at insertion and a second configuration with an opening. Multiple sections greater than two are possible.

FIG. 9 illustrates providing intraluminal insertion into a bodily lumen using a split needle insertion system with two-hemispherical sections. Traditional insertion within a bodily lumen is performed with a needle that is constructed from thin-walled tubing. The tubing can be made with stainless steel, nitinol, titanium, or other biocompatible materials. Hallow, cylindrical needle tubing is defined by a continuous circumferential wall. Split needles 54 are configured to penetrate the wall of a bodily lumen but once penetrated is accomplished, the split needle 54 can separate into two halves. In one configuration, split needle 54 can separate radially into anterior half 52 and posterior half 53. Once radially separated, split needle 54 can be removed from the delivery or removal system without requiring an exchange or back loading from other components that occupy the central axis of the delivery or removal system.

FIG. 9 illustrates that split needle 54 can separate by rotating the anterior half 55 onto the posterior half 56 along the central axis. Once the bodily lumen is penetrated, rotation of split needle 54 eliminates the continuity of the cylindrical wall, thereby allowing other elements of the delivery or removal system to be introduced without a back exchange.

Figure 10:
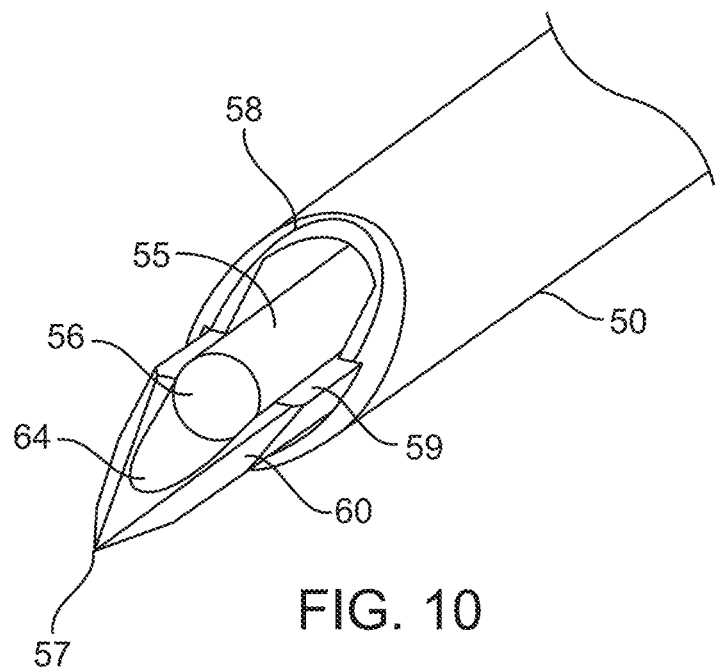
FIG. 10 illustrates a half-needle insertion system that houses the probe within the half needle section with a cut-away at its mid-section.

FIG. 10 illustrates a half-needle insertion system 64 for delivery instrument 50 that houses a probe 55 within the half needle section with a cut-away 60 at its mid-section forming a half-cylinder. The half needle tip 57 provides a minimal penetration implement in which the probe 55 is contained with probe tip 56 designed to advance into a bodily lumen once the penetration into the lumen is accomplished. Delivery instrument 50 is configured over the half needle insertion system 64 in which the probe 55 and half needle insertion system 64 can translate inside the delivery instrument 50 through distal end opening of the 58 of the delivery instrument 50.

Figure 11:
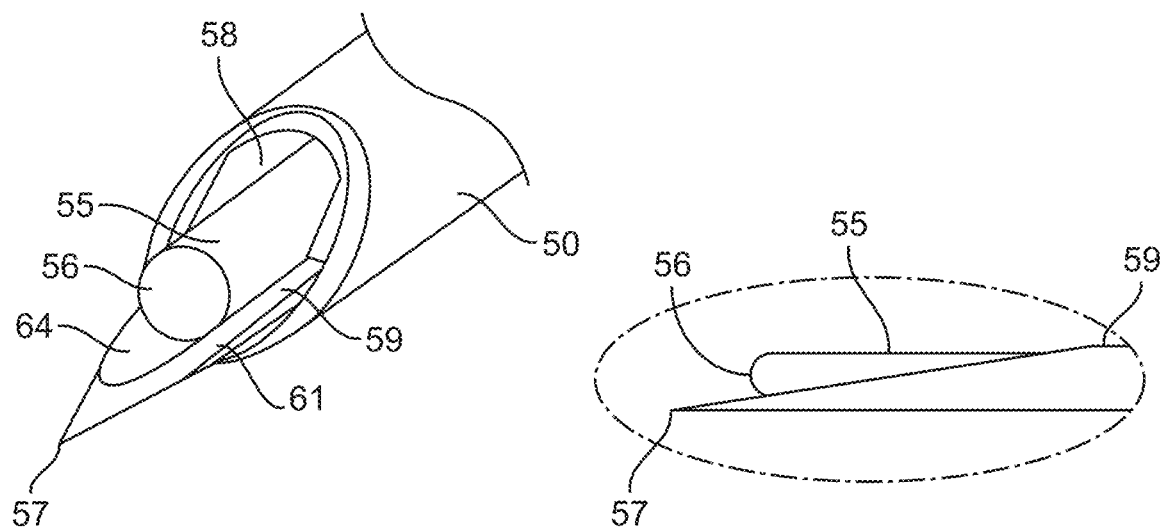
FIG. 11 illustrates a half needle with a cut-away that is more pointed at the distal end and tapers up at the equator.

FIG. 11 illustrates a half needle insertion system 64 with a cut-away that is more pointed at the distal end 57 and tapers up at the equator or mid-section 59 of the half cylinder. In this configuration, the distal end of the half needle insertion system 64 contains a smaller wall for housing the probe 55. Within FIG. 11, the dashed lines oval shows a side view of the sharper tip half needle insertion system 64 in relation to the probe 55.

Figure 12:
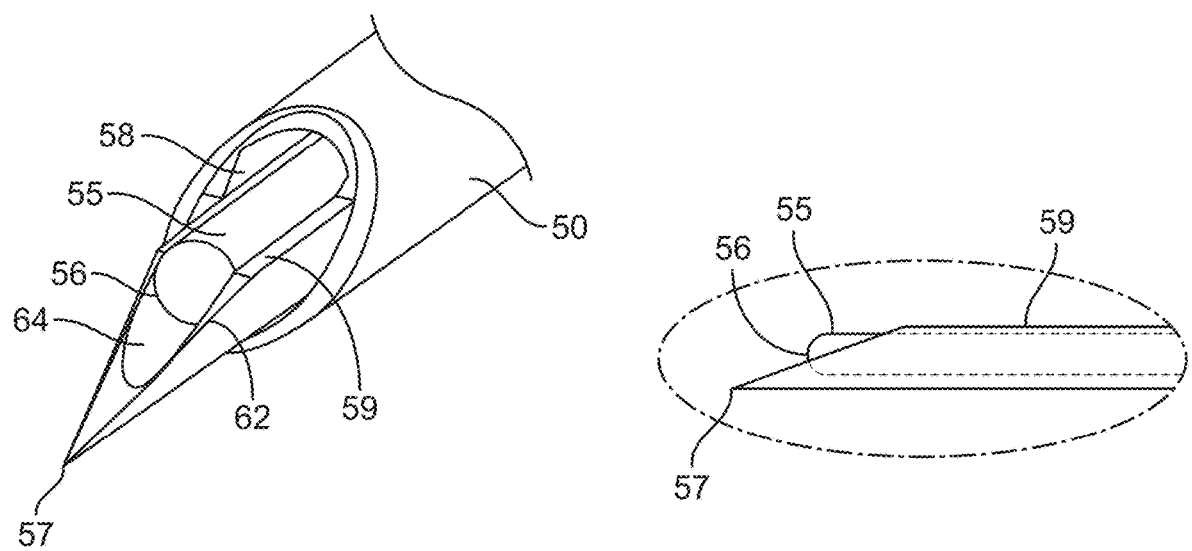
FIG. 12 illustrates a half needle variation in which the cut-away is located above the equator.

FIG. 12 illustrates a variation of the half needle insertion system 64 in which the cut-away 59 is located above the mid-section or equator of the cylindrical tubing so that a greater portion of the probe 55 is contained within the half needle. The oval with dashed lines shows a side view of this configuration of the half needle insertion system 64.

Figure 13:
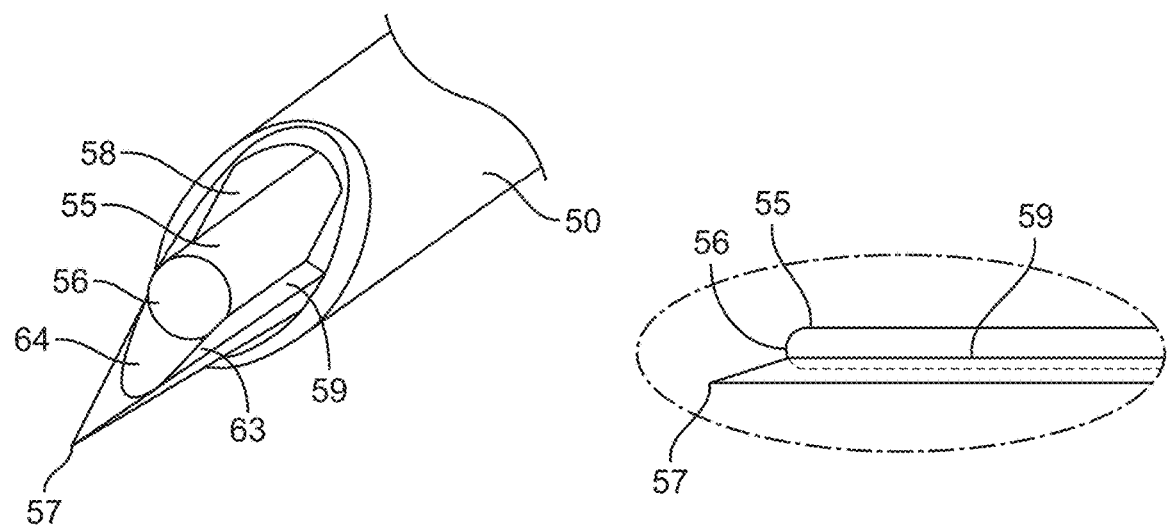
FIG. 13 illustrates a half needle variation with the cut-away below the equator.

FIG. 13 illustrates that the half needle insertion system 64 with the cut-away portion 59 of the cylindrical tubing is situated below the equator. The oval with dashed lines shows a side view of this configuration.

Figure 14:
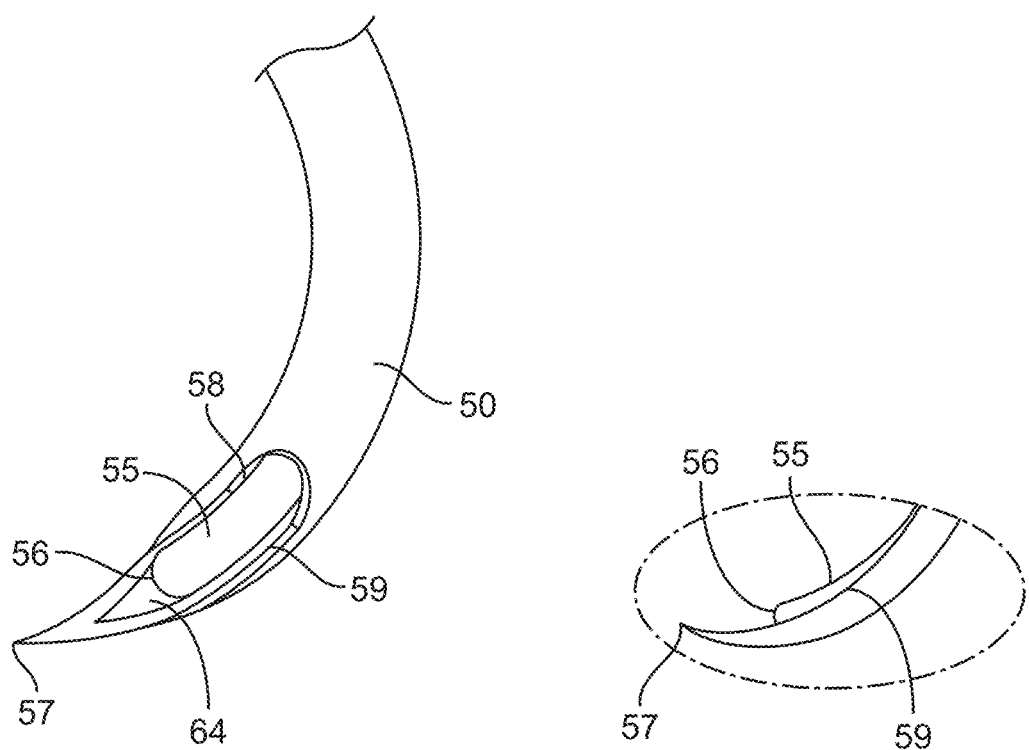
FIG. 14 illustrates a curved half needle variation for probe insertion.

FIG. 14 illustrates a curved half needle insertion system 64 can be configured for probe 55 insertion into a bodily lumen. The dashed lines oval shows a side view of the curved needle cut away section 59 and distal tip 57 in relation to probe 55 and probe tip 56. The curvature of the half needle forces the probe 55 to ride along the inside arc or curve of the half needle. The curvature can allow for an oblique entry in the bodily lumen.

Figure 15:
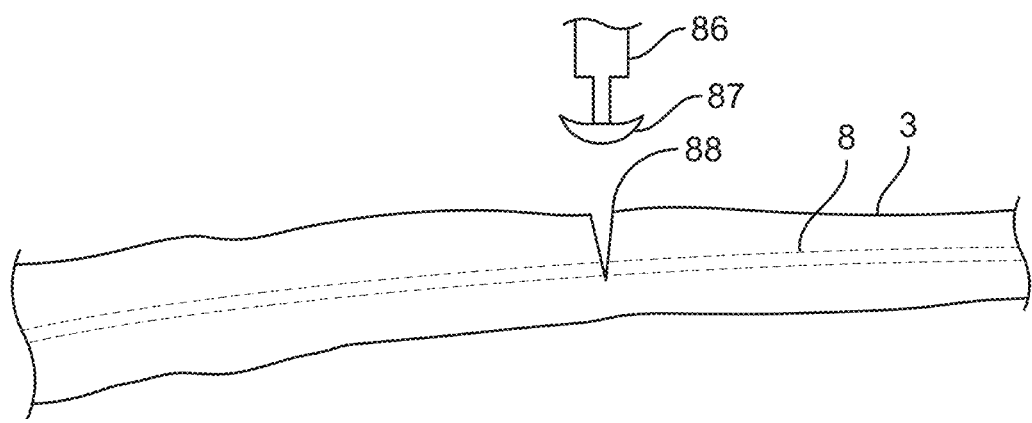
FIG. 15 illustrates a cutting tool with variable guillotine depth for hemi-spherical transection of the vas deferens for probe insertion.

FIG. 15 illustrates an alternative form of gaining access to a bodily lumen using cutting tool 87 with variable guillotine depth 86 for hemi-spherical transection 88 of the vas deferens 3 for probe (not shown) insertion. The hemi-spherical transection 88 provides direct access to lumen 8 indicated by dashed lines within the vas deferens 3.

Figure 16:
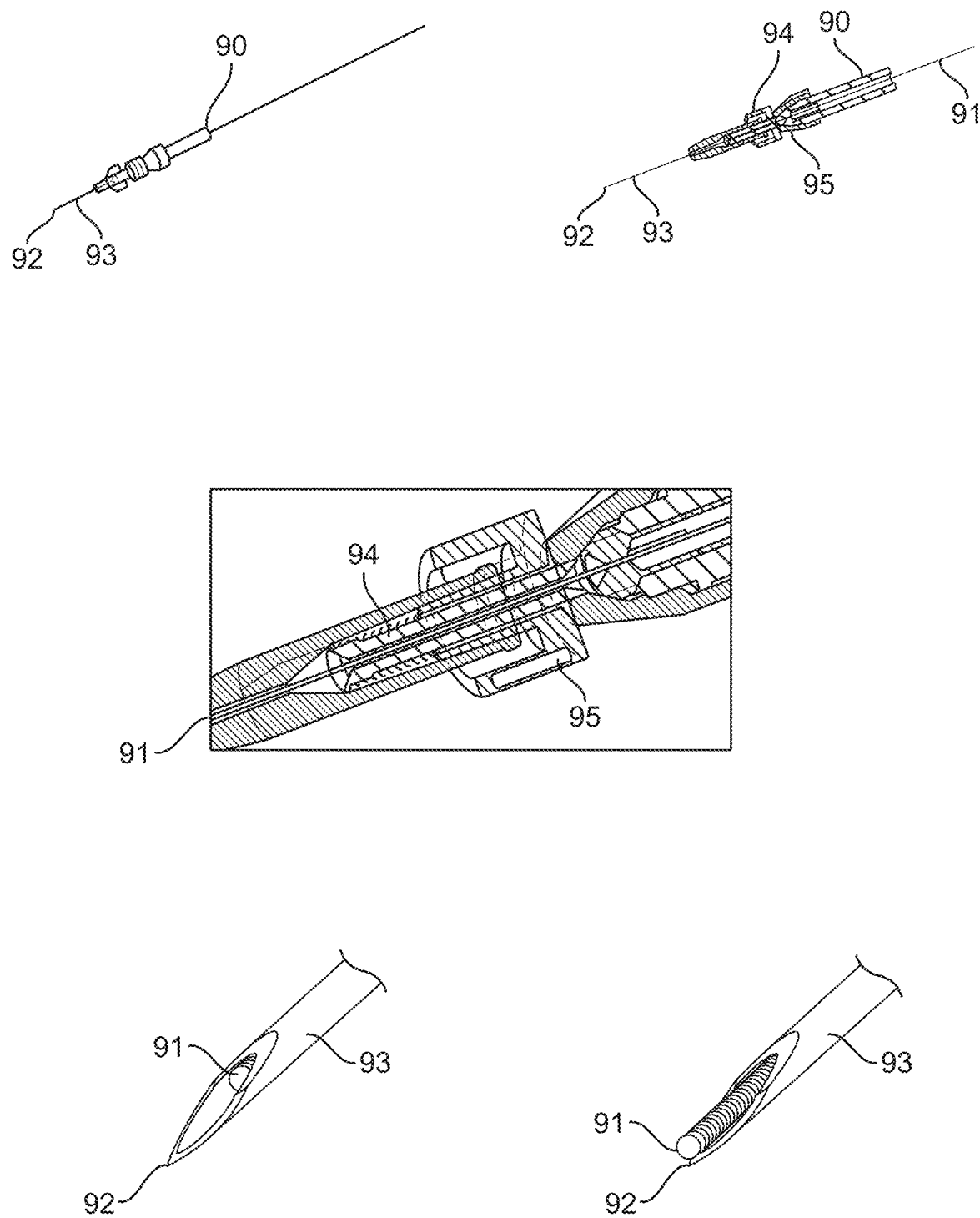
FIG. 16 illustrates a variation for confirming intraluminal placement into a bodily lumen using a spring-loaded retractable lancet system.

FIG. 16 illustrates using a spring-loaded retractable lancet system 90 for confirming intraluminal placement into a bodily lumen. A needle 93 with sharp distal tip 92 can be used to penetrate a bodily lumen (not shown). Once entry into the bodily lumen is achieved, probe 91 is spring loaded to advance automatically once the needle tip 92 reaches a point of less resistance as defined by the bodily lumen. The spring loading mechanism is contained in housing 95 with spring 94 under compression when the probe 91 is retracted within needle 93.

Figure 17A:
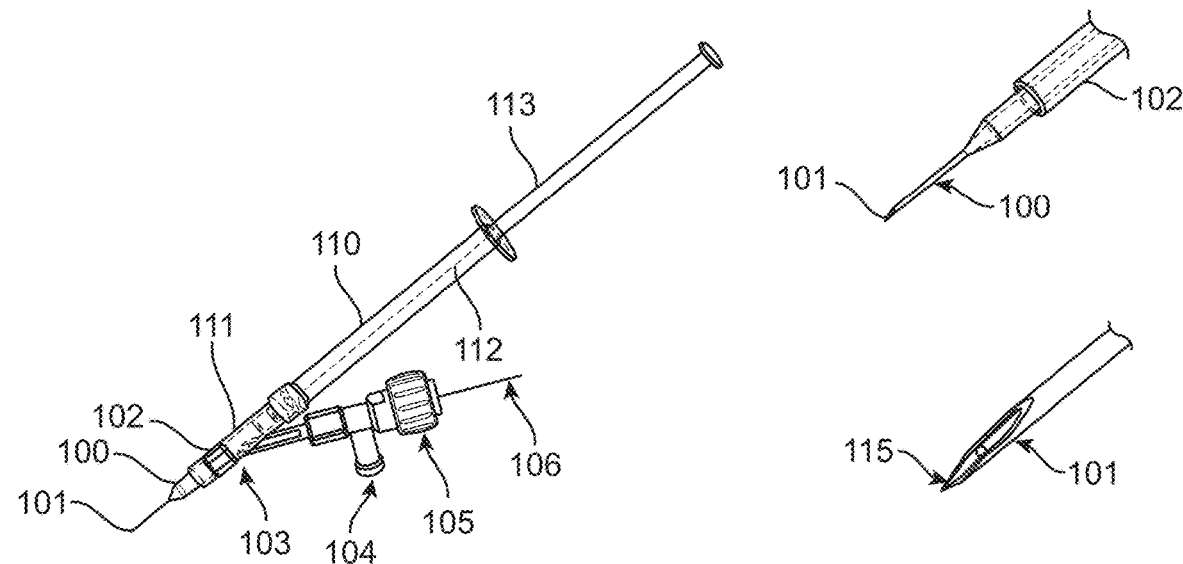

FIGS. 17A to 17F illustrates the injection of media for hydro-distension into a bodily lumen such the vas deferens or fallopian tube. FIG. 17A illustrates the components of a hydrogel delivery handle 110 for the injection of media for hydro-distension into the vas deferens before and after probe 106 insertion through fluid delivery port 104. Fluid media can be saline, phosphate buffered saline, Ringer's lactate, and other biocompatible fluids. Fluid media can be used to lavage the bodily lumen to clear the lumen of material, bodily fluids, stabilizing pH, affecting intraluminal temperature, and preparing the bodily lumen for hydrogel insertion. Media can also be a gas such as $CO_2$ or other gases. For the vas deferens, media can wash the lumen of remnant sperm and fluids to establish a uniform environment for the occlusion of the hydrogel in the lumen of the vas deferens. In practice, retractable half needle 115 is withdrawn within distal sheath 100 after insertion in the bodily lumen. Fluid media lavage can occur with the half needle 115 retracted or extended in the distal sheath 100.

Figure 17B:
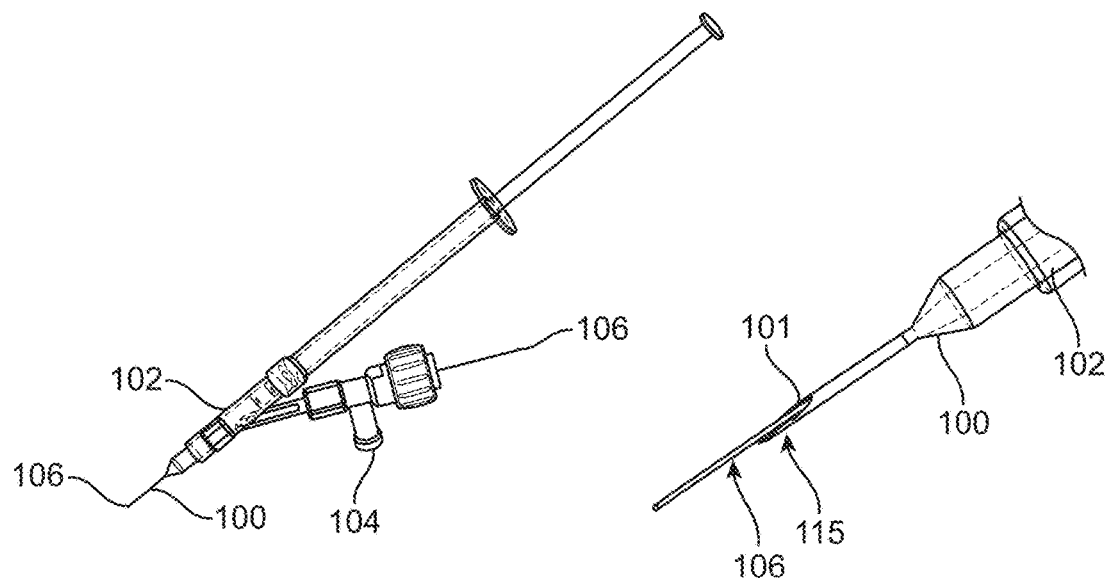

FIG. 17B shows the injection of media for hydro-distension before and after probe 106 insertion to confirm intraluminal placement by a force, flow rate, or volume measurement of the media injection (force, flow rate, or volume measuring device not shown). In practice, the flow of media in the bodily lumen will require less force, have a higher flow rate, or allow for a greater volume if the distal sheath 100 is located within the lumen.

Figure 17C:
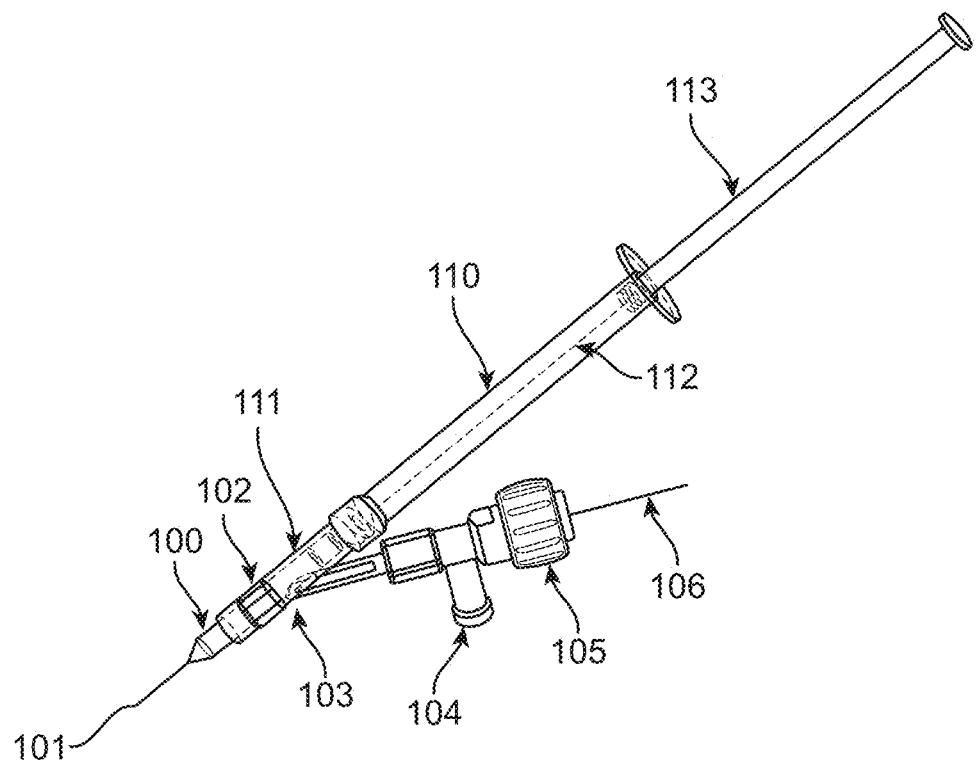

FIG. 17C illustrates that the injection of media for hydro-distension before and after probe 106 insertion can be performed in combination with ultrasound or radiographic imaging (imaging equipment not shown) for confirmation of intraluminal placement.

Figure 17D:
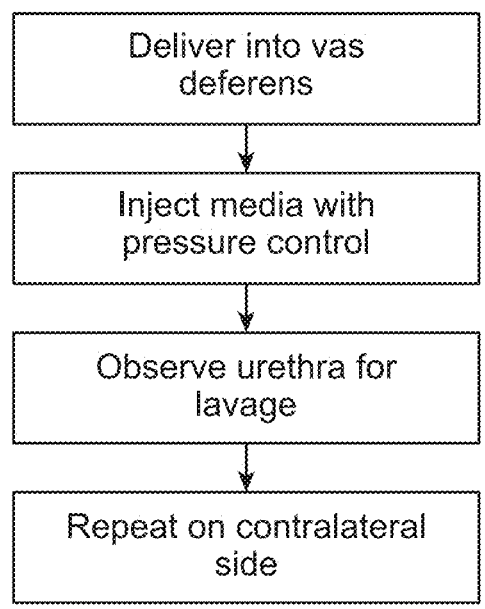

FIG. 17D illustrates the steps for the injection of media for hydro-distension before and after probe insertion by confirming lavage through the vas deferens or fallopian tube lumen of a reproductive tract. For the vas deferens, the distal sheath is delivered into the lumen of the vas deferens and followed by the injection of media. The fluid pressure, flow rate, and fluid volume can be monitored or governed by pressure control, flow rate control, and fluid volume measurement devices. While the fluid media slightly distends the potential space of the vas deferens lumen during injection, the excess lavage exits the reproductive tract through the urethra to confirm patency. These steps can be repeated for the contralateral side or other vas deferens.

Figure 17E:
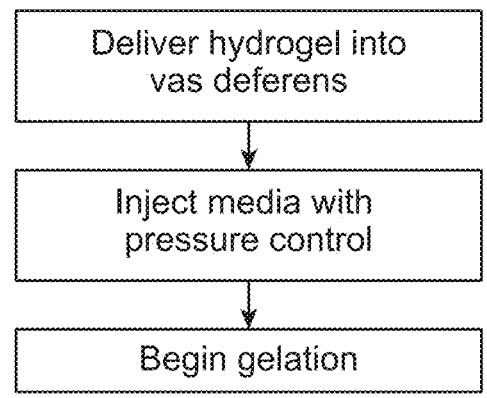

FIG. 17E illustrates that the injection of a media or gas can be used as a primer for assisting in the gelation of the hydrogel into the vas deferens. As a primer, the media can wash the lumen of excess materials, provide greater lubricity, deliver proteins for accelerate gelation of the hydrogel, provide for a uniform pH, or a pH beneficial to gelation.

Figure 18:
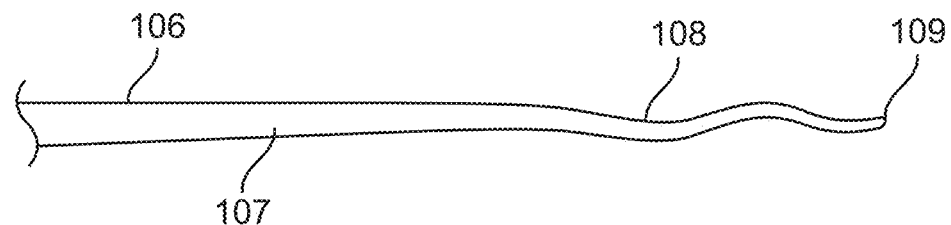
FIG. 18 shows probe insertion with a flexible tip.

FIG. 18 presents that the probe 106 can be configured for improved insertion with a flexible tip 109. Probe 106 has flexible section 108 near the distal end and gradually stiffer section 107 in the more proximal direction.

Figure 19:
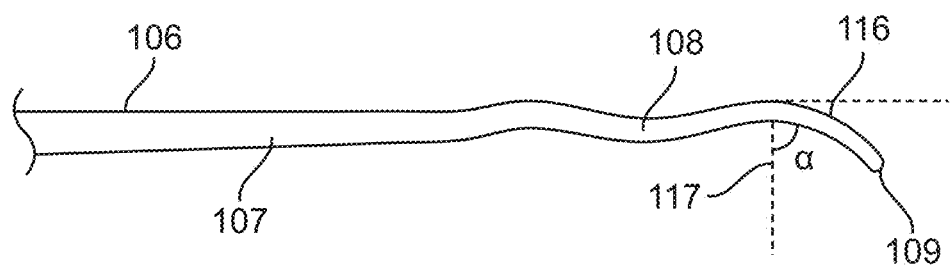
FIG. 19 shows probe insertion with J-angle flexible tip.

FIG. 19 shows an alternative probe 106 for insertion to bodily lumen with flexible portion 108 and preformed J-angle 117 near the distal tip 109. Curve 116 can facilitate the identification of a bodily lumen. Probe 106 can be made from nitinol, stainless steel, or other biocompatible materials or polymers.

Figure 20:
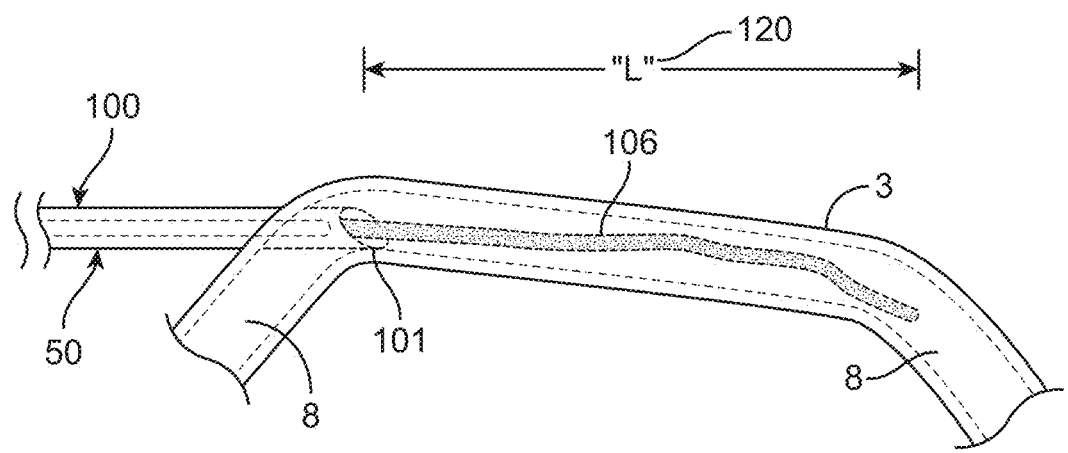
FIG. 20 shows probe translation for confirmation of intraluminal placement of the delivery system.

FIG. 20 illustrates probe 106 translation "L" where "L" 120 defines a length of advancement for probe 106 beyond the distal end opening of the delivery system 101. Achieving a predetermined threshold for "L" 120 advancement of the probe 106 indicates that the delivery system is within lumen 8 of the vas deferens 3. Threshold "L" 120 becomes the confirmation test of intraluminal placement of the delivery system 100. As depicted, delivery system 100 is within the lumen 8 of the vas deferens 3 since probe 106 was able to reach threshold "L" 120. Threshold "L" can be distance or length with a range of 2 cm to 12 cm with a 5 cm translation.

Figure 21:
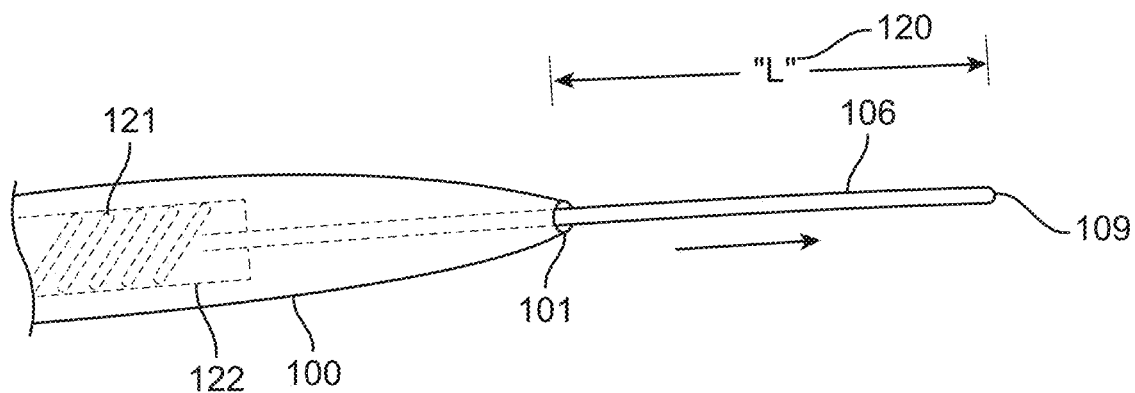
FIG. 21 shows a probe with a spring mechanism for translation and for confirmation of intraluminal placement.

FIG. 21 shows a probe 106 with spring mechanism 122 and spring 121 for providing a translation of probe 106 and for confirmation of intraluminal placement. Spring mechanism 122 is designed to advance probe 106 a predetermined distance "L" 120. Spring mechanism 122 can be triggered by the user and release latch (not shown).

Figure 22:
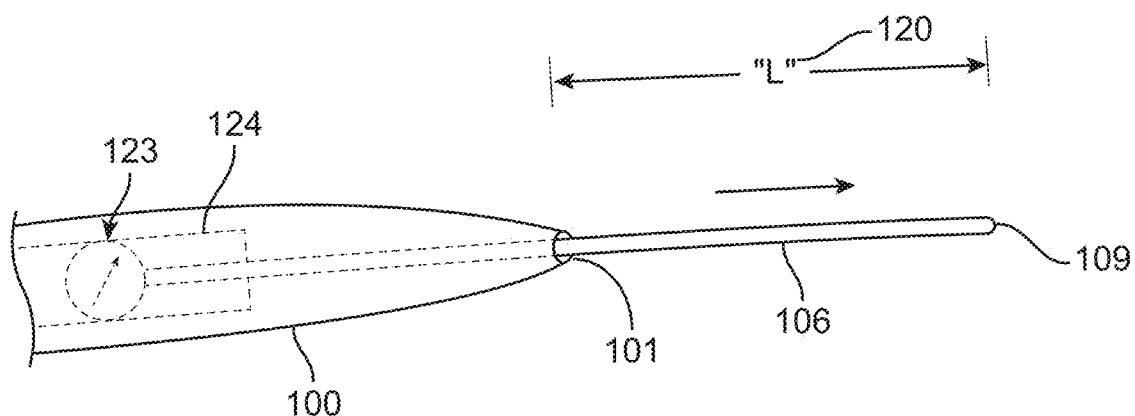
FIG. 22 shows a probe with deflection force measurement for intraluminal placement confirmation.

FIG. 22 shows an alternative probe 106 with deflection force measurement device 123 within a housing 124 of the delivery system 100. Upon advancement of probe 106, deflection force measurement device 123 records the amount of force, or limits the amount of force, required to advance probe 106 distance "L" 120. Achieving a force below a predetermined threshold for the advancement of the probe 106 at distance "L" 120 is used as a confirmation for intraluminal placement.

Figure 23A:
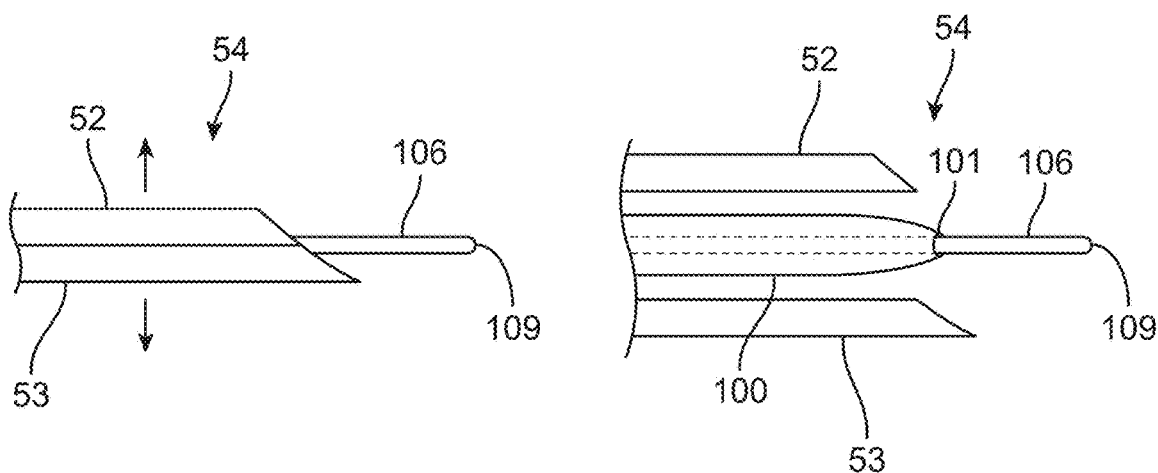
FIGS. 23A and B show methods for removing the sharp distal end of the insertion system before further manipulation in the bodily lumen.

FIGS. 23A and B illustrates that the sharp distal end of the insertion system can be removed before further manipulation in the bodily lumen. FIG. 23A shows a variation of a split needle system 54 with anterior portion 52 and posterior portion 53 that radially separate after probe 106 advancement and confirmation of intraluminal placement. Once separated, delivery sheath 100 with distal end 101 can be advanced over probe 106.

Figure 23B:
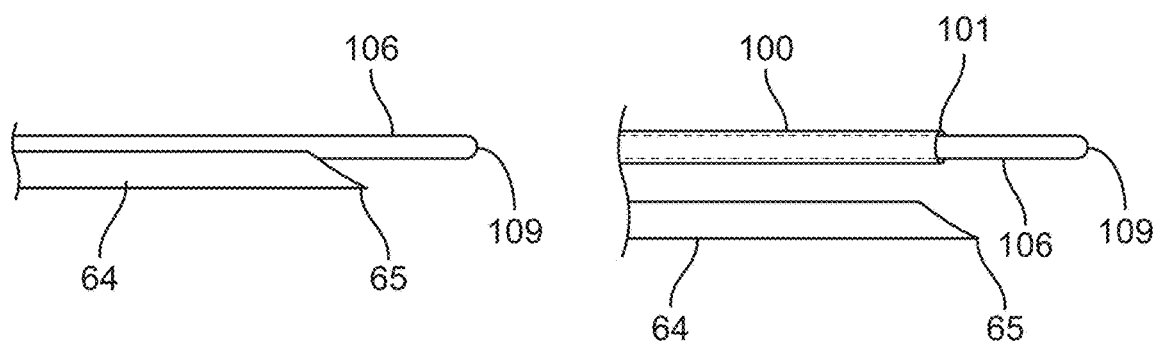
FIG. 23B shows half needle removal after confirmation of intraluminal placement.

FIG. 23B shows half needle 64 with distal end 65 at the time of insertion into a bodily lumen. After probe 106 advancement and confirmation of intraluminal placement, half needle can be retracted or withdrawn for advancement of the delivery sheath 100 over probe 106.

FIG. 24A to 24J show delivery sheath 100 placement. To confirm placement in the bodily lumen, the probe 106 can be advanced a distance "L" 120 into the bodily lumen to satisfy the translation requirement.

Figure 24A:
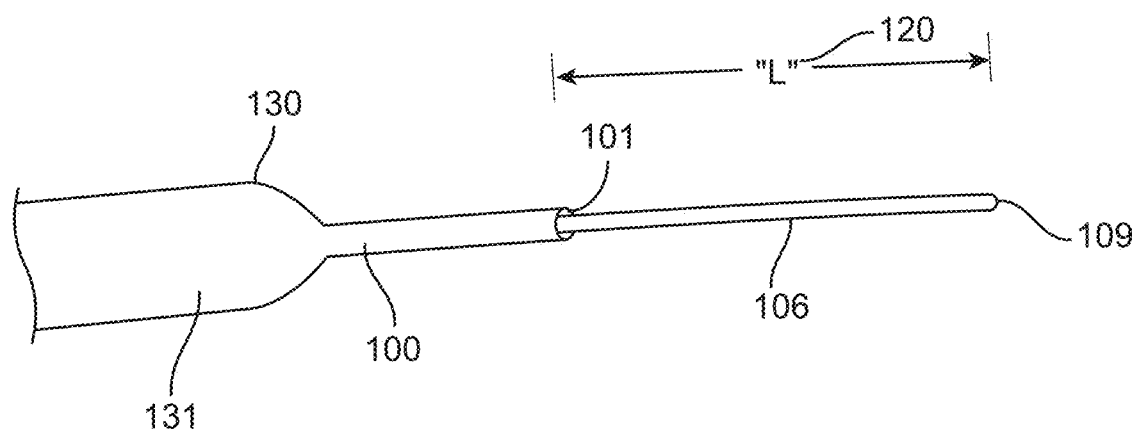
FIG. 24A to 24J show placement of delivery sheath over the probe into the bodily lumen.
Figure 24B:
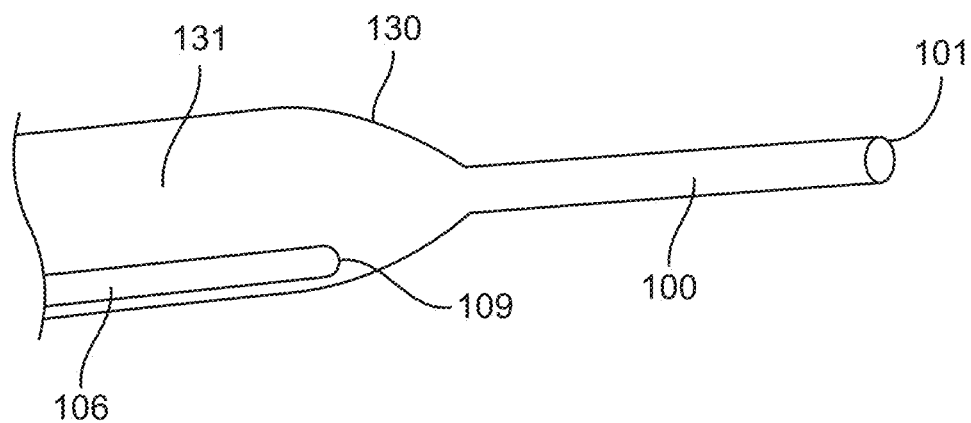

FIG. 24B illustrates the retraction of the probe 106 back into handle 131 and proximal to nose cone 130. Retraction of probe 106 into nose cone 130 drops the distal end of probe 109 to a location below the central axis of the delivery sheath 100 and provides an obstructed central lumen.

Figure 24C:
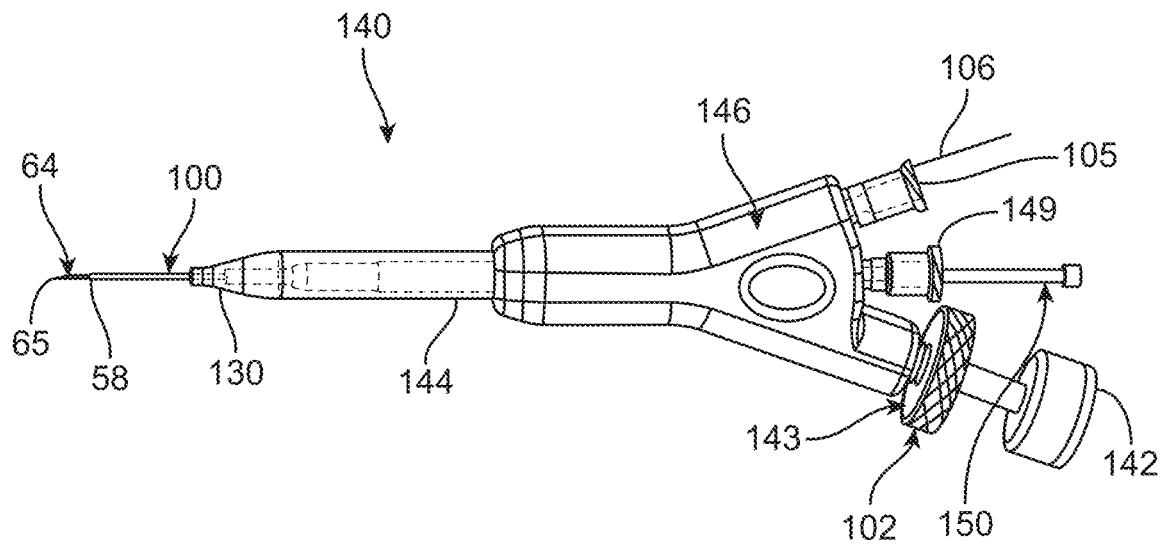
Figure 24C:
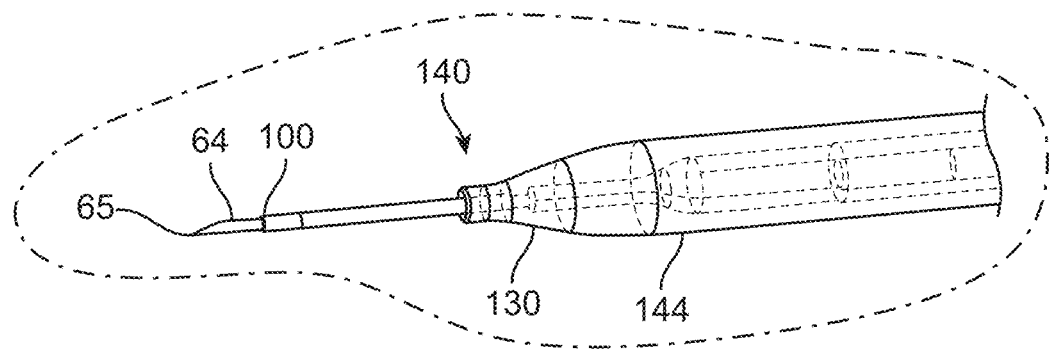

FIG. 24C shows that a three-lumen delivery system 140 can have a penetrating half needle 64, access sheath 100, nose cone 130, handle 146, guidewire port 105 with probe 106, cartridge port 149 with cartridge with hydrogel 150, penetrating half needle handle 102 with penetration adjustment 143, and half needle removal hub 142.

Within the dashed lines oval is a close-up illustration of the distal end of three-lumen delivery system 140 with half needle 64 and distal tip 65 within access sheath 100. Within housing 144 in a transparent view, nose cone 130 terminates at the proximal opening of access sheath 100. Half needle 64 could be sized as one-half a 21 G needle but other sizes are possible including 22 G, 23 G, 24 G, or smaller.

Figure 24D:
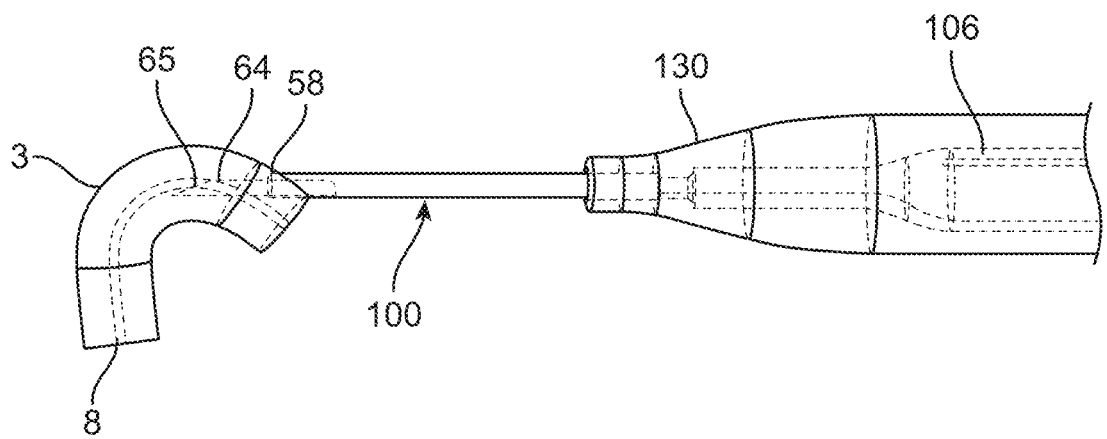
Figure 24D:
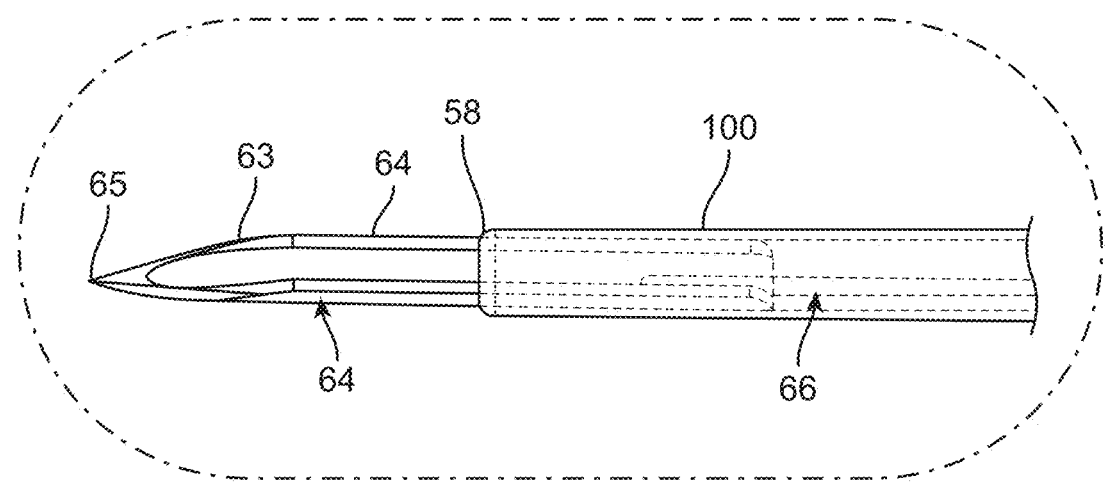
Figure 24D:
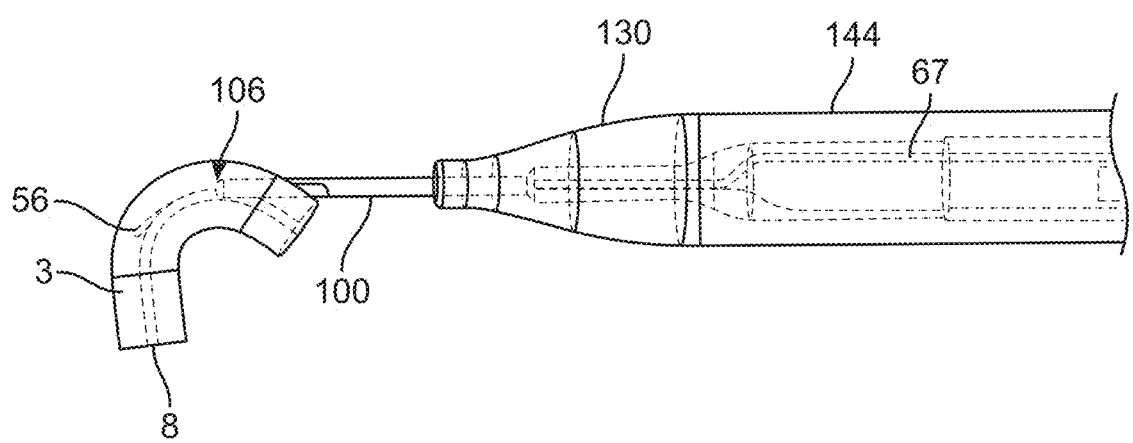
Figure 24D:
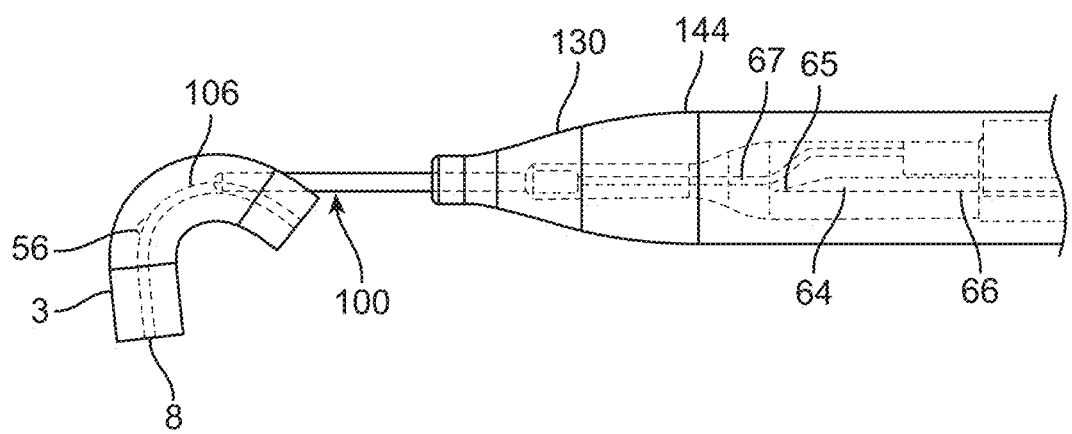
Figure 24D:
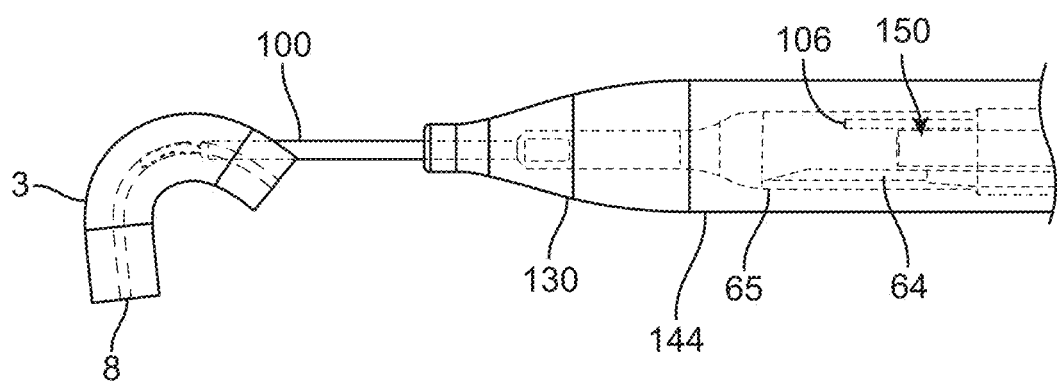

FIG. 24D illustrates the steps of placing the three-lumen delivery system within the vas deferens. STEP 1: Device half needle is advanced in vas deferens illustration shows half needle 64 entering lumen 8 of vas deferens 3.

Dashed lines oval shows close-up view of half needle 64 with distal tip 65 and distal bevel 63. Half needle 64 is positioned within access sheath 100 and protrudes beyond distal end opening 58 of access sheath 100. Half needle 64 is retracted or advanced within access sheath 100 by half needle pull wire 66.

STEP 2: Guidewire can be advanced into vas deferens illustration shows guidewire or probe 106 entering lumen 8 of vas deferens 3. Probe 106 is advanced or retracted by probe pull wire 67 through housing 144 and nose cone 130 into access sheath 100.

STEP 3: Half needle can be retracted, and the sheath is advanced illustration shows half needle retracted into housing 144 with access sheath 100 advanced over probe 106 into lumen 8.

STEP 4: Half needle and guidewire can be completely retracted illustration shows both the half needle 64 and guidewire or probe 106 retracted into housing 144.

STEP 5: Plunger can be advanced through cartridge and hydrogel is inserted into vas (hydrogel injection not shown).

Figure 24E:
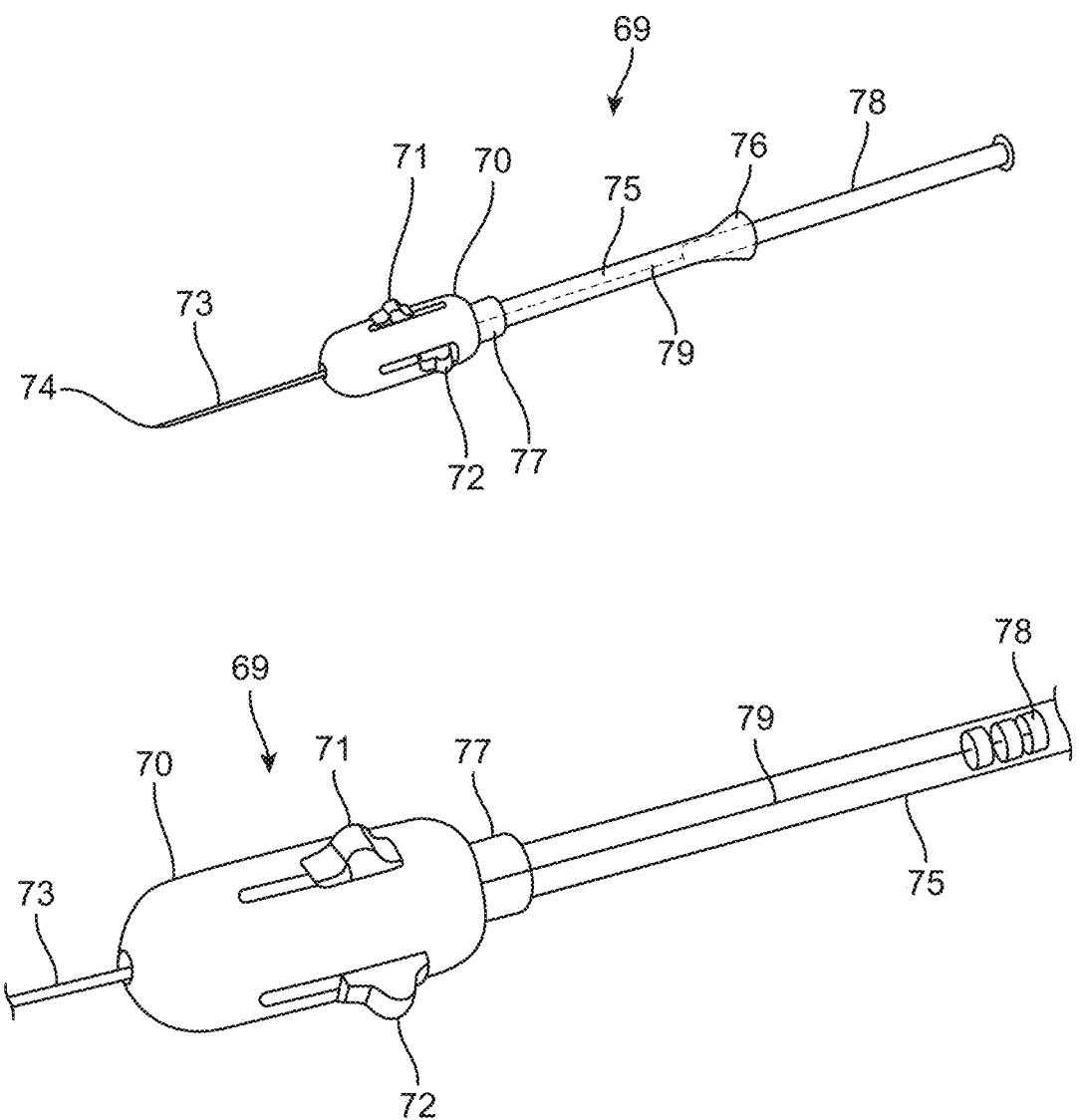

FIG. 24E shows another handle configuration of a three-lumen delivery system 69 with slide handle housing 70. Trocar slide button 71 advances and retracts half needle with access sheath 73. Guidewire slide button 72 advances and retracts probe (not shown) through access sheath 73. Central lumen contains cartridge connector 77 with cartridge holder 75 which contains hydrogel (not shown). On the proximal end, plunger 78 advances plunger push rod 79 to eject hydrogel from cartridge holder 75.

Figure 24F:
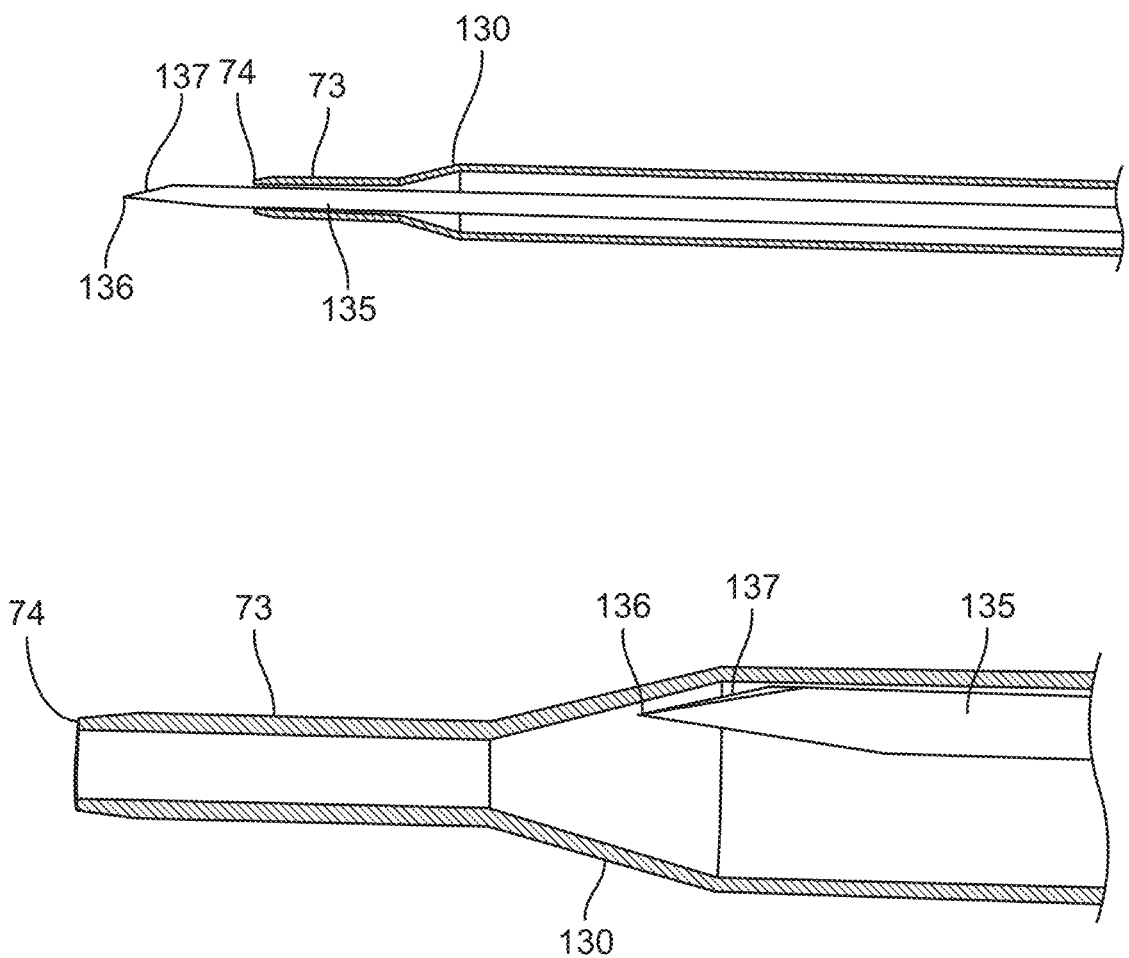

FIG. 24F in a cross-sectional view shows a variation for removing a trocar 135 with sharp distal tip 136 and bevel 137 from the central lumen of access sheath 73 prior to delivery of a probe (not shown). Top view shows trocar 135 advanced beyond the distal end opening 74 of access sheath 73. Bottom view shows trocar 135 retracted into nose cone 130 with trocar tip 136 housed above central lumen of access sheath 73.

Figure 24G:
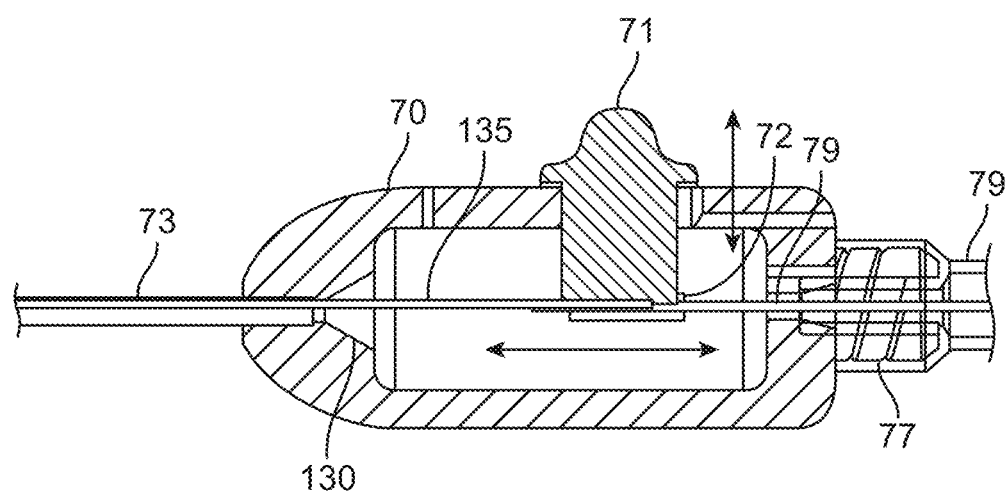

FIG. 24G illustrates a handle slide for advancing and retracting trocar 135 within housing 70. Slide button 71 is attached to trocar 135 and can provide movement both horizontally and vertically by spring loading (not shown).

Figure 24H:
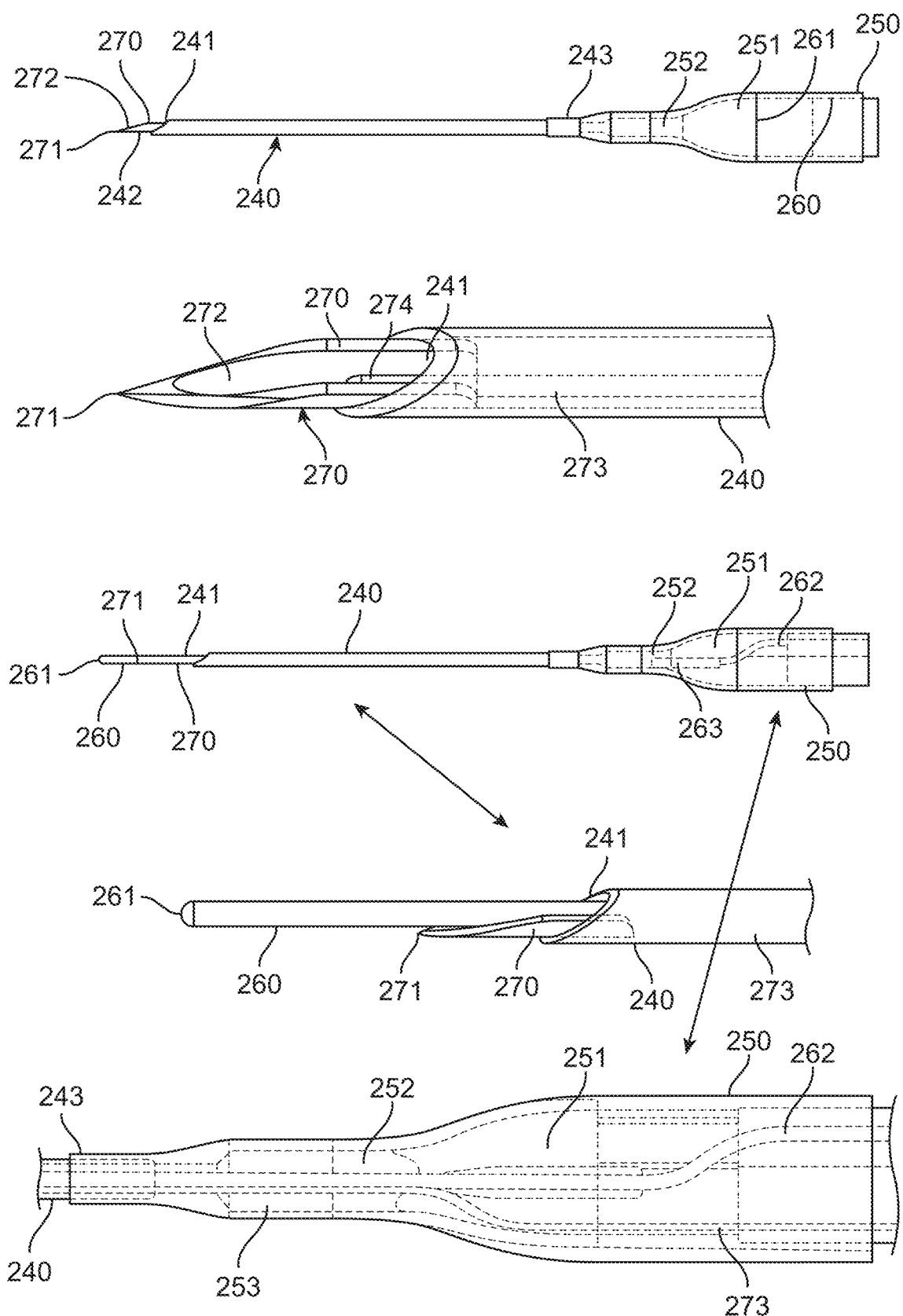
Figure 24H:
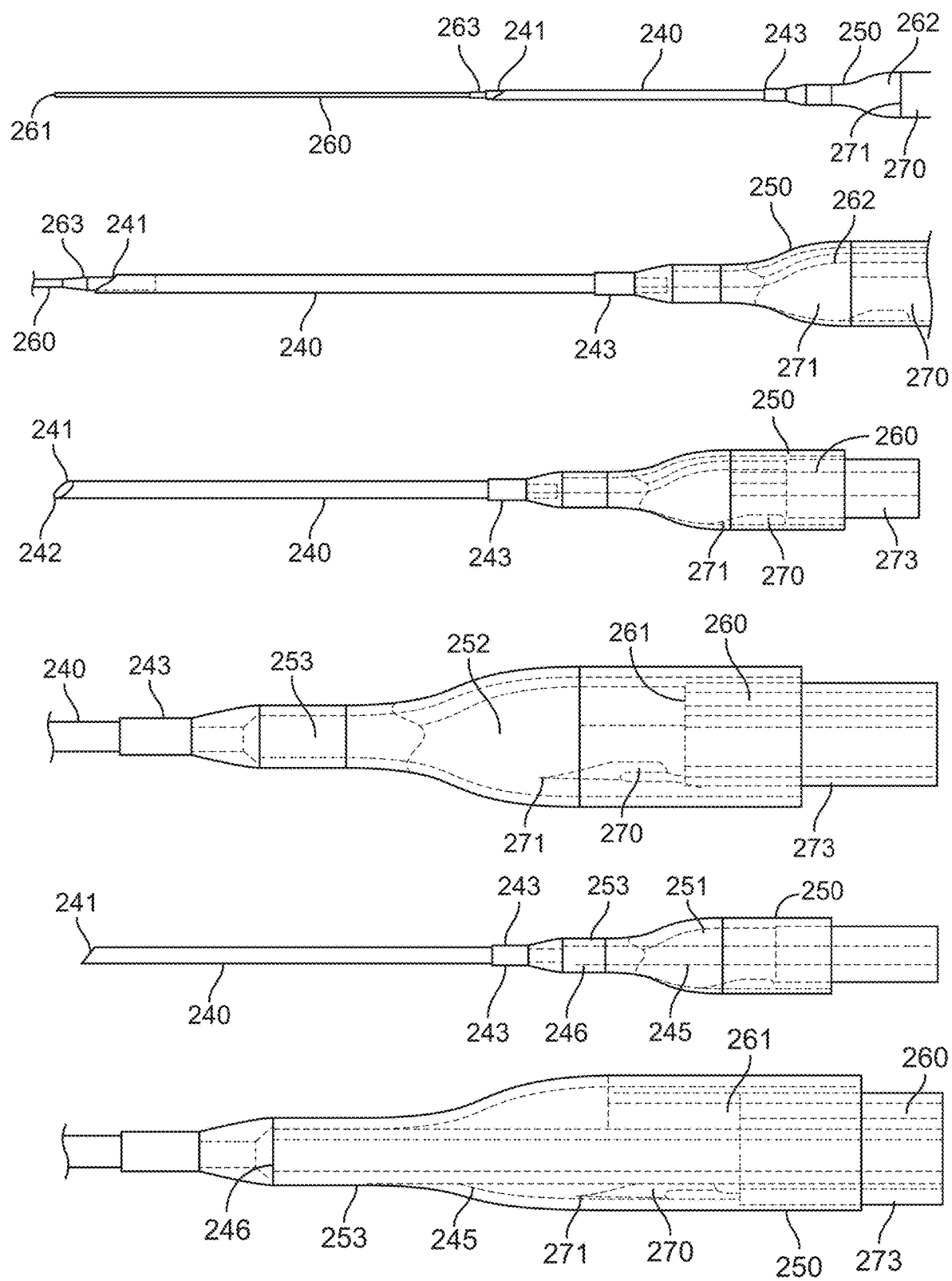
Figure 24H:
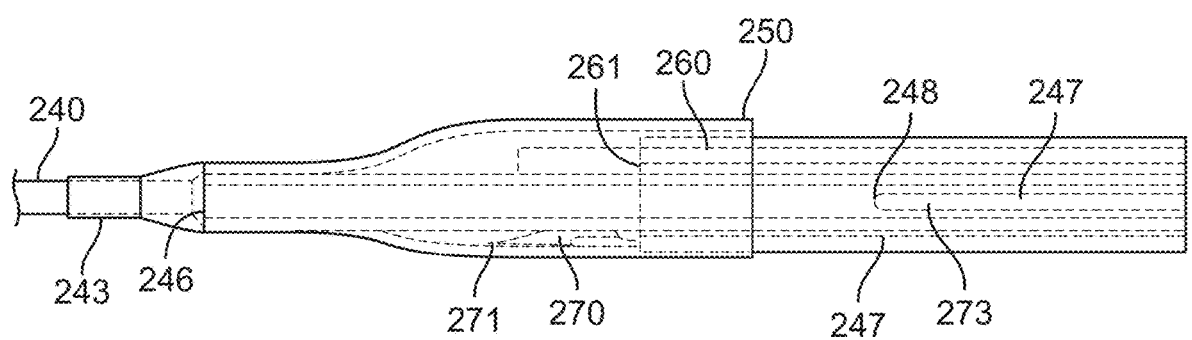

FIG. 24H illustrates the steps of delivery of the probe and hydrogel into the vas deferens with the delivery system.

STEP 1: Device ready to advance into vas deferens illustration shows half needle 270 with access sheath 240 and half needle pull wire 273. Top view shows the position of the half needle 270 and connection with three-lumen housing 250. Bottom view shows close-up view of the distal tip 271 of half needle 270 protruding beyond distal opening 241 of access sheath 240. Half needle pull wire 273 is attached to half needle 270.

STEP 2: Tapered guidewire can be advanced into vas deferens illustration shows guidewire or probe 260 advanced beyond the distal tip 271 of half needle 270. Top views show the relation of probe 260, half needle 270, and access sheath 240. The bottom view shows in cross-section probe pull wire 262 attached to probe 260, and half needle pull wire 273 within housing 250.

STEP 3: Needle can be retracted, and guidewire is advanced illustrations show in the top view the guidewire or probe 260 advanced beyond access sheath 240. The bottom view in cross-section shows the half needle distal tip 271 and half needle 270 retracted with housing 250.

STEP 4: Needle and guidewire are completely retracted and clear of the central lumen illustrations shows access sheath 240 and both the half needle 270 and probe 260 retracted and inside housing 250. Bottom view in cross-section shows transition piece or nose cone 253 clear of both the half needle 270 and probe 260 after being retracted from the access sheath 240.

STEP 5: Cartridge is advanced to the mating feature in the transition piece to provide the hydrogel into the bodily lumen. Cartridge 245 is placed within the central lumen of housing 250, through nose cone 252, and couples with the cartridge docking area 253. Bottom image shows a cross-sectional rendering of cartridge 245 and the relationship of probe 260 and half needle 270 within housing 250.

STEP 6: Plunger can be advanced through cartridge and hydrogel is inserted into vas deferens is shown in a cross-sectional image with plunger 247 pushing the hydrogel (not shown) through cartridge 245. Distal end of plunger 248 with traverse distal end opening of the cartridge 246 and through access sheath 240 to expel hydrogel in the vas deferens (not shown) or bodily lumen.

Figure 24I:
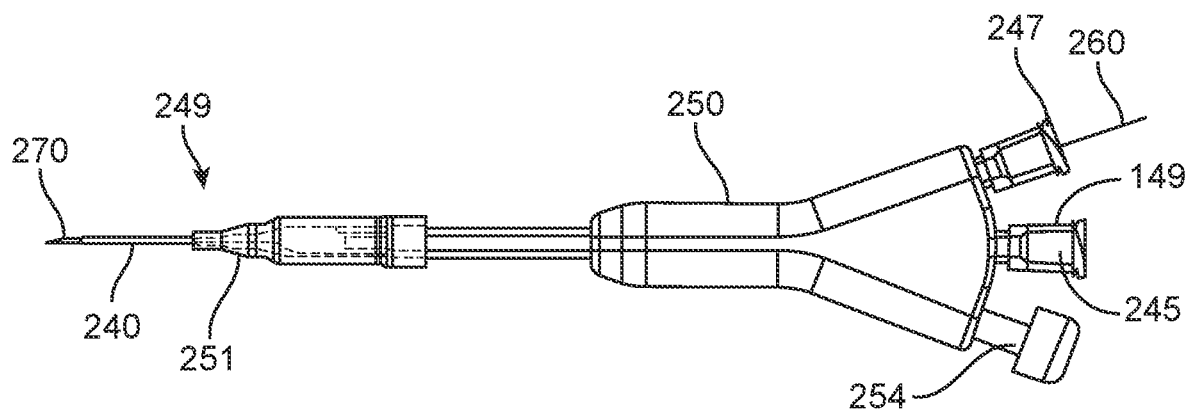

FIG. 24I shows a variation of the three-lumen delivery system 249. Illustration identifies half needle 270 protruding from access sheath 240 connected to three-lumen housing 250. Proximal end has irrigation connector 247 and probe 260, cartridge port 149 and cartridge with hydrogel 245, and D-shaped needle handle 254 for advancing and retracting half needle 270.

Figure 24J:
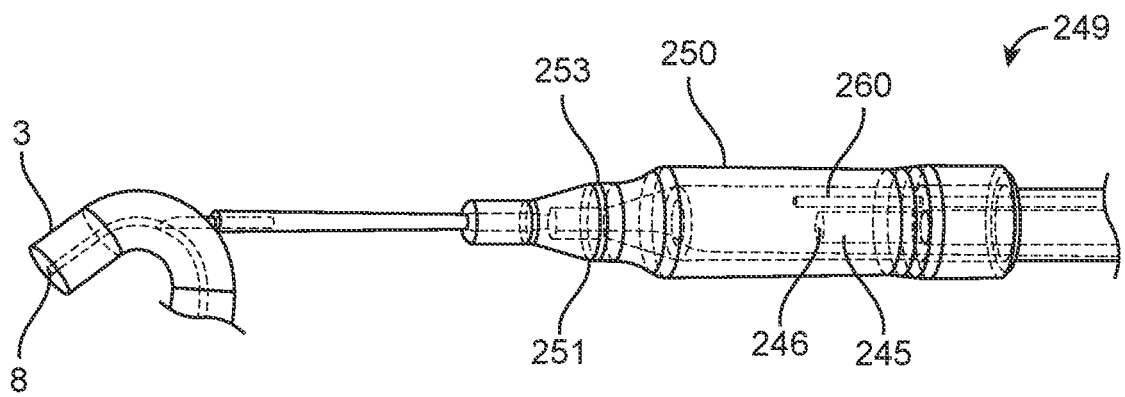
Figure 24J:
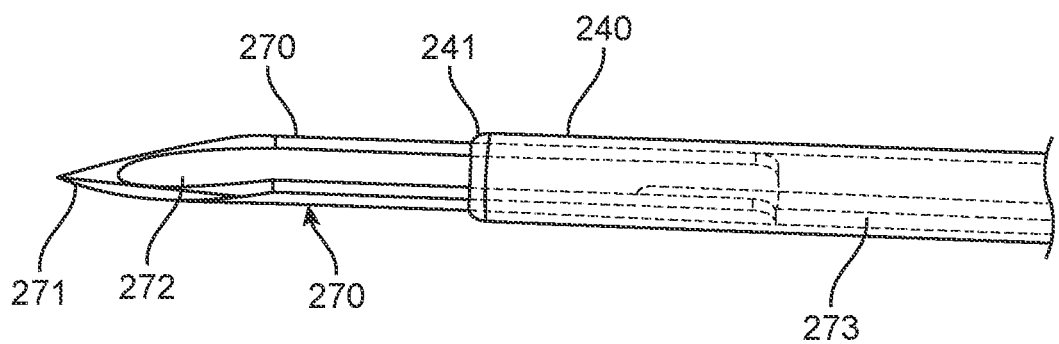
Figure 24J:
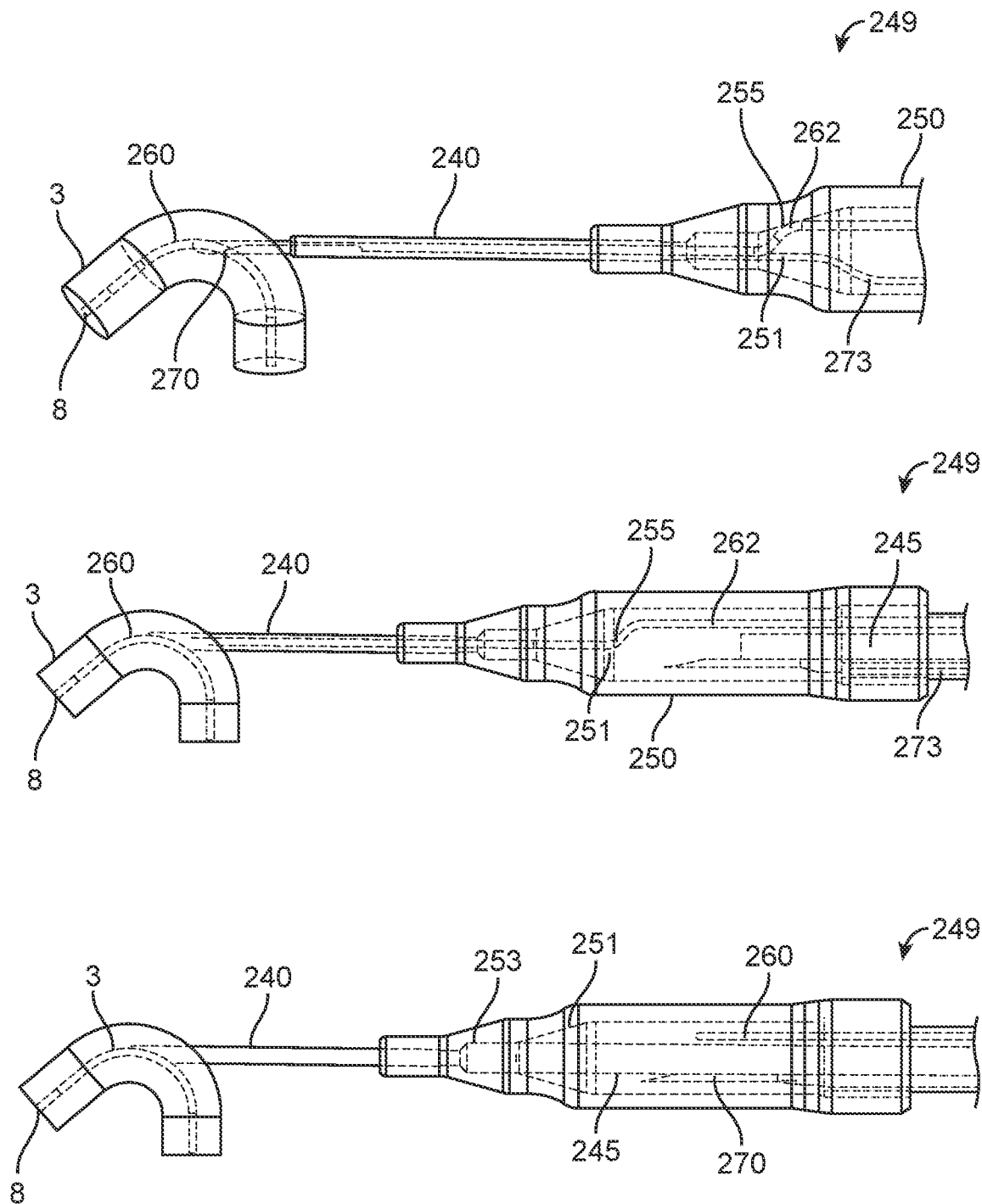
Figure 24J:
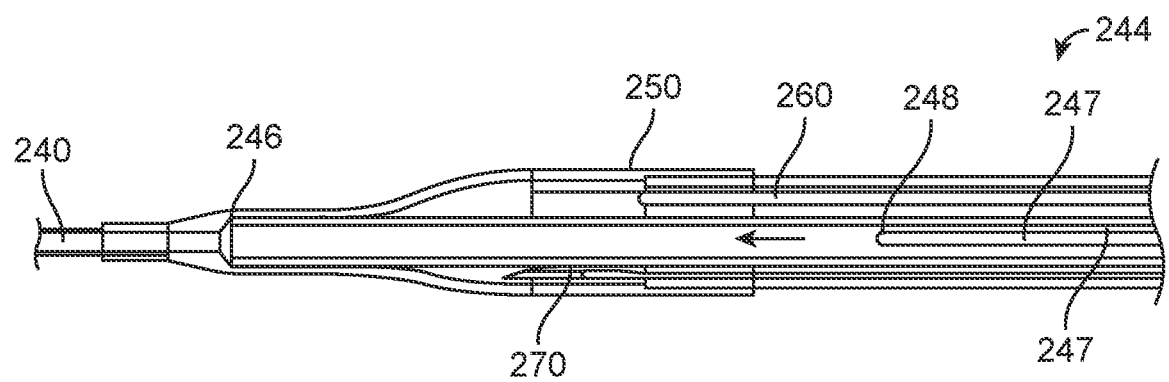

FIG. 24J illustrates a variation of placing the three-lumen delivery system 249 and hydrogel into the vas deferens or a bodily lumen.

STEP 1: Device ready to advance into vas deferens with half needle 270 entering vas deferens 3 and lumen 8. Bottom view is a cross-sectional image of half needle 270 and attachment to half needle pull wire 273 within access sheath 240.

STEP 2: Guidewire can be advanced into vas deferens illustrates the advancement of guidewire or probe 260 into lumen 8 of vas deferens 3. Pull wire latch release 255 provides the positive opening for cartridge 245 (shown in the next step). Pull wire latch release 255 is a lock-out that prevents the cartridge from being deployed. In practice, cartridge deployment and hydrogel delivery can only occur once the translation of probe 260 is satisfied.

STEP 3: Needle can be retracted and the sheath is advanced illustrates access sheath 240 being pushed over probe 260 with half needle 270 retracted into three-lumen housing 250. The advancement of probe 260 within lumen 8 opens central lumen within housing 250 by the pull wire latch release 255 reaching the required distance.

STEPS 4 & 5: Needle and guidewire are completely retracted and the cartridge is advanced is illustrated with both the probe 260 and half needle 270 retracted into housing 250 with access sheath 240 remaining into lumen 8. Cartridge 245 is coupled into cartridge docking area 253.

STEP 6: Plunger can be advanced through cartridge and hydrogel is inserted into vas is illustrated with cartridge 245 placed within the cartridge docking area 253 with plunger 247 advancing through the central lumen and into the access sheath 240. Hydrogel is not shown.

Figure 25A:
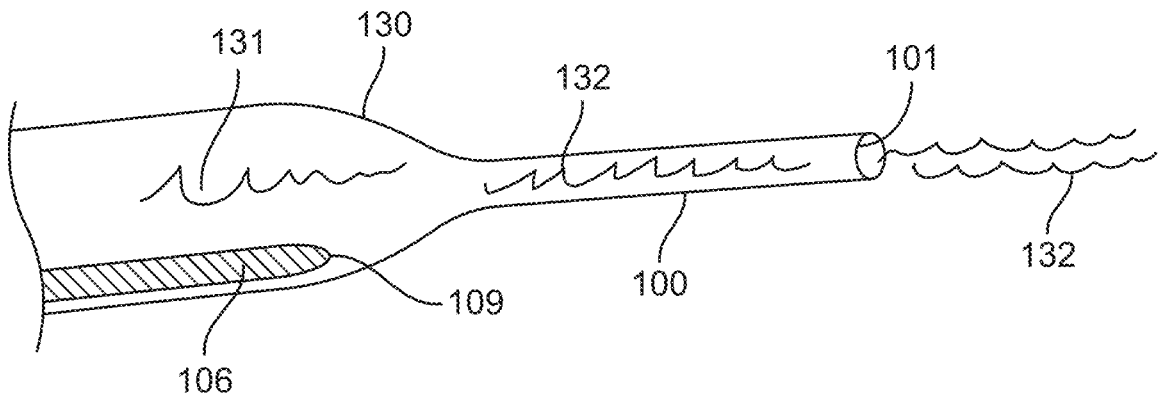
FIGS. 25A to B show variations for preparing the bodily lumen for hydrogel delivery.
Figure 25B:
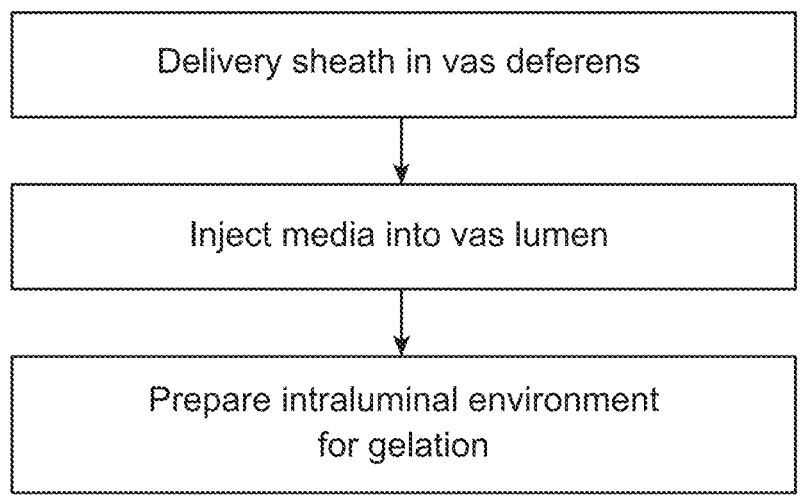

FIGS. 25A to B illustrates a variation for preparing the bodily lumen for hydrogel delivery. FIG. 25A shows the injection of media 132 for clearing the bodily lumen (not shown) of material and preparing for hydrogel insertion after delivery sheath 100 insertion.

FIG. 25B shows a variation for injection of media for assisting in the gelation of the hydrogel after delivery sheath insertion.

STEP 1: Delivery sheath in vas deferens.

STEP 2: Inject media into vas lumen. Media can be phosphate buffered saline, saline, Ringer's lactate or other biocompatible fluid with a pH or property that opens the lumen, wets or changes the lubricity, affects the pH, or washes away materials in the lumen of the vas deferens. Media can be a gas. Injection of media can be pressure regulated, flow rate regulated, or volume controlled.

STEP 3: Prepare intraluminal environment for gelation of the hydrogel. After the injection of media, the intraluminal environment can be uniform in terms of lubricity, pH, or without remnant sperm and proteins.

Figure 26:
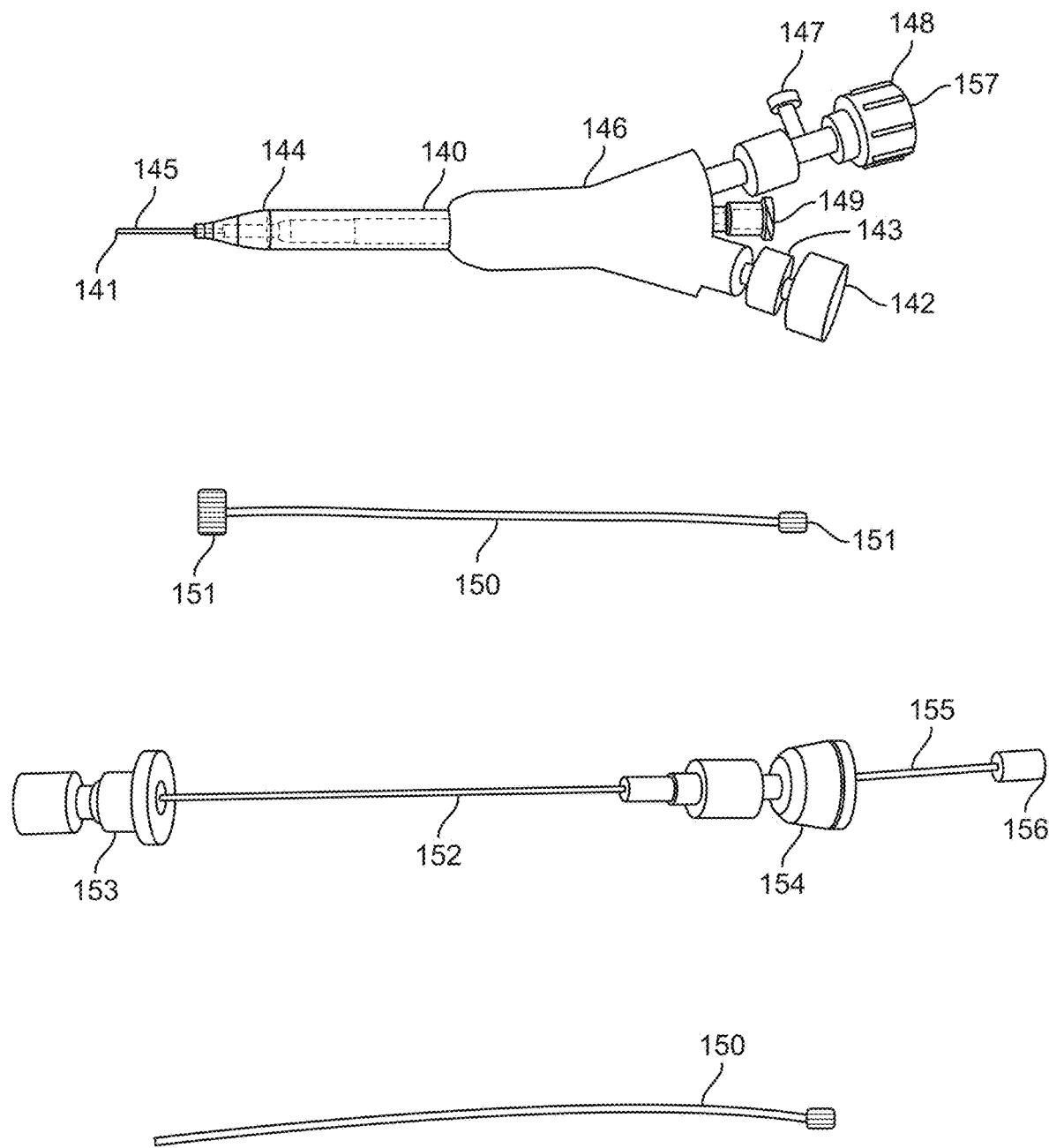
FIG. 26 shows variations for the delivery of the hydrogel using a hydrogel cartridge with plunger.

FIG. 26 shows a variation for the delivery of the hydrogel (not shown) using a hydrogel cartridge 150 with plunger 152. Top image shows the components of the delivery system 146 with access sheath 141, probe Touhy connector 148 with probe opening 157 and irrigation flush port 147. Proximal end shows cartridge port 149, half needle removal hub 142, and half needle depth of penetration control 143. Cartridge 150 contains hydrogel and has cartridge caps 151 on both ends. Plunger 152 has push rod connector 153, push rod hub 154, distal mini push rod 155 and distal mini push rod hub 156. Bottom image shows cartridge 150. Mini push rod 155 is configured to pass through access sheath 141 in the delivery of the hydrogel.

Figure 27:
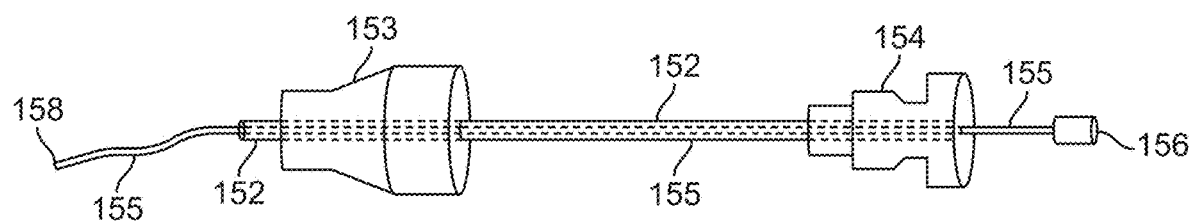
FIG. 27 shows a hydrogel cartridge with flexible tip plunger.

FIG. 27 shows a hydrogel cartridge with an alternative plunger 152 with distal mini push rod 155 and mini push rod flexible tip 158. Mini flexible tip 158 is configured to adapt to the curvature of the vas deferens or bodily lumen during delivery of the hydrogel.

Figure 28:
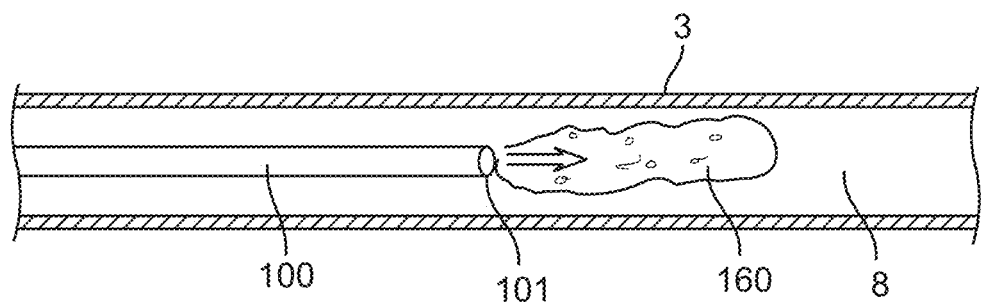
FIG. 28 illustrates antegrade delivery of the hydrogel in the vas deferens.

FIG. 28 illustrates in a cross-sectional view antegrade delivery with an access sheath 100 placed within the lumen 8 of vas deferens 3 and injecting hydrogel 160 within the lumen 8.

Figure 29:
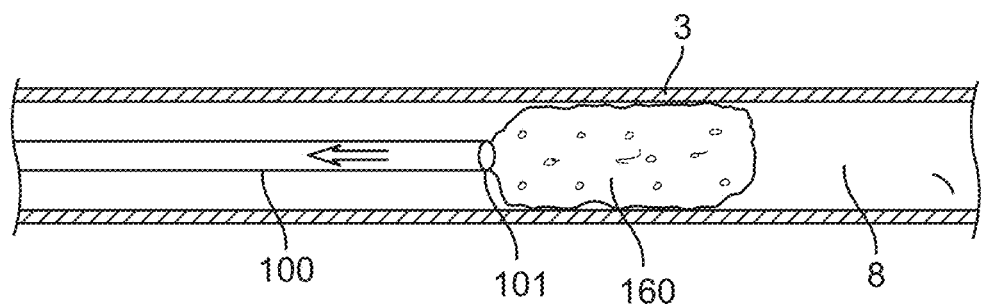
FIG. 29 illustrates a variation configured to provide retrograde delivery of the hydrogel in the vas deferens with simultaneous retraction of the delivery sheath.

FIG. 29 illustrates in a cross-sectional view retrograde delivery of the hydrogel 160 within the lumen 8 of the vas deferens 3. During this delivery, the ejection of hydrogel 160 occurs simultaneous with the retraction of access sheath 100.

Figure 30A:
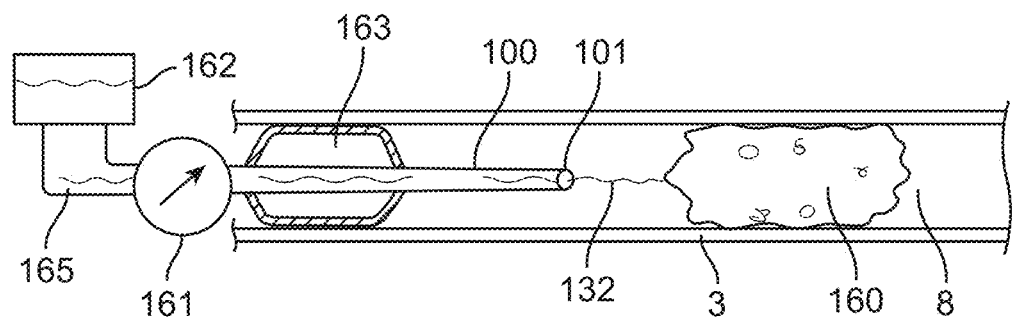
FIGS. 30A and B show variations for confirming occlusion of the bodily lumen after hydrogel delivery and removal of the system from the bodily lumen.

FIGS. 30A and B show a variation for confirming occlusion of the bodily lumen after hydrogel delivery and removal of the system from the bodily lumen. FIG. 30A shows the injection of media, gas, or air for confirming occlusion using a force measurement system 161. The injection of media can also be used for initiating gelation of the hydrogel. In practice, media supply 162 is connected to the media force measurement device 161 via media conduit 165 and is connected to access sheath within lumen 8 of vas deferens 3. Media 132 is instilled through distal end opening 101 and meets occlusive device or hydrogel 160. Access sheath 100 can have proximal occlusion balloon 163 (balloon lumen and balloon inflation device not shown) to prevent media pressure from passing retrograde of the system.

Figure 30B:
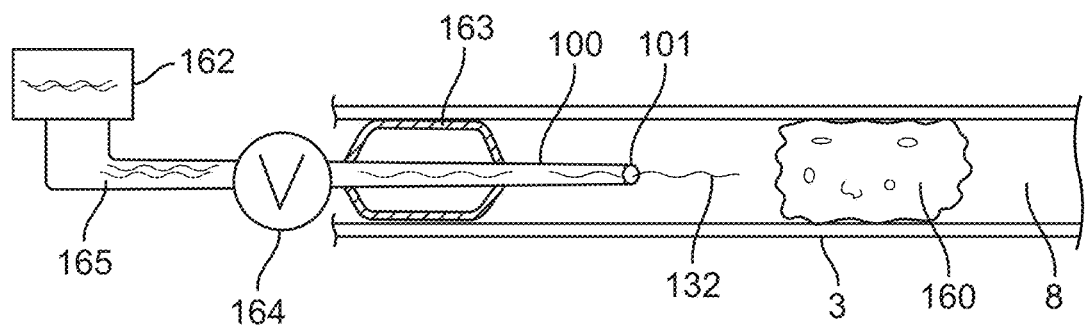
FIG. 30B shows injection of media for confirming occlusion using volume measurement system.

FIG. 30B shows injection of media for confirming occlusion using a volume measurement device 164 within a similar configuration as the media force measurement system. In practice, a predetermined volume is instilled into the lumen 8 of the vas deferens 3 to determine when a threshold volume of media can be delivered into lumen 8 within the space from the access sheath 100 and occlusive device or hydrogel 160. Access sheath 100 can have a proximal occlusion balloon 163 (balloon lumen and balloon inflation device not shown) to prevent media flow in the retrograde direction.

Figure 31:
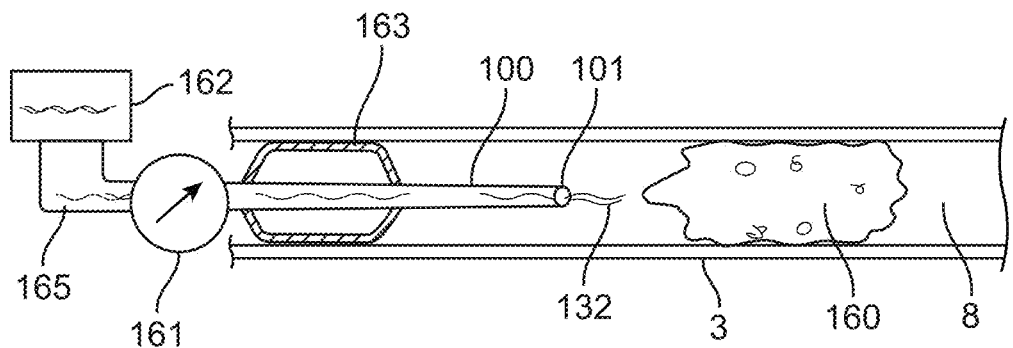
FIG. 31 shows the injection of media for creating space from bodily lumen insertion site and preventing a tail of hydrogel from exiting the vas deferens.

FIG. 31 shows a variation with the injection of media 132 for creating space in the lumen 8 from the distal end opening of the access sheath 101 the occlusive device or hydrogel 160 with the intention of preventing a back flow, tail, or remnant hydrogel from exiting the vas deferens 3. In practice immediately after, or near the final injection of hydrogel, media 132 is injected to prevent the back flow, tail, or remnant hydrogel from flowing in a retrograde direction.

Figure 32:
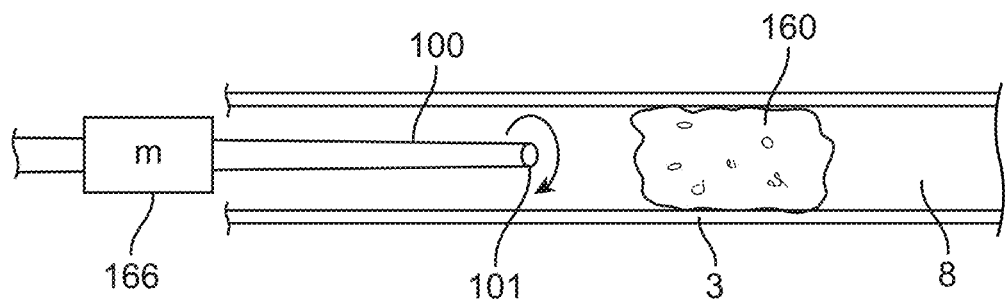
FIG. 32 shows the removal of the delivery sheath with simultaneous rotation of sheath to prevent a tail of hydrogel from exiting the vas deferens.

FIG. 32 shows a technique for the removal of the delivery or access sheath 100 after the injection of hydrogel 160 with simultaneous rotation of access sheath 100 around its central axis during the injection of the hydrogel, and removal of the access sheath 100, to prevent a tail of hydrogel 160 from exiting the vas deferens 3. Rotational motor 166 at the proximal end of access sheath 100 facilitates uniform and constant rotation of the access sheath 100. Conversely, rotational motor 166 can be employed during just the removal of access sheath 100 from the vas deferens 8. Alternatively, rotational motor 166 can be replaced by non-motorized gearing (not shown) that automatically rotates the access sheath 100 during withdrawal. Alternatively, the user can manually rotate the access sheath during removal.

Figure 33A:
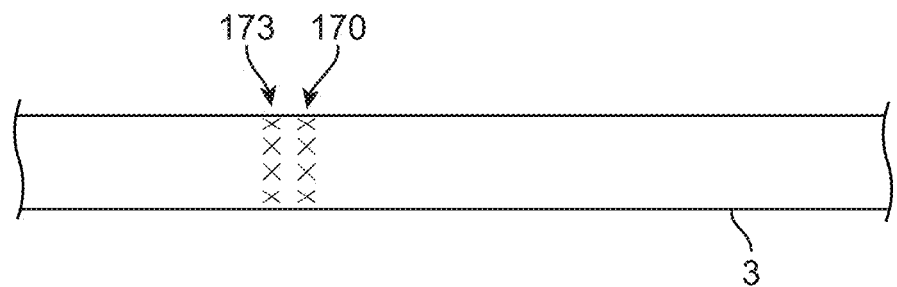
FIGS. 33A to C show systems for future identification of the delivery site of the occlusive hydrogel in the bodily lumen.
Figure 33B:
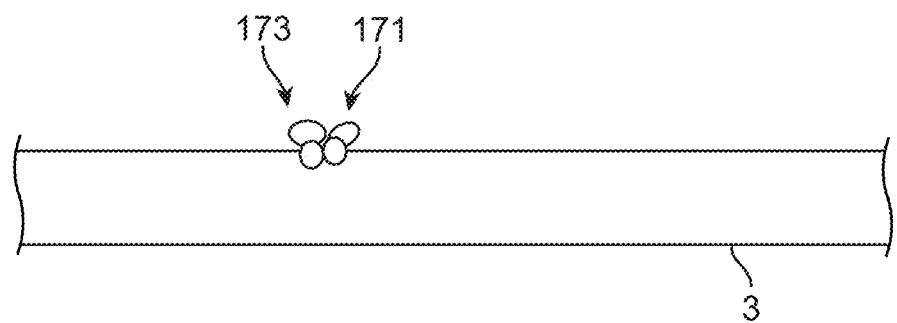
Figure 33C:
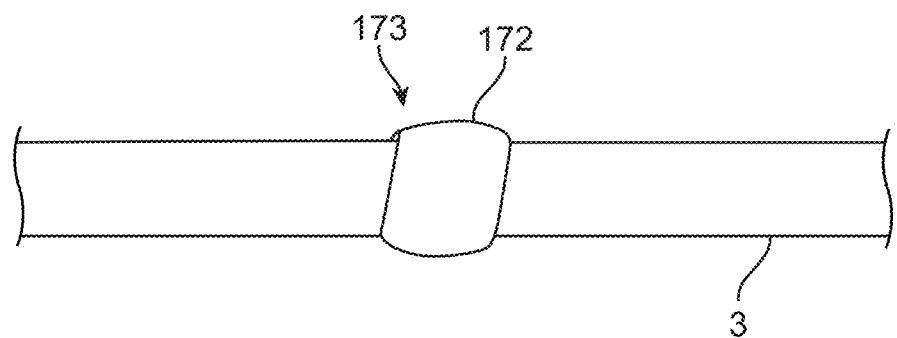

FIGS. 33A to C show systems for future identification of the delivery site 173 of the occlusive hydrogel in the bodily lumen or vas deferens 3. FIG. 33A shows a system where the delivery site 173 of insertion into the vas deferens 3 can be tagged with a visual tattoo 170 on the external surface of the vas deferens 3.

FIG. 33B shows a system for future identification of the delivery site 173 of the occlusive hydrogel in the bodily lumen or vas deferens 3 where the site of insertion into the vas deferens 3 can be tagged with an external clip 171 that is also visible via ultrasound or radiographic imaging. The external clip 171 does not occlude the vas deferens 3, but only marks the delivery site 173 of insertion that can be identified in the future.

FIG. 33C shows a system for future identification of the delivery site 173 of the occlusive hydrogel in the bodily lumen or vas deferens 3 where the site of insertion into the vas deferens 3 can be tagged with a circumferential band 172 to permanently identify the site of insertion. The circumferential band 172 is slightly elastomeric and is not restrictive or compressive enough to occlude the vas deferens 3 and or restrictive enough to not create tissue necrosis.

Figure 34A:
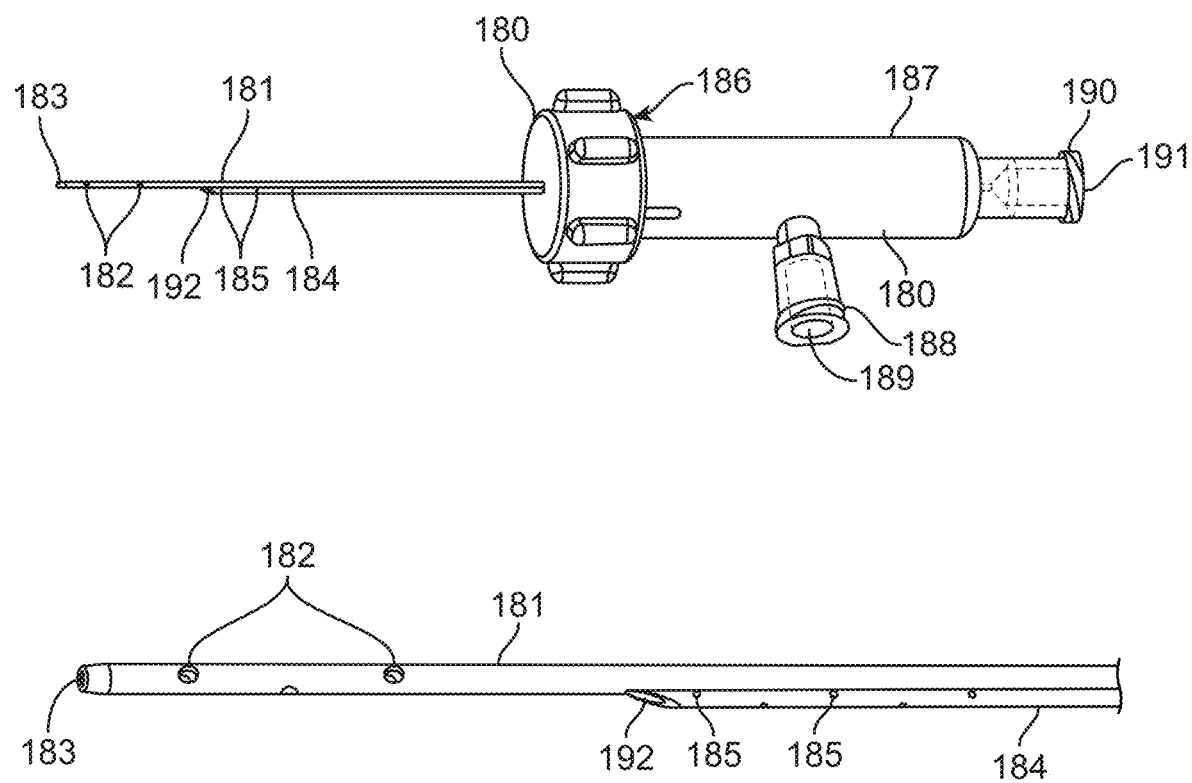
FIGS. 34A to 34D show variations for a duel lumen removal system with rotating handle for the removal of a hydrogel occlusion from a bodily lumen with an intraluminal sheath, termed the removal sheath, a rotating knob, and can be configured the same as the previously described delivery sheath.

FIGS. 34A to 34D show a dual lumen removal system with rotating handle 180 of a hydrogel or occlusive device from a bodily lumen with an intraluminal removal sheath 179, a rotating knob 186, and can be configured in a similar fashion with a probe and requires translation "L" as confirmation of intraluminal access as previously described with the delivery sheath. FIG. 34A illustrates the removal system 180 with irrigation holes 182 in the wall of irrigation lumen 181 and aspiration holes 185 in aspiration lumen 184. Irrigation lumen 181 is connected to an irrigation connector 190 with irrigation connector opening 191 for the instillation of media such as sodium bicarbonate solution or other media that affect, dissolve, break cross-links, change the pH or properties of the occlusive device or hydrogel for removal from the bodily lumen. Irrigation or media source is not shown. Media can exit the irrigation lumen 181 from irrigation holes 182 and distal end opening of the irrigation lumen 183. Aspiration lumen 184 is connected to vacuum port 188 and vacuum port opening 189 for the application of negative pressure within the bodily lumen to remove excess media and loose portions of the occlusive device or hydrogel. Vacuum source is not shown. Bottom image shows irrigation lumen 181 with irrigation holes 182 and aspiration lumen 184 with distal end opening of aspiration lumen 192 and additional aspiration holes 185. For both irrigation and aspiration, the number of lumen holes can be expanded or reduced.

Figure 34B:
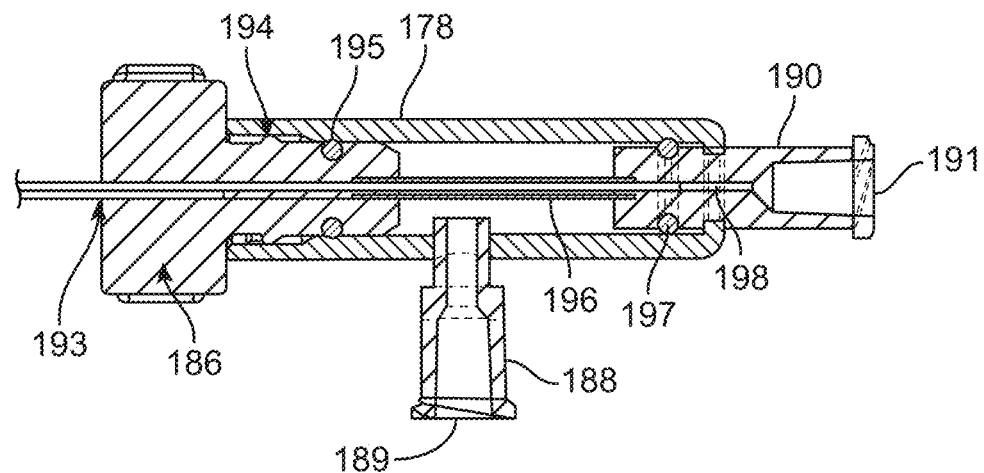

FIG. 34B shows the dual lumen removal system 180 with dual lumen rotating removal system handle 178 with rotating seals 195 and 197, vacuum port 188, and irrigation port 190. Dual lumen rotating removal system handle 178 allows for the concurrent application of irrigation of media and aspiration of excess media and dissolved hydrogel from the bodily lumen during the removal process.

Figure 34C:
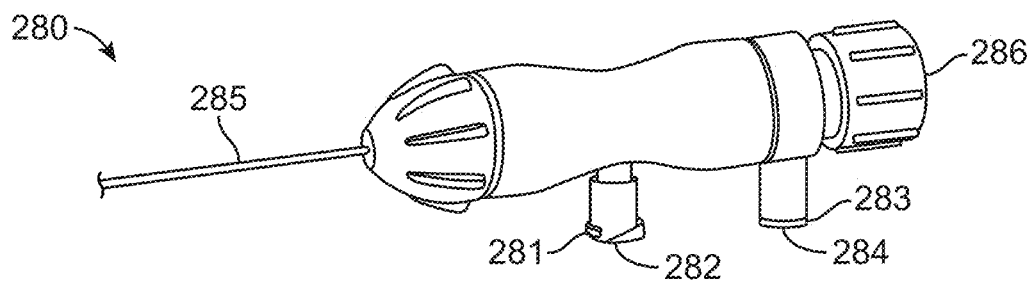
Figure 34C:
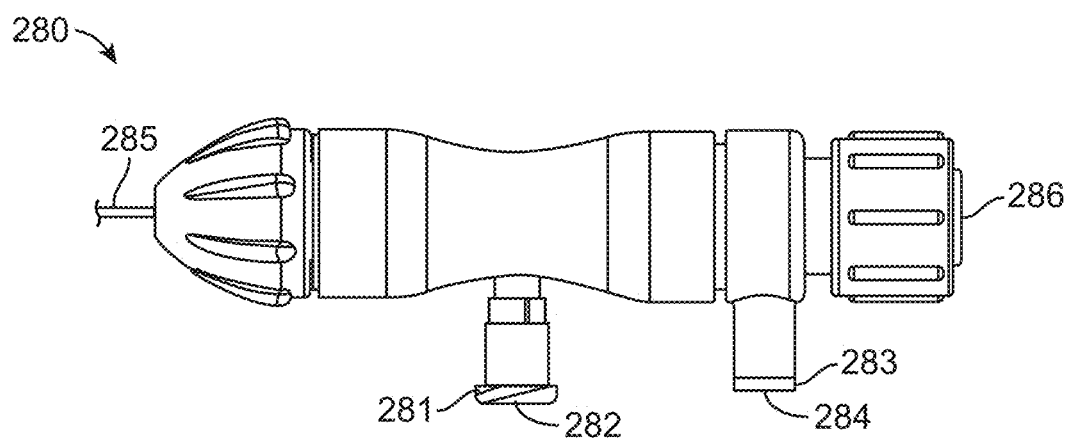

FIG. 34C shows two views of the dual lumen removal system with rotating handle 280, aspiration port 281, aspiration opening 282, irrigation port 283, irrigation opening 284, and proximal end opening 286. Dual lumen sheath 285 is connected to dual lumen removal system with rotating handle 280 with central lumen (not shown) connected to guidewire or probe port 286 on the proximal for the placement of a probe (not shown).

Figure 34D:
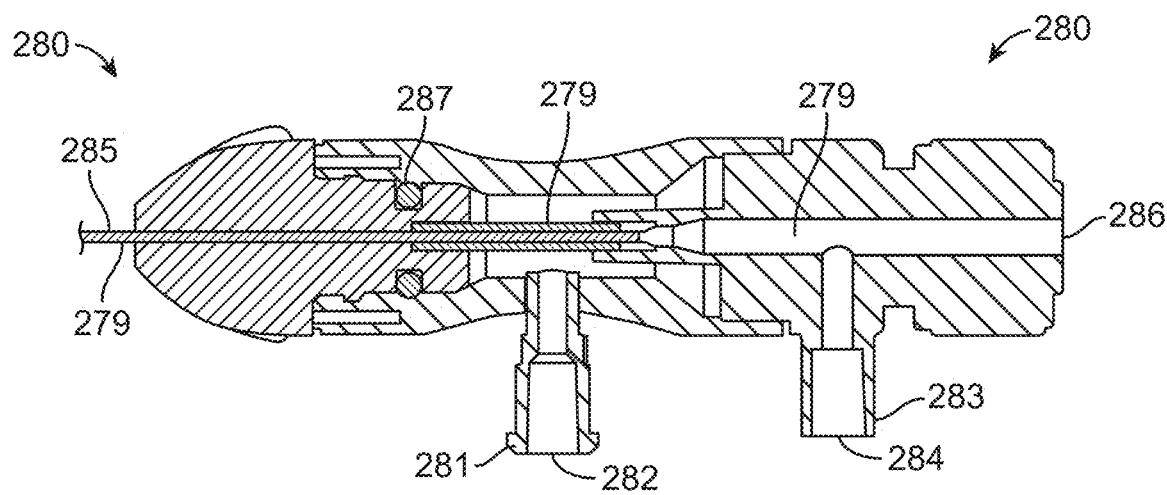

FIG. 34D shows the dual lumen removal system 280 with rotating handle in a cross-sectional view, rotating seal 287, and central lumen 279 that traverses from the probe port 286 on the proximal end through the dual lumen sheath 285.

Figure 35:
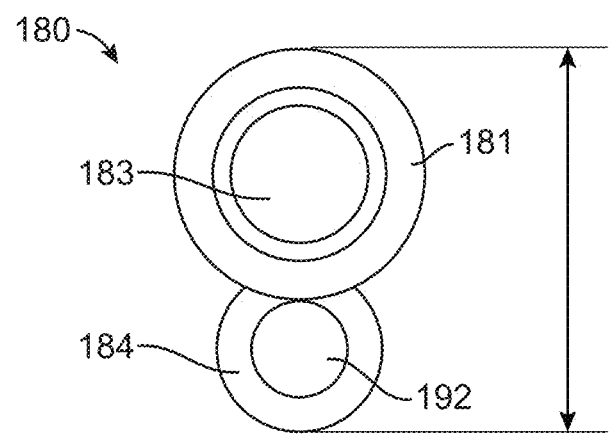
FIG. 35 shows a variation where the removal sheath has multiple lumens for both irrigation and aspiration. The probe for intraluminal confirmation can be housed or applied in either the irrigation or aspiration lumen.

FIG. 35 shows the dual lumen removal system 180 with eccentric lumens in an end-on view from the distal end opening of the irrigation lumen 183 and distal end opening of the aspiration lumen 192. The probe for intraluminal confirmation can be housed or applied in either the irrigation or aspiration lumen.

Figure 36:
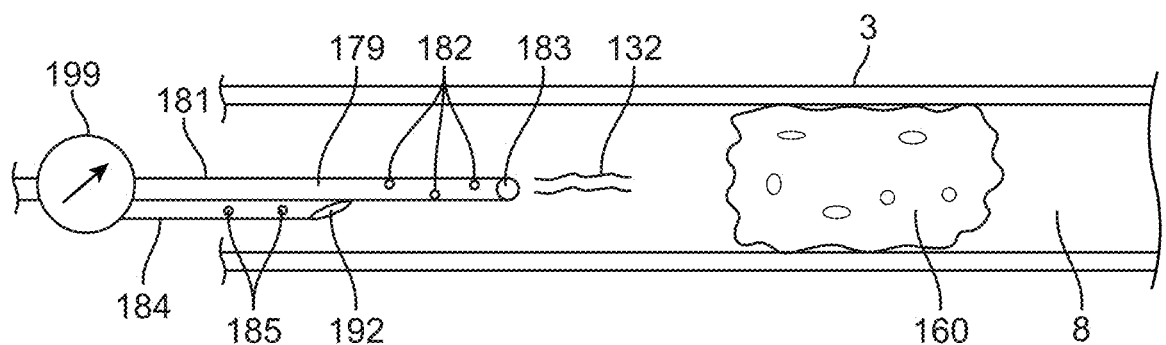
FIG. 36 demonstrates that at the time of removal, media can be delivered to confirm occlusion of the bodily lumen with the hydrogel using a force or pressure measurement.

FIG. 36 illustrates an occlusion measurement or identification system for use at the time of removal of an occlusive device. With intraluminal placement in a bodily lumen, media 132 can be delivered to confirm occlusion of the bodily lumen or vas deferens 3 by a hydrogel 160 using a force or pressure measurement device 199. Media 132 can be saline, phosphate buffered saline, Ringer's lactate, or other biocompatible fluid. Media can be a gas like CO2 as well. In practice dual lumen sheath 179 with irrigation lumen 181 for the delivery of media 132 with pressure measurement 199 can confirm the presence of the occlusion in the vas deferens 3.

Figure 37:
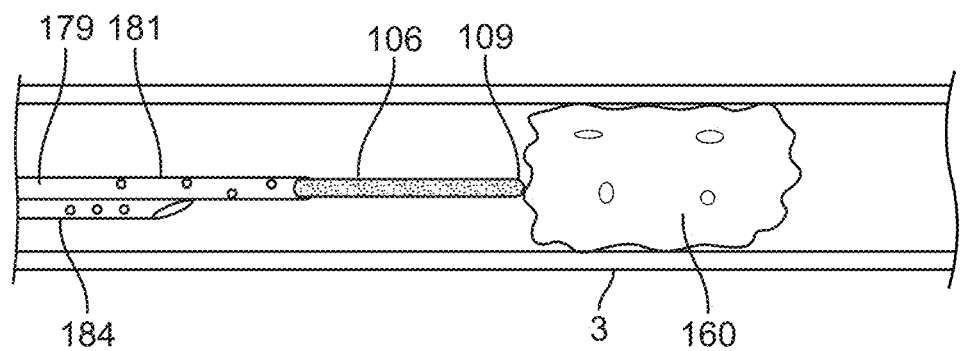
FIG. 37 illustrates that a probe can be advanced or translated to confirm occlusion in the bodily lumen by force measurements collected on the proximal end. Force measurements experienced from the advancement of the probe interacting with the intraluminal occlusion. The prevention of further translation of the probe in the lumen can be used to confirm occlusion in the bodily lumen.

FIG. 37 illustrates that a probe 106 can be advanced or translated to confirm occlusion in the bodily lumen or vas deferens 3 by force measurements collected on the proximal end of the probe 106 by a force measurement system (not shown). Force measurements experienced from the advancement of the probe 106 interacting with the intraluminal occlusion can be recorded.

Figure 38:
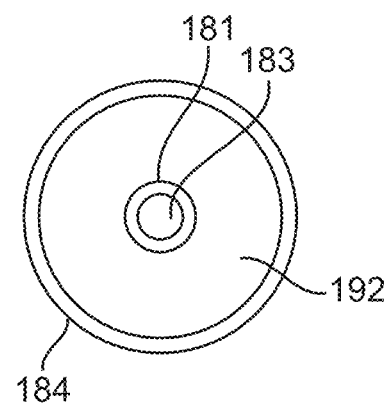
FIG. 38 shows a variation of the process of removal of the hydrogel with the instillation of a dissolving media into the bodily lumen with concurrent irrigation and aspiration. Dissolving media can be sodium bicarbonate solution composed of 8.4% sodium bicarbonate. The concentration of sodium bicarbonate can range from 4% to 10%. The installation can be performed with a two-lumen, co-linear concentric sheath system.

FIG. 38 shows in an end-on view of the distal end opening for the dual lumen removal sheath with concentric lumens. Central lumen shows the distal end opening of the irrigation lumen 183 of the irrigation lumen 181, with outer lumen having the aspiration lumen 184 and distal end opening of the aspiration lumen 192. The concentric design can be used for the removal of the hydrogel with the instillation of a dissolving media into the bodily lumen with concurrent irrigation and aspiration. Dissolving media can be sodium bicarbonate solution composed of 8.4% sodium bicarbonate. The concentration of sodium bicarbonate can range from 4% to 10%. The instillation of the sodium bicarbonate solution can be performed with a two-lumen, co-linear concentric sheath system.

Figure 39:
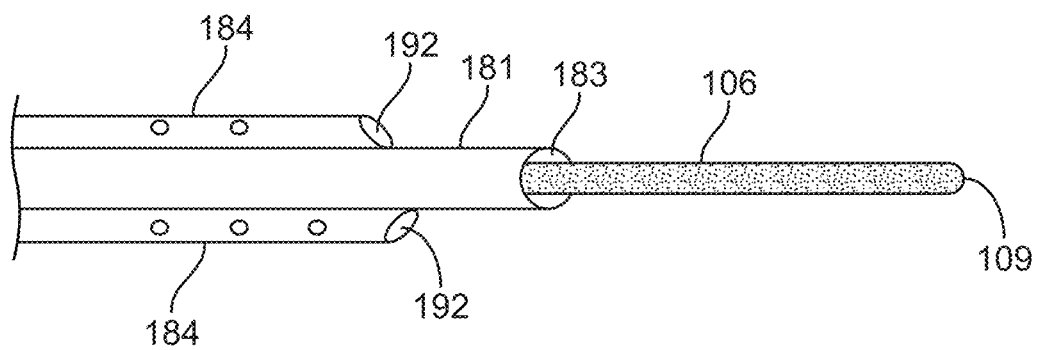
FIG. 39 shows that the two-lumen sheath system can have a central lumen for probe passage and irrigation with an eccentric lumen for aspiration that is proximal to the distal end of the irrigation lumen.

FIG. 39 shows that the dual lumen sheath system can have a central lumen 181 with distal end opening 183 for probe 106 passage and irrigation, with eccentric aspiration lumens 184 on the anterior and posterior surface of the irrigation lumen 181 for removal of excess media and dissolved hydrogel.

Figure 40:
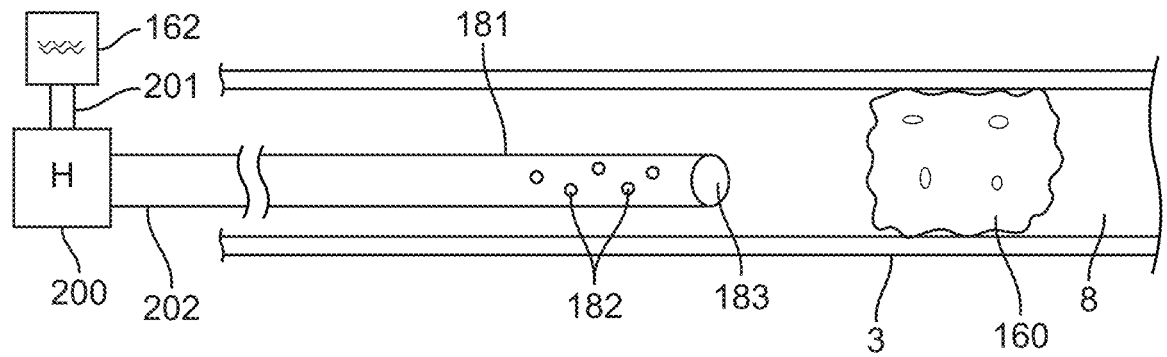
FIG. 40 shows that an additional heating source where the sodium bicarbonate can be administered at body temperature (37° C.), or a higher temperature than body temperature to accelerate the dissolution action on the hydrogel. The elevated temperature can range from 37.1° C. to 44° C. and is controlled to not create tissue necrosis or protein denaturation.

FIG. 40 shows that the removal of an occlusion device or hydrogel 160 can be with an additional heating source 200 where media or sodium bicarbonate solution can be administered at body temperature (37° C.), or a slightly higher temperature than body temperature but not enough create tissue necrosis, to accelerate the dissolution action on the hydrogel. The elevated temperature can range from 37.1° C. to 40° C. Media supply 162 can be placed through heating source 200 to elevate media temperature and is directed through the media heater connector 202 to the irrigation lumen 181 and into the bodily lumen through irrigation holes 182 and irrigation distal end opening 183.

Figure 41:
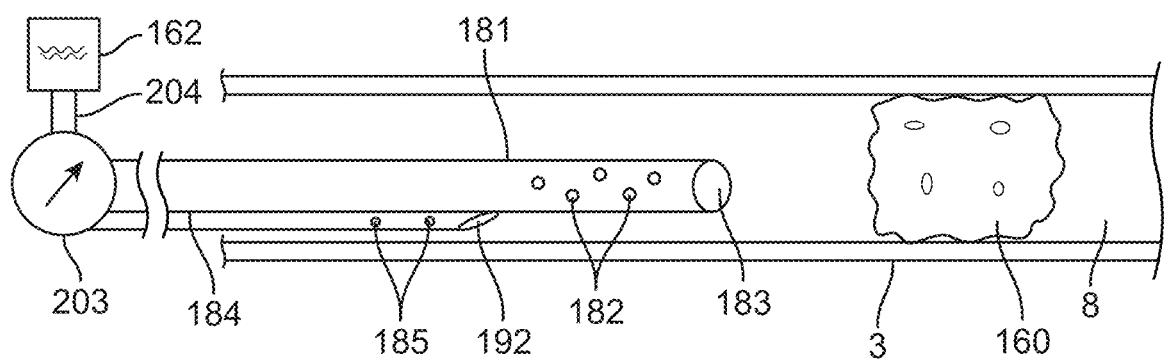
FIG. 41 shows that irrigation and aspiration can be controlled by a pressure regulator to ensure that the intraluminal pressure within the bodily lumen does not exceed 3 psi during continuous irrigation and aspiration. The maximum intraluminal pressures can range from 0.1 psi to 6 psi.

FIG. 41 shows that the removal of an occlusion device or hydrogel can be with irrigation and aspiration controlled by a pressure regulator 203 and the intraluminal pressure within the bodily lumen can be kept equal to or below 3 psi during continuous irrigation through irrigation lumen 181 and aspiration through aspiration lumen 184. Pressure regulation can minimize the amount of media distension within the vas deferens 3. The maximum intraluminal pressures can range from about 0.1 psi to about 6 psi.

Figure 42:
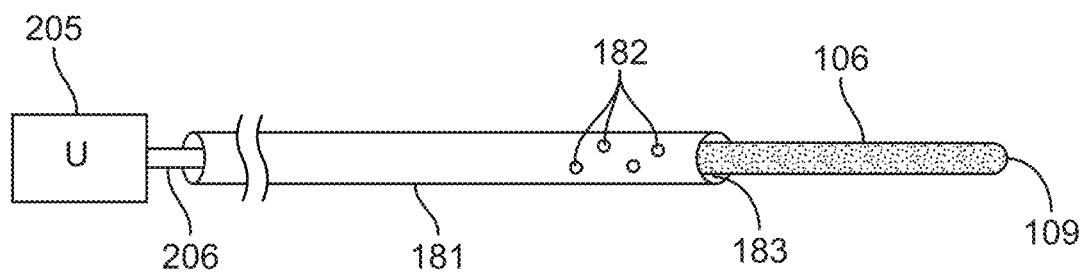
FIG. 42 shows a probe that can be configured to provide mechanical agitation to the occlusive hydrogel during the irrigation and aspiration process to accelerate the surface contact and dissolution of the hydrogel by the sodium bicarbonate solution. Manual agitation could be accomplished by forward and backward motion, rotary motion, or a combination of both motions on the probe. The proximal end of the probe can be configured with a handle to facilitate the user in applying these motions to the probe. Mechanical agitation can also be provided by an ultrasonic generation source connected to the proximal end of the probe.

FIG. 42 shows that the removal of an occlusion device or hydrogel can be with a probe 106 that can be configured to provide mechanical agitation with an ultrasonic generator source during the irrigation and aspiration process to accelerate the surface contact, break up, and dissolution of the hydrogel (not shown) by the sodium bicarbonate solution delivered through irrigation lumen 181 and irrigation holes 182. Mechanical agitation can be by an ultrasonic generation source connected with ultrasonic generator connector 206 to the proximal end of the probe 106.

Figure 43:
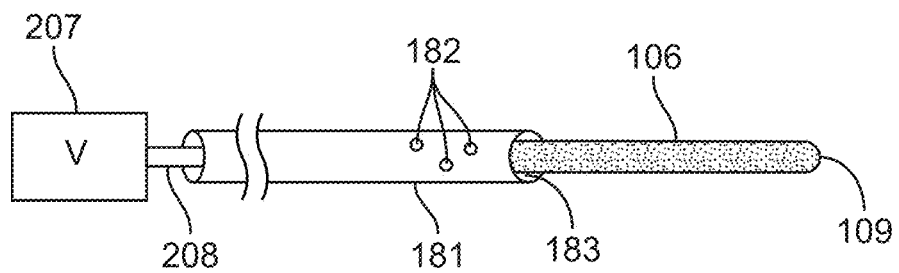
FIG. 43 shows that mechanical agitation can be provided by a vibratory generation source connected to the proximal end of the probe.

FIG. 43 shows that the removal of an occlusion device or hydrogel can be with a probe that can be configured to provide mechanical agitation with a vibratory source 207 during the irrigation and aspiration process to accelerate the surface contact, break up, and dissolution of the hydrogel (not shown) by the sodium bicarbonate solution delivered through irrigation lumen 181 and irrigation holes 182. Mechanical agitation can be provided by a vibratory source connected with vibration connector 208 to the proximal end of the probe 106.

Figure 44:
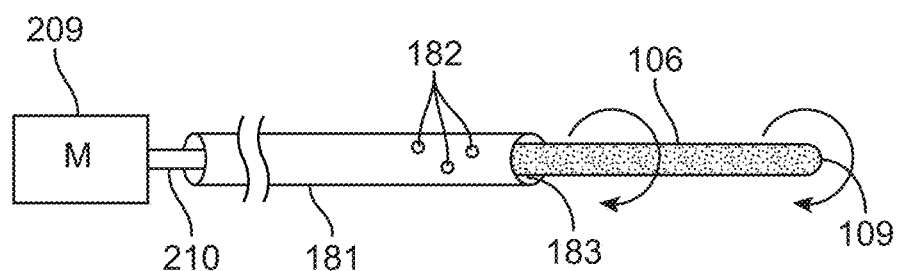
FIG. 44 shows that mechanical agitation can be provided by a motor providing rotational motion and is connected to the proximal end of the probe.

FIG. 44 shows a variation of mechanical agitation that can be provided by a rotary motion source 209 providing rotational motion and is connected by rotary motion source connector 210 to the proximal end of the probe 106.

FIGS. 45A to G show a variation for enhanced mechanical agitation from probe 106 within a bodily lumen for accelerated dissolution of an occlusion device.

Figure 45A:
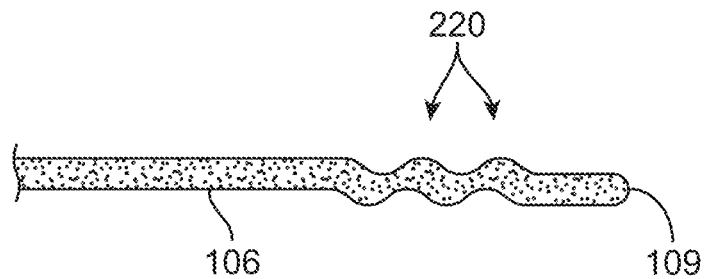
FIGS. 45A to G show mechanical agitation that can be further by protrusions (45A), bristles (45B), brushes (45C), indentations (45D), coils (45E), loops (45F), and angulations (45G) of the probe to further enhance the mechanical agitation of the probe on the occlusive hydrogel.

FIG. 45A demonstrates that the mechanical action of probe 106 can be further enhanced by protrusions 220 near the distal end 109 of probe 106.

Figure 45B:
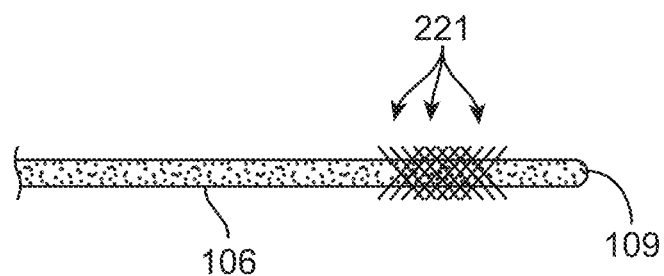

FIG. 45B shows a probe 106 with bristles 221 attached near the distal end 109 of probe 106 that are designed to agitate the occlusive device during removal.

Figure 45C:
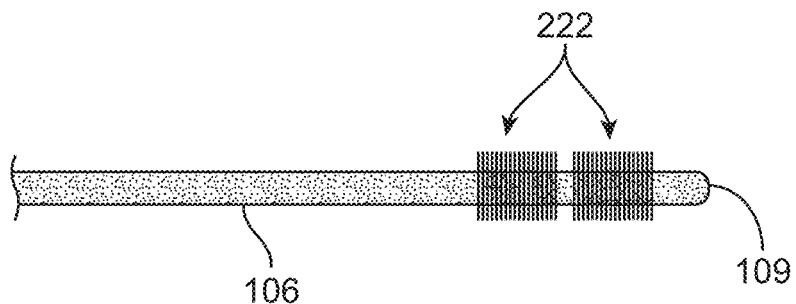

FIG. 45C shows a probe 106 with brushes 222 attached near the distal end 109 of probe that are designed to agitate the occlusive device during removal.

Figure 45D:
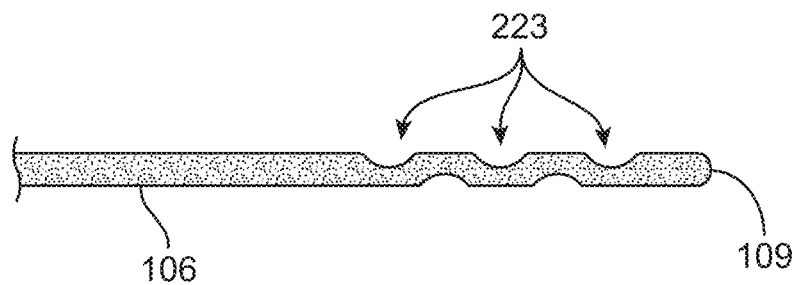

FIG. 45D shows a probe 106 with indentations 223 attached near the distal end 109 of probe 106 that are designed to agitate the occlusive device during removal.

Figure 45E:
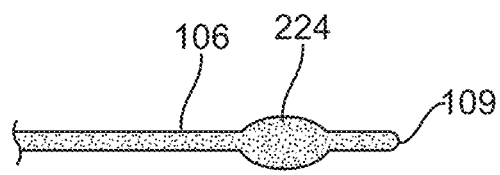
Figure 45E:
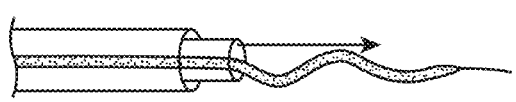
Figure 45E:
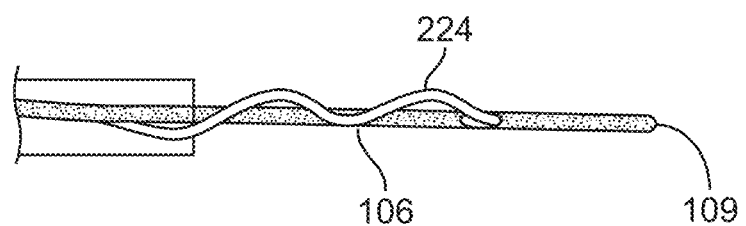

FIG. 45E shows a probe 106 with coils 224 attached near the distal end 109 of probe 106 that are designed to agitate the occlusive device during removal.

Figure 45F:
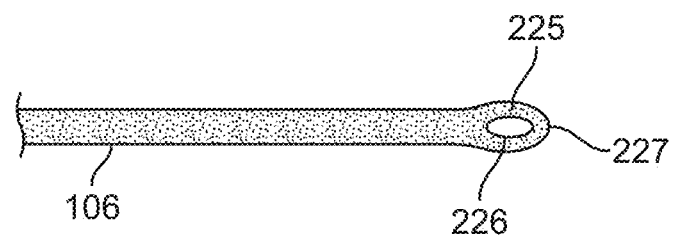

FIG. 45F shows a probe 106 with a loop 225 attached near the distal end 109 of probe 106 that are designed to agitate the occlusive device during removal. Probe 106 can be configured multiple loops near the distal end.

Figure 45G:
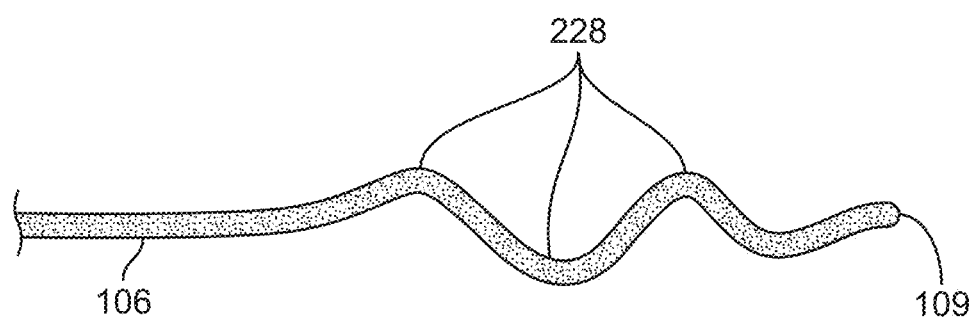

FIG. 45G shows a probe 106 with angulations 228 attached near the distal end 109 of probe 106 that are designed to agitate the occlusive device during removal. Angulations 228 are pre-formed or designed to retain their shape on probe 106 to provide mechanical action on the occlusive device.

Figure 46:
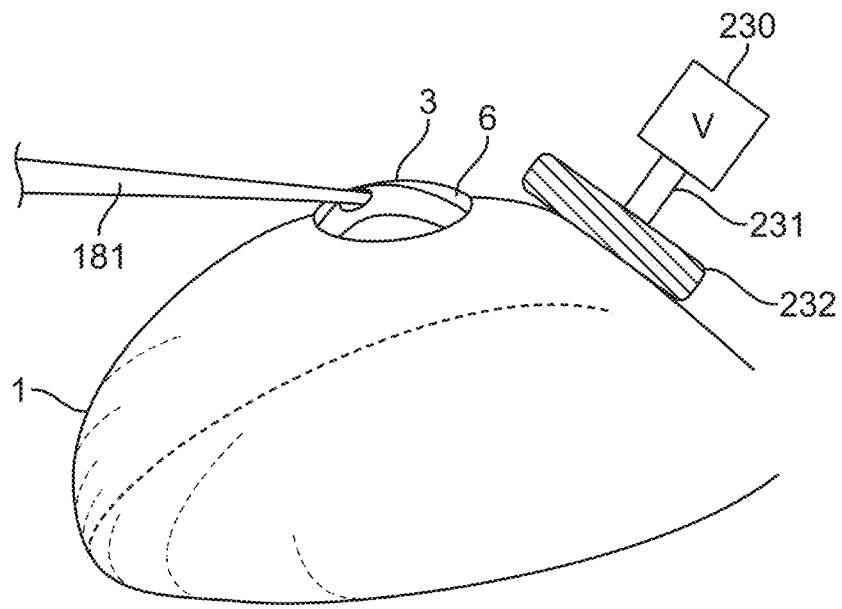
FIG. 46 shows that an external vibratory source can be applied to the bodily lumen during instillation of the dissolving media or sodium bicarbonate solution to enhance the agitation and action of the dissolving media.

FIG. 46 shows that an external vibratory source 230 can be applied to external portion of the bodily lumen during instillation of the dissolving media or sodium bicarbonate solution to enhance the agitation and action of the dissolving media. In practice, the vibratory source pad 232 would be applied on the scrotum 1 to apply vibration forces during the irrigation and aspiration application for removal by sheath 181 in vas deferens 3 that exposed through scrotal skin opening 6.

Figure 47:
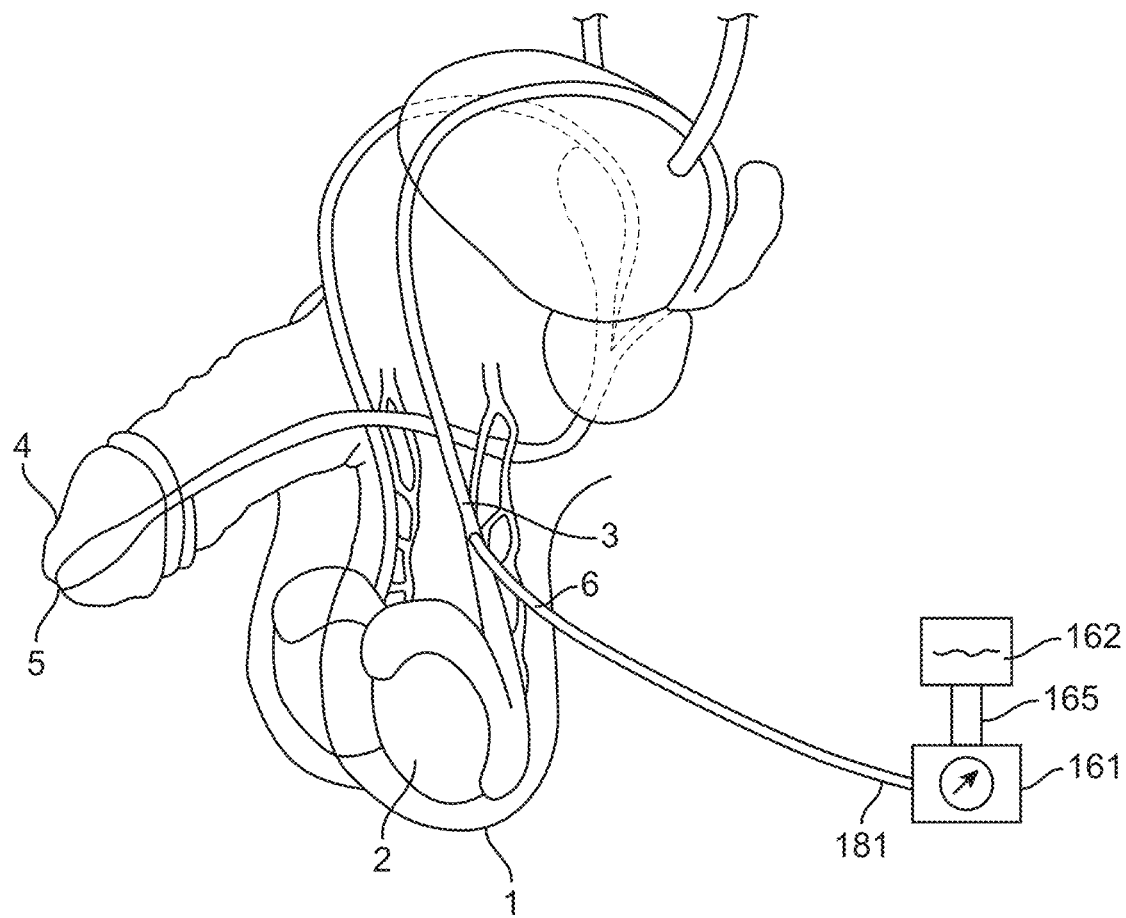
FIG. 47 demonstrates that the removal system can also supply a lavage of sodium bicarbonate at the completion of the removal step. Additional lavage media options include saline, phosphate buffered saline, Ringer's lactate, and other biocompatible media suitable for the reproductive tract. The removal system can be configured to have a force or flow measurement system to confirm or quantitate the restoration of patency in the bodily lumen during lavage. The lavage is visible as it goes through the vas deferens and exits the urethra.

FIG. 47 illustrates that the removal system can supply a lavage of sodium bicarbonate at the completion of the removal step. Additional lavage media options include saline, phosphate buffered saline, Ringer's lactate, and other biocompatible media suitable for the reproductive tract. The removal system has media supply 162 connected to media conduit 165 and force or flow measurement system 161 to confirm or quantitate the restoration of patency in the bodily lumen during lavage. Media for lavage is supplied to the vas deferens 3 through scrotal skin opening 6. Excess lavage can traverse the reproductive tract and exit the urethra 5.

FIGS. 48A to 48E illustrate a delivery or removal system with a penetrating sheath configured to wrap around the probe and intraluminal catheter. The wrap around sheath replaces the need for a needle, half needle, blunt dissection using the curved forceps, lancet, or trocar. After entry to the bodily lumen has been established, the wrap around sheath can be retracted, peeled away, or removed from the handle once entry into the bodily lumen has been established. The wrap around sheath facilitates the exchange of instrumentation without increasing the outer diameter of the entry site into the bodily lumen. Column strength of the wrap around penetrating sheath by the tightness of the circular wraps of sheath material like a tight funnel shape. The wrap around penetrating sheath is sized to perform the following steps: a) enter the bodily lumen, b) expand enough to only allow the probe to pass through its center and into the bodily lumen, c) expand further to only allow the access sheath to pass through its center and over the probe, and d) fully expend at its split to be retracted onto the delivery or removal handle or be retracted and peeled away from the entire handle assembly.

Wrap around penetrating sheaths can be made from thin wall polymers such as PEEK, PET, nylon and other biocompatible polymers that have strength in thin wall sections. Other material choices include stainless steel, titanium, nitinol, or other biocompatible metals.

Figure 49A:
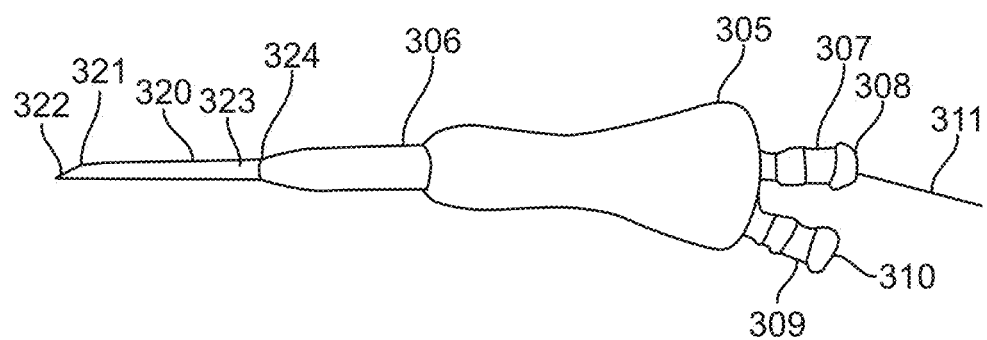
FIG. 49A shows the wrap around penetrating sheath on a delivery or removal handle.

FIG. 49A shows the wrap around penetrating sheath 300 at the distal end of a delivery or removal handle 305 with probe connector port 308 and irrigation or aspiration connector port 310 on the proximal end.

Figure 48A:
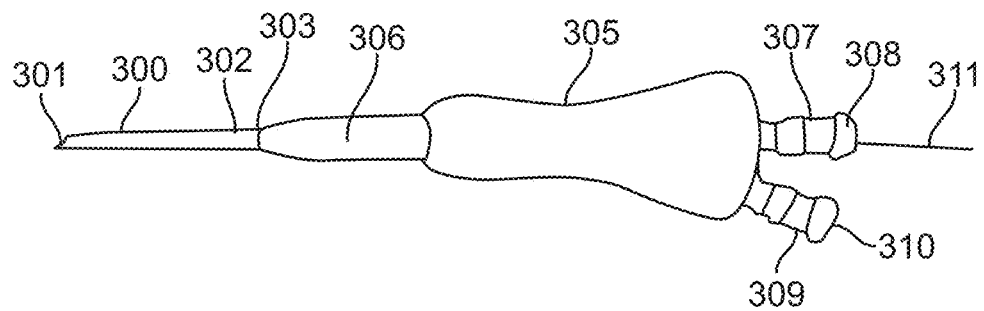
FIGS. 48A to 48E illustrate a delivery or removal system with a penetrating sheath configured to wrap around the probe and intraluminal catheter. The wrap around sheath and be retracted or peeled away from the handle once entry into the lumen has been established.
Figure 48B:
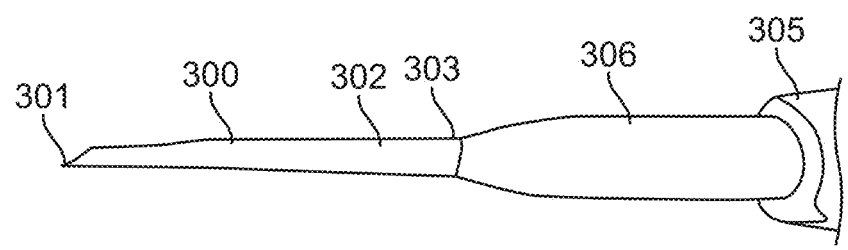

FIG. 48B shows a close-up view of the wrap around penetrating sheath 300 with sharp distal tip of wrap around penetrating sheath 301, pre-made split within wrap around penetrating sheath 302, and proximal end of wrap around penetrating sheath 303 positioned on nose cone of delivery or removal handle 306. In this configuration, distal tip of wrap around penetrating sheath 301 can be introduced into a bodily lumen be penetrating the anterior wall.

Figure 48C:
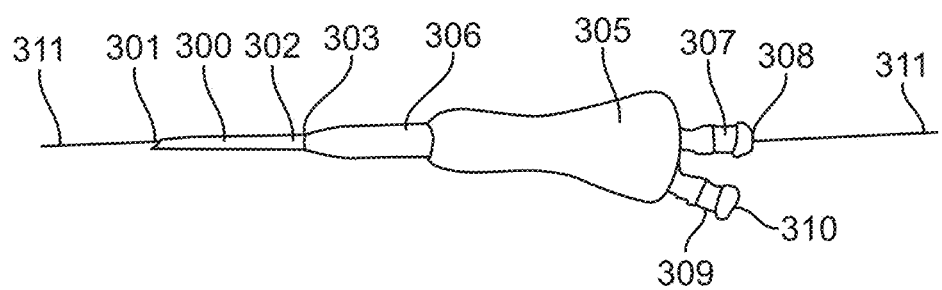

FIG. 48C shows the configuration of the wrap around penetrating sheath 300 once entry into the bodily lumen has been established and probe 311 is advanced through the distal opening of the wrap around penetrating sheath 300.

Figure 48D:
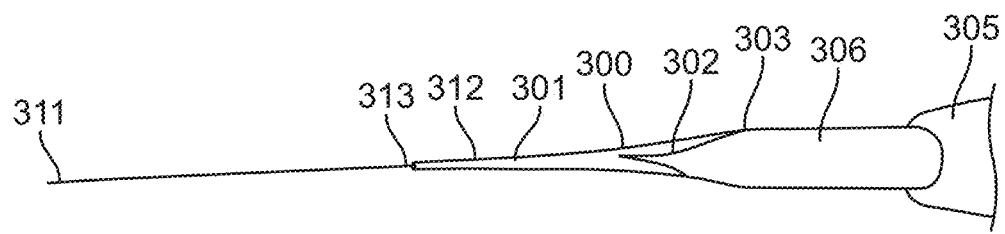

FIG. 48D shows the wrap around penetrating sheath 300 slightly retracted with both the probe 311 and intraluminal catheter 312 through the distal opening of the wrap around penetrating sheath 300. To accommodate the retraction process, split within wrap around penetrating sheath 302 expands onto the nose cone of the delivery or removal handle 306.

Figure 48E:
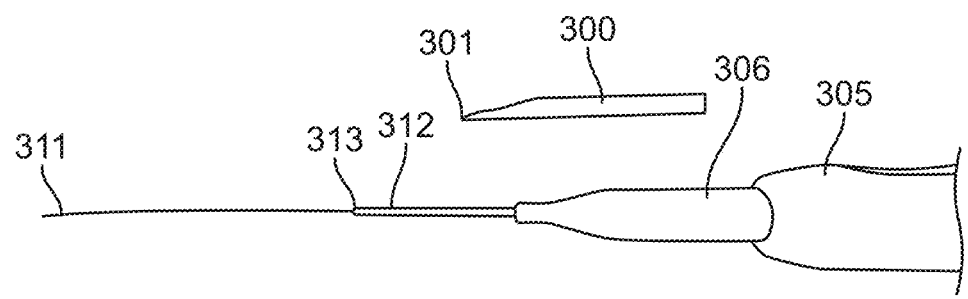

FIG. 48E shows the wrap around penetrating sheath 300 completely retracted and separate from the delivery or removal handle 305. The split within wrap around penetrating sheath 302 extends the entire length of the wrap around penetrating sheath 300 to enable complete retraction or peel away from delivery or removal handle 305.

Figure 49B:
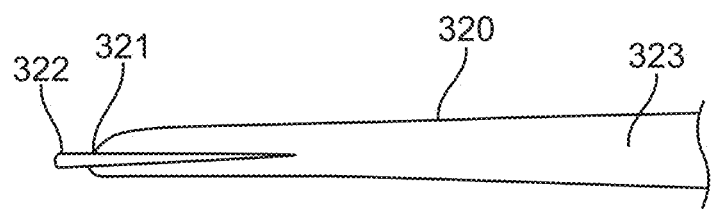
Figure 49C:
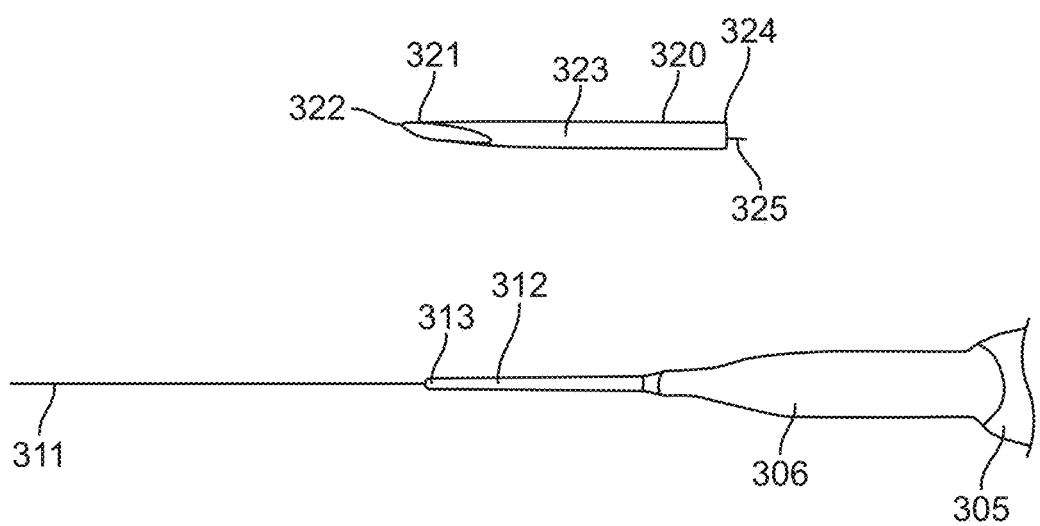

FIGS. 49A to 49C illustrate a variation of a wrap around penetrating sheath with a sharp pointed needle or lancet configured at the distal end to enhance entry and penetration into the bodily lumen. Needle is placed axially within the wrap around sheath and provides greater column strength or structure to the wrap around sheath for penetration.

FIG. 49A shows the delivery or removal handle 305 with wrap around penetrating sheath with needle 320.

FIG. 49B shows a close-up view of the wrap around penetrating sheath with needle 320 with sharp needle tip 322 located at the distal tip of the wrap around penetrating sheath 321. Axial split within wrap around penetrating sheath 323 runs the entire length of sheath.

FIG. 49C shows the wrap around penetrating sheath with needle 320 completely retracted and separate from the delivery or removal handle 305 with extended probe 311 and access sheath 312.

Figure 50A:
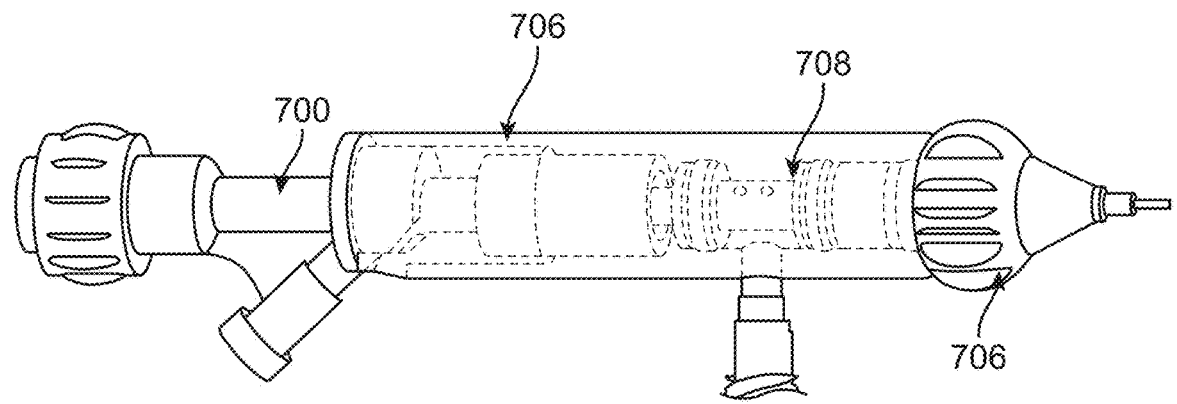
FIGS. 50A to 50B illustrate a removal system with alternating lumens for the irrigation and aspiration of the hydrogel.
Figure 50B:
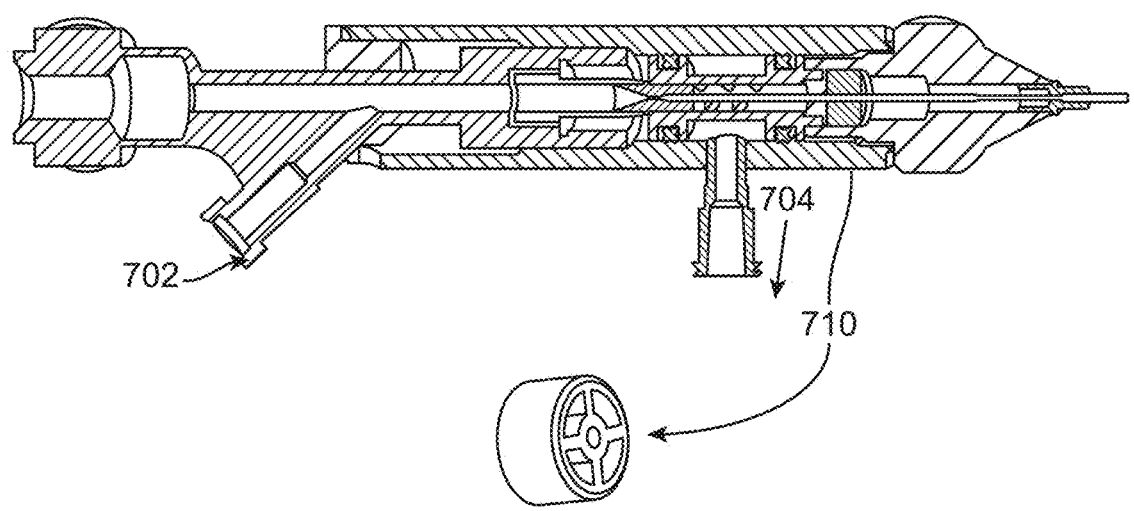

FIGS. 50A to 50B illustrate a removal system with alternating lumens for the irrigation and aspiration of the hydrogel. FIG. 50A shows the removal handle with a transparent section identifying the alternating lumens mechanism. The irrigation and aspiration tubings have pressure relief valves to ensure that the intraluminal pressure of the vas deferens is controlled. Examples of pressure ranges are from 1 psi to 10 psi, or 3 psi as a nominal value. The irrigation and aspiration of the hydrogel can be monitored as a function of time. Examples of time durations are 1 minute to 10 minutes of irrigation and aspiration, or 4 minutes as a nominal time duration. Alternatively, the irrigation and aspiration step can be performed using a predetermined volume of sodium bicarbonate solution, of other dissolving solution, and terminating the step when the fluid volume is exhausted. Examples of fluid volumes include 10 cc to 250 cc, or 50 cc as a nominal fluid volume. At the conclusion of the irrigation and aspiration step, a final irrigation lavage can be performed with the visual confirmation of effluent from the patient's urethra to signify a patent vas deferens. Additionally, the advancement of the removal catheter past the hydrogel implantation site is another confirmation that the occlusive hydrogel has been removed. FIG. 50B shows the removal system in cross-section with a close-up illustration of the rotation wheel for alternating the lumens.

Figure 51A:
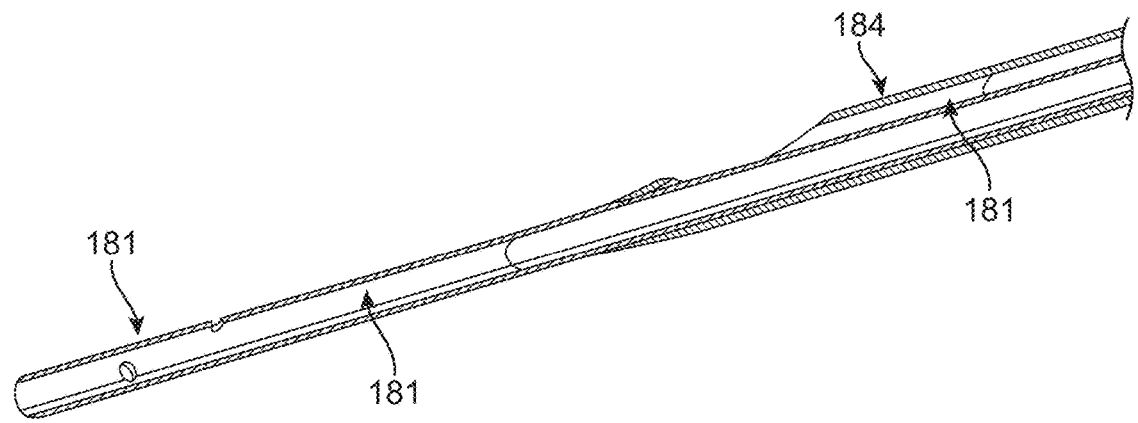
FIGS. 51A to 51B show the distal end of the removal system and dual-lumen catheters.
Figure 51B:
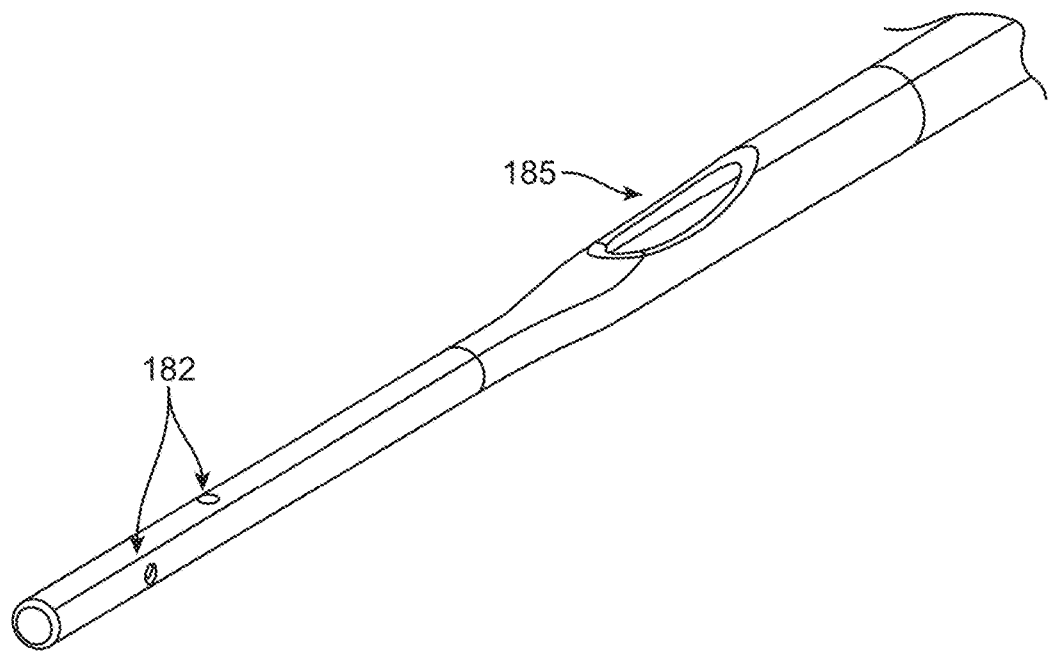

FIGS. 51A to 51B show another removal catheter system with the distal end of the removal system and dual-lumen catheters. FIG. 51A shows in cross-section the distal end of the dual-lumen catheter. FIG. 51B shows a side-view of the distal end of the removal catheter with the aspiration hole and irrigation side holes.

U.S. Pat. Nos. 9,861,515 and 10,456,292 are incorporated by reference herein in their entireties for all purposes.

A method of confirming intraluminal access of a lumen in a body is disclosed (e.g., as shown in the drawings and/or as described herein). The method can include inserting a sheath into the body, advancing a probe relative to the sheath by an advancing distance into the lumen, and/or confirming the sheath has access to the lumen if the advancing distance is greater than or equal to a threshold distance.

Inserting the sheath into the body can include penetrating tissue with a penetrator. The penetrator can be a distal end of the sheath and/or a needle.

Inserting the sheath into the body can include inserting the sheath through an incision.

Advancing the probe relative to the sheath by the advancing distance into the lumen can include advancing the probe out of the sheath by the advancing distance.

Advancing the probe relative to the sheath by the advancing distance into the body can include advancing the probe out of a port by the advancing distance. The sheath or a penetrator can have the port. The port can be a distal terminal opening of the sheath or an opening on a side of the sheath. The port can be an opening of the penetrator. The port can be proximal a distal tip of the sheath. The port can be proximal a distal tip of the penetrator. The penetrator can be a needle.

Confirming the sheath has access to the lumen if the advancing distance is greater than or equal to the threshold distance can include confirming the sheath is in the lumen if the advancing distance is greater than or equal to the threshold distance.

Inserting the sheath into the body can include inserting a port into the body. Confirming the sheath has access to the lumen if the advancing distance is greater than or equal to the threshold distance can include confirming the port has access to the lumen if the advancing distance is greater than or equal to the threshold distance. The sheath or a penetrator have the port. The port can be a distal terminal opening of the sheath or an opening on a side of the sheath. The port can be an opening of the penetrator. The port can be proximal a distal tip of the sheath. The port can be proximal a distal tip of the penetrator. The penetrator can be a needle.

Inserting the sheath into the body can include inserting a port into the body. Confirming the sheath has access to the lumen if the advancing distance is greater than or equal to the threshold distance can include confirming the port is in the lumen if the advancing distance is greater than or equal to the threshold distance. The sheath or a penetrator can have the port. The port can be a distal terminal opening of the sheath or an opening on a side of the sheath. The port can be an opening of the penetrator. The port can be proximal a distal tip of the sheath. The port can be proximal a distal tip of the penetrator. The penetrator can be a needle.

The method can include confirming the sheath does not have access to the lumen if the advancing distance is less than the threshold distance. Confirming the sheath does not have access to the lumen if the advancing distance is less than the threshold distance can include confirming the sheath is not in the lumen if the advancing distance is less than the threshold distance. Inserting the sheath into the body can include inserting a port into the body. Confirming the sheath does not have access to the lumen if the advancing distance is less than the threshold distance can include confirming the port does not have access to the lumen if the advancing distance is less than the threshold distance. The sheath or a penetrator can have the port. The port can be a distal terminal opening of the sheath or an opening on a side of the sheath. The port can be an opening of the penetrator. The port can be proximal a distal tip of the sheath. The port can be proximal a distal tip of the penetrator. The penetrator can be a needle. Inserting the sheath into the body can include inserting a port into the body. Confirming the sheath does not have access to the lumen if the advancing distance is less than the threshold distance can include confirming the port is not in the lumen if the advancing distance is less than the threshold distance. The sheath or a penetrator can have the port. The port can be a distal terminal opening of the sheath or an opening on a side of the sheath. The port can be an opening of the penetrator. The port can be proximal a distal tip of the sheath. The port can be proximal a distal tip of the penetrator. The penetrator can be a needle.

The method can include delivering a material into the lumen after confirming the sheath has access to the lumen. The material can be an implant. The material can be material of an implant. The material can be implanted material. The implant, the material of the implant, and/or the implanted material can be a hydrogel. The material can form an occlusion. The material can be a hydrogel. The material can be configured to dissolve an implant. The material can be sodium bicarbonate. The material can be configured to alter a physical property and/or a chemical property of an implant.

The method can include delivering a material through the sheath into the lumen after confirming the sheath has access to the lumen.

The method can include delivering a material through a port into the lumen after confirming the port has access to the lumen. The sheath or a penetrator can have the port.

The method can include retracting the probe relative to the sheath. The method can include delivering a material through the sheath into the lumen after confirming the sheath has access to the lumen and after retracting the probe relative to the sheath. The method can include delivering a material through a port into the lumen after confirming the port has access to the lumen and after retracting the probe relative to the sheath. The material can be a hydrogel.

The method can include retracting the probe into the sheath. The method can include delivering a material through the sheath into the lumen after confirming the sheath has access to the lumen and after retracting the probe into the sheath. The method can include delivering a material through a port into the lumen after confirming the port has access to the lumen and after retracting the probe into the sheath. Retracting the probe into the sheath can include retracting the probe into the port.

The method can include delivering a material into the lumen.

The method can include removing a material from the lumen after confirming the sheath has access to the lumen. The material can be an implant. The material can be material of an implant. The material can be implanted material. The implant, material of the implant, and/or the implanted material can be a hydrogel. The material can form an occlusion. The material can be a hydrogel. The material can be configured to dissolve an implant. The material can be sodium bicarbonate. The material can be configured to alter a physical property and/or a chemical property of an implant. Removing the material from the lumen after confirming the sheath has access to the lumen can include aspirating the material from the lumen after confirming the sheath has access to the lumen.

The method can include removing a material from the lumen into the sheath after confirming the sheath has access to the lumen. Removing the material from the lumen into the sheath after confirming the sheath has access to the lumen can include aspirating the material from the lumen into the sheath after confirming the sheath has access to the lumen.

The method can include removing a material from the lumen through a port after confirming the port has access to the lumen. The sheath or a penetrator can have the port. Removing the material from the lumen through the port after confirming the port has access to the lumen can include aspirating the material from the lumen through the port after confirming the port has access to the lumen.

The method can include moving a material from the lumen into the sheath after confirming the sheath has access to the lumen. Moving the material from the lumen into the sheath after confirming the sheath has access to the lumen can include aspirating the material from the lumen into the sheath after confirming the sheath has access to the lumen.

The method can include retracting the probe relative to the sheath. The method can include removing a material from the lumen into the sheath after confirming the sheath has access to the lumen and after retracting the probe relative to the sheath. The method can include removing a material from the lumen through a port after confirming the port has access to the lumen and after retracting the probe relative to the sheath. Retracting the probe relative the sheath can include retracting the probe into the port.

The method can include retracting the probe into the sheath. The method can include removing a material from the lumen into the sheath after confirming the sheath has access to the lumen and after retracting the probe into the sheath. The method can include removing a material from the lumen through a port after confirming the port has access to the lumen and after retracting the probe into the sheath. Retracting the probe into the sheath can include retracting the probe into the port.

The method can include removing a material from the lumen.

The method can include delivering a first material into the lumen after confirming the sheath has access to the lumen. The first material can be configured to dissolve a second material. The first material can be sodium bicarbonate. The first material can be configured to alter a physical property and/or a chemical property of a second material. The method can include removing a second material from the lumen. The second material can be an implant. The second material can be material of an implant. The second material can be implanted material. The implant, the material of the implant, and/or the implanted material can be a hydrogel. The second material can be an occlusion. The second material can be a hydrogel. Removing the second material from the lumen can include aspirating the second material from the lumen. The method can include removing the first material from the lumen. Removing the first material from the lumen can include aspirating the first material from the lumen. Removing the second material from the lumen can include aspirating the second material from the lumen. The method can include simultaneously removing the first material and the second material from the lumen.

The method can include delivering a first material into the lumen after confirming the sheath has access to the lumen. The method can include changing a physical property of a second material in the lumen via the first material. The method can include removing the first material and/or the second material from the lumen. Removing the first material and/or the second material from the lumen can include aspirating the first material and/or the second material from the lumen.

The method can include delivering a first material into the lumen after confirming the sheath has access to the lumen. The method can include agitating a second material in the lumen with the probe. The method can include agitating the first material in the lumen with the probe.

The method can include delivering a first material into the lumen after confirming the sheath has access to the lumen. The method can include agitating the first material and/or a second material in the lumen with the probe.

The probe can be a first probe. The method can include agitating a second material in the lumen with a second probe. The method can include agitating the first material in the lumen with the second probe.

The probe be a first probe. The method can include agitating the first material and/or a second material in the lumen with a second probe.

The method can include agitating a first material and/or a second material with the probe. The first material can be a fluid. The second material can be an implant. The second material can be material of an implant. The second material can be implanted material. The implant, the material of the implant, and/or the implanted material can be a hydrogel. The first material can be sodium bicarbonate. The implant can be a hydrogel. The method can include removing the first material and/or the second material from the lumen. Removing the first material and/or the second material from the lumen can include aspirating the first material and/or the second material from the lumen.

The probe can be a first probe. The method can include agitating a first material and/or a second material with a second probe. The first material can be a fluid. The second material can be material of an implant. The second material can be implanted material. The implant, the material of the implant, and/or the implanted material can be a hydrogel. The first material can be sodium bicarbonate. The implant can be a hydrogel. The method can include removing the first material and/or the second material from the lumen. Removing the first material and/or the second material from the lumen can include aspirating the first material and/or the second material from the lumen.

The method can include delivering a first material into the lumen after confirming the sheath has access to the lumen. The lumen can have a second material. The method can include creating a third material in the lumen via a chemical reaction between the first material and the second material. The probe can be a first probe. The method can include removing the first material, the second material, and/or the third material from the lumen and/or the method can include agitating the first material, the second material, and/or the third material in the lumen with the first probe and/or with a second probe. Removing the first material, the second material, and/or the third material from the lumen can include aspirating the first material, the second material, and/or the third material from the lumen.

The threshold distance can be 1.0 cm to 15.0 cm. The threshold distance can be 1.0 cm to 10.0 cm. The threshold distance can be 1.0 cm to 5.0 cm. The threshold distance can be 5.0 cm, 5.0 cm or less, 10.0 cm or less, or 15.0 cm or less.

The lumen can be a lumen of a reproductive tract. The lumen can be a lumen of a vas deferens. The lumen can be a lumen of a blood vessel.

The method can include preventing delivery of a material into the lumen until confirming the sheath has access to the lumen.

The method can include unlocking a lock upon or after confirming the sheath has access to the lumen.

The sheath can be a tube. The sheath can be a catheter. The sheath can have a needle. A distal tip of the sheath can have a needle. The probe can be a guidewire.

Advancing the probe can include advancing the probe via a spring or a spring-loaded retractable lancet system.

Advancing the probe relative to the sheath by the advancing distance into the lumen can include advancing the probe out of the sheath by the advancing distance.

Confirming the sheath has access to the lumen if the advancing distance is greater than or equal to the threshold distance can include confirming the sheath is in the lumen if the advancing distance is greater than or equal to the threshold distance.

Inserting the sheath into the body can include inserting a port into the body. Confirming the sheath has access to the lumen if the advancing distance is greater than or equal to the threshold distance can include confirming the port has access to the lumen if the advancing distance is greater than or equal to the threshold distance.

The method can include delivering a material into the lumen after confirming the sheath has access to the lumen. The material can be a hydrogel or can be configured to alter a physical property and/or a chemical property of an implant.

The method can include removing a material from the lumen after confirming the sheath has access to the lumen. The material can be a hydrogel or can be configured to alter a physical property and/or a chemical property of an implant.

The lumen can be a lumen of a reproductive tract.

A device is disclosed (e.g., as shown in the drawings and/or as described herein). The device can have a sheath and a probe. The probe can be advanceable from a retracted configuration to an advanced configuration relative to the sheath. When the probe is in the retracted configuration, a first distance can be between the probe and the sheath. When the probe is in the advanced configuration, a second distance greater than the first distance can be between the probe and the sheath. The first distance can be less than a threshold distance. When the second distance is greater than or equal to the threshold distance, the advanced configuration of the probe can be an indicator to a user that the device has access to a target site.

When the second distance is greater than or equal to the threshold distance, the advanced configuration of the probe can be an indicator to a user that the device is in the target site.

When the second distance is greater than or equal to the threshold distance, the advanced configuration of the probe can be an indicator to a user that the sheath has access to the target site.

When the second distance is greater than or equal to the threshold distance, the advanced configuration of the probe can be an indicator to a user that the sheath is in the target site.

When the second distance is greater than or equal to the threshold distance, the advanced configuration of the probe can be an indicator to the user that a port has access to the target site. The sheath or a penetrator can have the port. The port can be a distal terminal opening of the sheath or an opening on a side of the sheath. The port can be an opening of the penetrator. The port can be proximal a distal tip of the sheath. The port can be proximal a distal tip of the penetrator. The penetrator can be a needle.

When the second distance is greater than or equal to the threshold distance, the advanced configuration of the probe can be an indicator to the user that a port is in the target site. The sheath or a penetrator can have the port. The port can be a distal terminal opening of the sheath or an opening on a side of the sheath. The port can be an opening of the penetrator. The port can be proximal a distal tip of the sheath. The port can be proximal a distal tip of the penetrator. The penetrator can be a needle.

When the second distance is less than the threshold distance, the advanced configuration of the probe can be an indicator to the user that the device does not have access to the target site.

When the second distance is less than the threshold distance, the advanced configuration of the probe can be an indicator to a user that the device is outside of the target site.

When the second distance is less than the threshold distance, the advanced configuration of the probe can be an indicator to a user that the sheath does not have access to the target site.

When the second distance is less than the threshold distance, the advanced configuration of the probe can be an indicator to a user that the sheath is outside of the target site.

When the second distance is less than the threshold distance, the advanced configuration of the probe can be an indicator to the user that a port does not have access to the target site. The sheath or a penetrator can have the port. The port can be a distal terminal opening of the sheath or an opening on a side of the sheath. The port can be an opening of the penetrator. The port can be proximal a distal tip of the sheath. The port can be proximal a distal tip of the penetrator. The penetrator can be a needle.

When the second distance is greater than or equal to the threshold distance, the advanced configuration of the probe can be an indicator to the user that a port is outside of the target site. The sheath or a penetrator can have the port. The port can be a distal terminal opening of the sheath or an opening on a side of the sheath. The port can be an opening of the penetrator. The port can be proximal a distal tip of the sheath. The port can be proximal a distal tip of the penetrator. The penetrator can be a needle.

The target site can be a lumen. The target site can be a lumen of a reproductive tract. The target site can be a lumen of a vas deferens. The target site can be a lumen of a blood vessel.

The sheath can have a sheath lumen. When the probe is in the retracted configuration, a distal end of the probe can be inside the sheath lumen. When the probe is in the advanced configuration, the distal end of the probe can be outside the sheath lumen. When the probe is in the retracted configuration, a distal terminal end of the device can be the sheath. When the probe is in the advanced configuration, the distal terminal end of the device can be the probe. When the probe is in the retracted configuration, the sheath can form a distal terminal end of the device. When the probe is in the advanced configuration, the probe can form the distal terminal end of the device. When the probe is in the retracted configuration, the distal terminal end of the device can be a distal terminal end of the sheath. When the probe is in the advanced configuration, the distal terminal end of the device can be a distal terminal end of the probe. When the probe is in the retracted configuration, a distal terminal end of the sheath can form the distal terminal end of the device. When the probe is in the advanced configuration, a distal terminal end of the probe can form the distal terminal end of the device.

The sheath can have a sheath lumen. More of the probe can be distal the sheath lumen when the probe is in the advanced configuration than when the probe is in the retracted configuration. Some or none of the probe can be distal the sheath lumen when the probe is in the retracted configuration.

More of the probe can be outside the sheath when the probe is in the advanced configuration than when the probe is in the retracted configuration. Some or none of the probe can be outside the sheath when the probe is in the retracted configuration.

When the probe is in the retracted configuration, a distal terminal end of the probe can be proximal a distal terminal end of the sheath.

When the probe is in the retracted configuration, a distal terminal end of the probe can be distal a distal terminal end of the sheath. The device can have a penetrator. The penetrator can be the distal terminal end of the probe and/or the distal terminal end of the sheath.

When the probe is in the retracted configuration, a distal terminal end of the device can be a distal terminal end of the probe and a distal terminal end of the sheath.

When the probe is in the retracted configuration, a distal terminal end of the probe can be collinear with a distal terminal end of the sheath.

The device can have a material in a reservoir. Before the second distance becomes greater than or equal to the threshold distance, a flow path that extends between the reservoir and a distal end of the sheath can have a closed configuration. When and/or after the second distance becomes greater than or equal to the threshold distance, the flow path that extends between the reservoir and the distal end of the sheath can have an open configuration. A lumen of the sheath can be the flow path. The device can have a barrier. When the flow path has the closed configuration, the barrier can be in the flow path. When the flow path has the open configuration, the barrier can be outside of the flow path. Less of the barrier can be in the flow path when the flow path has the open configuration than when the flow path has the closed configuration. The barrier can have a valve and/or a trigger lock.

The device can have a lock. When the second distance is less than the threshold distance, the lock can be in a locked state. When the second distance is greater than or equal to the threshold distance, the lock can be in an unlocked state. When the lock is in the locked state, the device can prevent delivery of a material through the sheath. When the lock is in the unlocked state, the device can allow delivery of the material through the sheath.

The device can have a material. Before the second distance is greater than or equal to the threshold distance, the material can be outside the sheath and/or can be proximal a distal terminal end of the sheath. After the second distance is greater than or equal to the threshold distance, the material can be inside the sheath and/or can be distal the distal terminal end of the sheath. The material can be an implant (e.g., material of an implant, the entire implant, a portion of the implant), form an occlusion, be a hydrogel, be configured to dissolve an implant, or any combination thereof. The material can be sodium bicarbonate. The material can be configured to alter a physical property and/or a chemical property of an implant.

The device can have a material and a material reservoir. A flow path can extend between the material reservoir and a distal end of the sheath. The device can have a first configuration, a second configuration, and a third configuration. Before the second distance becomes greater than or equal to the threshold distance, the device can have the first configuration. When the second distance becomes greater than or equal to the threshold distance, the device can have the second configuration or the device can be changeable from the first configuration to the second configuration. After the second distance becomes greater than or equal to the threshold distance, the device can have the third configuration. When the device is in the first configuration, the material can be in the material reservoir and the flow path can be open or closed. When the device is in the second configuration, the material can be between the material reservoir and a distal terminal end of the sheath and the flow path can be open or closed. When the device is in the third configuration, the material can be distal a distal terminal end of the sheath and the flow path can be open or closed. The reservoir can be a first portion of a lumen of the sheath, and/or the flow path can be a second portion of the lumen of the sheath. The reservoir can be insertable into a lumen of the sheath. When the device is in the first configuration, the material can be outside of a lumen of the sheath. When the device is in the second configuration, the material can be inside the lumen of the sheath. When the device is in the second configuration, the material can be in contact with the probe and/or is distal a distal terminal end of the probe. When the device is in the second configuration, the probe can be in the retracted configuration. The material can be an implant (e.g., material of an implant, the entire implant, a portion of the implant), form an occlusion, be a hydrogel, be configured to dissolve an implant, or any combination thereof. The material can be sodium bicarbonate. The material can be configured to alter a physical property and/or a chemical property of an implant.

After the second distance becomes greater than or equal to the threshold distance, a material can be deliverable through the sheath. Before the second distance becomes greater than or equal to the threshold distance, the material may not be deliverable through the sheath. Before the second distance becomes greater than or equal to the threshold distance, the device can prevent delivery of a material through the sheath. The material can be an implant (e.g., material of an implant, the entire implant, a portion of the implant), form an occlusion, be a hydrogel, be configured to dissolve an implant, or any combination thereof. The material can be sodium bicarbonate. The material can be configured to alter a physical property and/or a chemical property of an implant.

The device can have a first material and a second material. Before the second distance is greater than or equal to the threshold distance, the first material can be outside the sheath and/or can be proximal a distal terminal end of the sheath. After the second distance is greater than or equal to the threshold distance, the first material can be inside the sheath and/or can be distal the distal terminal end of the sheath. Before the second distance is greater than or equal to the threshold distance, the second material can be outside the sheath. After the second distance is greater than or equal to the threshold distance, the second material can be inside the sheath and/or can be distal the distal terminal end of the sheath. The first material can be a fluid. The first material can be configured to dissolve the second material. The first material can be sodium bicarbonate. The first material can be configured to alter a physical property and/or a chemical property of the second material The second material can be an implant. The second material can be material of an implant. The second material can be implanted material. The implant, the material of the implant, and/or the implanted material can be a hydrogel.

The device can have a first material and a second material. The device can have a first configuration and a second configuration. When the device is in the first configuration, the first material can be proximal a distal terminal end of the sheath and the second material can be distal the distal terminal end of the sheath. When the device is in the second configuration, the first material and the second material can be distal the distal terminal end of the sheath. The device can have a third configuration. When the device is in the third configuration, the first material, the second material, and/or a third material can be proximal the distal terminal end of the sheath. The sheath can have a sheath lumen. When the device is in the first configuration, the first material can be in a reservoir and/or inside the sheath lumen and the second material can be outside the sheath lumen. When the device is in the second configuration, the first material and the second material can be outside the sheath lumen. When the device is in the second configuration, a third material can be outside the sheath lumen distal the distal terminal end of the sheath. An interaction between the first material and the second material outside the sheath can be configured to produce the third material. The device can have a third configuration. When the device is in the third configuration, the first material, the second material, and/or a third material can be inside the sheath lumen. An interaction between the first material and the second material can be configured to produce the third material outside the sheath lumen distal the distal terminal end of the sheath when the device is in the second configuration. The first material can be a fluid, the second material can be an implant (e.g., material of an implant, the entire implant, a portion of the implant), and the third material can be a mixture of the first material and the second material. The first material can be a fluid, the second material can be an implant (e.g., material of an implant, the entire implant, the portion of an implant), and the third material can be a material different than the first material and the second material. When the device is in the second configuration, an interaction between the first material and the second material can be configured to produce the third material outside the sheath lumen distal the distal terminal end of the sheath. The device can have a third configuration. When the device is in the third configuration, the first material, the second material, and/or the third material can be inside the sheath lumen.

The device can have a first material, a second material, a reservoir, and a receptacle. The reservoir can be configured to hold the first material. The receptacle can be configured to hold the first material, the second material, and/or a third material. The sheath can have a sheath lumen. The reservoir can include the sheath lumen. The receptacle can include the sheath lumen.

The device can have an irrigator and/or an aspirator. A distal end of the sheath can have a port. When the irrigator is irrigating, the port can be in fluid communication with the irrigator. When the aspirator is aspirating, the port can be in fluid communication with the aspirator. The irrigator can have a first manual pump and/or a first electric pump. The aspirator can have a second manual pump and/or a second electric pump. When the device is in a first configuration, a first material is configured to flow out of the port. When the device is in a second configuration, the first material, a second material, and/or a third material can be configured to flow into the port. The sheath can have a sheath lumen. A distal terminal end of the sheath lumen can have the port.

The device can have an irrigator and/or an aspirator. A distal end of the sheath can have an outflow port and an inflow port. When the irrigator is irrigating, the outflow port can be in fluid communication with the irrigator. When the aspirator is aspirating, the inflow port can be in fluid communication with the aspirator. The irrigator can have a first manual pump and/or a first electric pump. The aspirator can have a second manual pump and/or a second electric pump. When the device is in a first configuration, a first material can be configured to flow out of the outflow port. When the device is in a second configuration, the first material, a second material, and/or a third material can be configured to flow into the inflow port. The sheath can have an inflow channel and an outflow channel. A distal terminal end of the inflow channel can have the inflow port. A distal terminal end of the outflow channel can have the outflow port.

The device can have a first material. More of the first material can be distal the sheath and the probe after the second distance is greater than or equal to the threshold distance than before the second distance is greater than or equal to the threshold distance. The first material can be configured to dissolve a second material. The first material can be sodium bicarbonate. The first material can be configured to alter a physical property and/or a chemical property of a second material. The device can have a second material. More of the second material can be proximal a distal terminal end of the sheath after the second distance is greater than or equal to the threshold distance than before the second distance is greater than or equal to the threshold distance. The second material can be an implant. The second material can be an occlusion. The second material can be a hydrogel. The device can have an aspirator. The aspirator can be configured to aspirate the first material and/or the second material into the sheath. The aspirator can be configured to simultaneously aspirate the first material and the second material into the sheath. The probe can be configured to agitate a second material outside the sheath and/or inside a lumen of the sheath. The probe can be configured to agitate the first material outside the sheath and/or inside the lumen of the sheath. The probe can be configured to agitate the first material and/or the second material outside the sheath and/or inside a lumen of the sheath. The probe can be a first probe. The device can have a second probe. The second probe can be configured to agitate a second material outside the sheath and/or inside a lumen of the sheath. The second probe can be configured to agitate the first material outside the sheath and/or inside the lumen of the sheath.

The probe can be a first probe. The device can have a second probe. The second probe can be configured to agitate the first material and/or a second material outside the sheath and/or inside a lumen of the sheath.

The probe can be a first probe The device can have a second probe. The first probe and/or the second probe can be configured to agitate a first material and/or a second material outside the sheath and/or inside a lumen of the sheath. The first material can be a fluid. The second material can be an implant. The implant can be a hydrogel. The device can have an aspirator. The aspirator can be configured to aspirate the first material and/or the second material into the sheath.

The probe can be a first probe. The device can have a second probe. The first probe and/or the second probe can be configured to agitate a first material, a second material, and/or a third material outside the sheath and/or inside a lumen of the sheath. The device can have an aspirator. The aspirator can be configured to aspirate the first material and/or the second material into the sheath. The first material can be a fluid. The second material can be an implant. The implant can be a hydrogel.

The device can have a spring. The probe can be advanceable from the retracted configuration to the advanced configuration via the spring. The probe can be retractable from the advanced configuration to the retracted configuration via the spring.

The first distance can be measured along a straight line or a curved line between a tip of the sheath and a tip of the probe.

The second distance can be measured along a straight line and/or a curved line between a tip of the sheath and a tip of the probe.

The second distance can be measured along the same straight line and/or the same curved line as the first distance can be measured along.

The first distance can be a longitudinal distance between a tip of the sheath and a tip of the probe.

The first distance can be a distance of zero (e.g., 0.0 cm, 0.0 mm) between a tip of the sheath and a tip of the probe.

The probe can be retractable from the advanced configuration to the retracted configuration relative to the sheath. The probe can be advanceable from the retracted configuration to the advanced configuration inside a lumen of the sheath. The probe can be retractable from the advanced configuration to the retracted configuration inside the lumen of the sheath.

The threshold distance can be 1.0 cm to 15.0 cm. The threshold distance can be 1.0 cm to 10.0 cm. The threshold distance can be 1.0 cm to 5.0 cm. The threshold distance can be 5.0 cm, 5.0 cm or less, 10.0 cm or less, or 15.0 cm or less.

The sheath can be a tube. The sheath can be a catheter.

A distal end of the sheath can be configured to puncture tissue.

The sheath can be a needle.

A distal end of the sheath can be a needle.

The sheath can have a needle.

The device can have a needle.

The probe can be a guidewire.

The first probe and/or the second probe can be a guidewire.

The second probe can be the same as the first probe, for example, such that the first probe and the second probe are identical probes but part of two different devices (e.g., two different identical devices).

When the second distance is greater than or equal to the threshold distance, the advanced configuration of the probe can be an indicator to a user that the sheath and/or a port has access to the target site.

The sheath can have a sheath lumen. More of the probe can be distal the sheath lumen when the probe is in the advanced configuration than when the probe is in the retracted configuration.

The device can have a material and/or a material reservoir. A flow path can extend between the material reservoir and a distal end of the sheath. The device can have a first configuration, a second configuration, and a third configuration. Before the second distance becomes greater than or equal to the threshold distance, the device can have the first configuration. When the second distance becomes greater than or equal to the threshold distance, the device can have the second configuration or the device can be changeable from the first configuration to the second configuration. After the second distance becomes greater than or equal to the threshold distance, the device can have the third configuration. When the device is in the first configuration, the material can be in the material reservoir and the flow path can be open or closed. When the device is in the second configuration, the material can be between the material reservoir and a distal terminal end of the sheath and the flow path can be open or closed. When the device is in the third configuration, the material can be distal a distal terminal end of the sheath and the flow path can be open or closed.

The device can have an irrigator and/or an aspirator. A distal end of the sheath can have a port. When the irrigator is irrigating, the port can be in fluid communication with the irrigator. When the aspirator is aspirating, the port can be in fluid communication with the aspirator.

The systems, devices, and/or methods disclosed herein can have any combination of features shown in the drawings and/or described herein (e.g., any combination of features between "A method of confirming intraluminal access of a lumen in a body is disclosed (e.g., as shown in the drawings and/or as described herein)" and "The second probe can be the same as the first probe, for example, such that the first probe and the second probe are identical probes but part of two different devices (e.g., two different identical devices)" above).

A method of removing a first material from a body lumen is disclosed (e.g., as shown in the drawings and/or as described herein). The method can include inserting a sheath into the body lumen, advancing a probe into the body lumen relative to the sheath, agitating the first material in the body lumen with the probe, irrigating a second material into the body lumen, and/or removing the first material from the body lumen.

Inserting the sheath into the body can include penetrating tissue with a penetrator. The penetrator can be a distal end of the sheath and/or a needle.

Inserting the sheath into the body can include inserting the sheath through an incision.

Agitating the first material in the body lumen with the probe can include mechanically agitating the first material in the body lumen with the probe. The first material can be an implant. The first material can be material of an implant. The first material can be implanted material. The implant, the material of the implant, and/or the implanted material can be a hydrogel. The second material can be a fluid (e.g., sodium bicarbonate). The second material can change a chemical property and/or a physical property of the first material.

Agitating the first material in the body lumen with the probe can include moving the probe relative to the sheath in the body lumen. Moving the probe relative to the sheath in the body lumen can include translating, rotating, and/or vibrating the probe in the body lumen. Moving the probe in the body lumen can include a user and/or a motion source moving the probe. The motion source can include a vibratory motion source, an ultrasonic motion source, a translation motion source, and/or a rotational motion source. Moving the probe in the body lumen can include applying vibratory motion, a dottering motion, an ultrasonic motion, a translational motion, and/or a rotational motion to the probe.

Agitating the first material in the body lumen with the probe can include agitating the first material in the body lumen while the probe is in contact with the first material.

Agitating the first material in the body lumen with the probe can include moving the probe into and out of contact with the first material.

Agitating the first material in the body lumen with the probe can include moving the probe into and out of contact with the first material while the second material is in contact with the first material.

Agitating the first material in the body lumen with the probe can include agitating the first material in the body lumen while the probe is in contact with the second material.

Agitating the first material in the body lumen with the probe can include moving the first material in the body lumen via the probe while the second material is in contact with the first material and/or the probe in the body lumen.

The method can include moving the first material in the body lumen via irrigating the second material into the body lumen. The method can include removing the second material from the body lumen. The method can include removing the second material from the body lumen into the sheath. The method can include moving the first material in the body lumen via removing the second material from the body lumen into the sheath. The method can include moving the first material in the body lumen via irrigating the second material into the body lumen and/or removing the second material from the body lumen. The method can include moving the first material in the body lumen via simultaneously irrigating the second material into the body lumen and removing the second material from the body lumen into the sheath.

The method can include moving the first material in the body lumen via a flow of the second material in the body lumen toward and/or away from the sheath.

Agitating the first material in the body lumen with the probe can include moving the first material relative to the sheath and/or the second material.

Agitating the first material in the body lumen with the probe can include moving the first material toward and/or away from the sheath in the body lumen.

Agitating the first material in the body lumen with the probe can include moving the first material toward and/or away from the second material in the body lumen.

Agitating the first material in the body lumen with the probe can include mechanically breaking down the first material with the probe.

Agitating the first material in the body lumen with the probe can include mixing the first material and the second material together in the body lumen. The first material can be an implant. The first material can be material of an implant. The first material can be implanted material. The implant, the material of the implant, and/or the implanted material can be a hydrogel. The second material can be a fluid (e.g., sodium bicarbonate). The second material can change a chemical property and/or a physical property of the first material.

Agitating the first material in the body lumen with the probe can include forcing the first material into the second material and/or forcing the second material into the first material.

Agitating the first material in the body lumen with the probe can include mixing the first material into the second material and/or mixing the second material into the first material.

The method can include forming, via the first material and the second material interacting with each other in the body lumen, a solution and/or a mixture in the body lumen. The first material and the second material interacting with each other in the body lumen can include the first material and the second material mixing in the body lumen and/or a chemical reaction between the first material and the second material in the body lumen. The first material can be an implant. The first material can be material of an implant. The first material can be implanted material. The implant, the material of the implant, and/or the implanted material can be a hydrogel. The second material can be a fluid.

The method can include forming, from the first material and/or the second material in the body lumen, a solution and/or a mixture in the body lumen. The solution and/or the mixture can be a third material. The solution and/or the mixture can be a dissolved form of the first material and/or a disassociated form of the first material.

The method can include forming a dissolved form of the first material and/or a disassociated form of the first material in the body lumen.

The method can include forming a dissolved form of the first material and/or a disassociated form of the first material via an interaction between the first material and the second material in the body lumen.

Agitating the first material in the body lumen with the probe can include forming, from the first material and/or the second material in the body lumen, a solution and/or a mixture in the body lumen. Agitating the first material in the body lumen with the probe can include forming a third material in the body lumen. The solution and/or the mixture can be the third material. The third material can have a chemical property that is different from the first material and/or the second material.

The method can include forming, via the second material and a third material interacting with each other in the body lumen, the first material in the body lumen. The first material can be a solution and/or a mixture. The second material can be a fluid. The third material can be an implant. The third material can be material of an implant. The third material can be implanted material. The implant, the material of the implant, and/or the implanted material can be a hydrogel. The solution and/or the mixture can be a portion of the implant. The solution and/or the mixture can be a piece of the implant. The solution and/or the mixture can be a dissolved form of the third material and/or a disassociated form of the third material. The second material and the third material interacting with each other in the body lumen can include the second material and the third material mixing in the body lumen and/or a chemical reaction between the second material and the third material in the body lumen.

The method can include forming, from the second material and/or a third material in the body lumen, the first material in the body lumen. The first material can be a dissolved form of the third material and/or a disassociated form of the third material. The second material can be a fluid. The third material can be an implant. The third material can be material of an implant. The third material can be implanted material. The implant, the material of the implant, and/or the implanted material can be a hydrogel.

Agitating the first material in the body lumen with the probe can include forming, from the second material and/or a third material in the body lumen, the first material in the body lumen. The second material can be a fluid. The third material can be an implant. The third material can be material of an implant. The third material can be implanted material. The implant, the material of the implant, and/or the implanted material can be a hydrogel. The first material can be a mixture and/or a solution having the second material and/or the third material. The first material can have a chemical property that is different from a chemical property of the first material and/or a chemical property of the second material.

The method can include agitating the second material in the body lumen with the probe. Agitating the second material in the body lumen with the probe can include mechanically agitating the second material in the body lumen with the probe. Agitating the second material in the body lumen with the probe can include moving the probe in the body lumen. Moving the probe in the body lumen can include translating, rotating, and/or vibrating the probe in the body lumen. Moving the probe in the body lumen can include a user and/or a motion source moving the probe. The motion source can be a vibratory motion source, an ultrasonic motion source, a translation motion source, and/or a rotational motion source. Moving the probe in the body lumen can include applying vibratory motion, a dottering motion, an ultrasonic motion, a translational motion, and/or a rotational motion to the probe. Agitating the second material in the body lumen with the probe can include agitating the second material in the body lumen while the probe is in contact with the first material and/or the second material. Agitating the first material in the body lumen with the probe can include moving the probe into and out of contact with the first material. Agitating the second material in the body lumen with the probe can include moving the second material while the second material is in contact with the first material in the body lumen. Agitating the second material in the body lumen with the probe can include agitating the second material in the body lumen while the probe is in contact with the second material. Agitating the second material in the body lumen with the probe can include moving the second material relative to the sheath and/or the first material. Agitating the second material in the body lumen with the probe can include moving the second material toward and/or away from the sheath in the body lumen. Agitating the second material in the body lumen with the probe can include moving the second material toward and/or away from the first material in the body lumen. Agitating the first material in the body lumen with the probe and agitating the second material in the body lumen with the probe can include simultaneously agitating the first material and the second material in the body lumen with the probe. Agitating the second material in the body lumen with the probe can include mixing the first material and the second material together in the body lumen. Agitating the second material in the body lumen with the probe can include forcing the first material into the second material and/or forcing the second material into the first material. Agitating the second material in the body lumen with the probe can include mixing the first material into the second material and/or mixing the second material into the first material. Agitating the second material in the body lumen with the probe can include creating turbulence and/or flow in the second material in the body lumen. The second material can be a fluid. The second material can be a liquid and/or a gas.

The method can include agitating the second material and/or a third material in the body lumen with the probe. Agitating the second material and/or the third material in the body lumen with the probe can include mechanically agitating the second material and/or the third material in the body lumen with the probe. Agitating the second material and/or the third material in the body lumen with the probe can include moving the probe in the body lumen. Moving the probe in the body lumen can include translating, rotating, and/or vibrating the probe in the body lumen. Moving the probe in the body lumen can include a user and/or a motion source moving the probe. The motion source can be a vibratory motion source, an ultrasonic motion source, a translation motion source, and/or a rotational motion source. Moving the probe in the body lumen can include applying vibratory motion, a dottering motion, an ultrasonic motion, a translational motion, and/or a rotational motion to the probe. Agitating the second material and/or the third material in the body lumen with the probe can include forming the third material in the body lumen by mixing the first material and the second material together in the body lumen. Agitating the second material and/or the third material in the body lumen with the probe can include agitating the second material and/or the third material in the body lumen while the probe is in contact with the second material and/or the third material. Agitating the first material in the body lumen with the probe can include moving the probe into and out of contact with the first material. Agitating the second material and/or the third material in the body lumen with the probe can include mixing the first material and the second material together in the body lumen. Agitating the second material and/or the third material in the body lumen with the probe can include forcing the first material into the second material and/or forcing the second material into the first material. Agitating the second material and/or the third material in the body lumen with the probe can include mixing the first material into the second material and/or mixing the second material into the first material. Agitating the second material and/or the third material in the body lumen with the probe can include creating turbulence and/or flow in the second material and/or the third material in the body lumen. The second material can be a first fluid. The third material can be a second fluid. The third material can be a mixture of the first material and the second material and/or can be a different material than the first material and/or the second material. Agitating the second material and/or the third material in the body lumen with the probe can include moving the second material and/or the third material relative to the sheath and/or the first material. Agitating the second material and/or the third material in the body lumen with the probe can include moving the second material and/or the third material toward and/or away from the sheath in the body lumen. Agitating the second material and/or the third material in the body lumen with the probe can include moving the second material and/or the third material toward and/or away from the first material in the body lumen. The method can include simultaneously agitating the first material, the second material, and the third material in the body lumen with the probe. Agitating the second material and/or the third material in the body lumen with the probe can include moving the second material and/or the third material while the second material is in contact with the first material in the body lumen. Agitating the second material and/or the third material in the body lumen with the probe can include agitating the second material and/or the third material in the body lumen while the probe is in contact with the second material and/or the third material. Agitating the second material and/or the third material in the body lumen with the probe can include agitating the second material and/or the third material in the body lumen while the probe is in contact with the first material, the second material, and the third material.

The body lumen can be a lumen of a reproductive tract. The body lumen can be a lumen of a vas deferens. The body lumen can be a lumen of a blood vessel.

The first material can be an implanted material or an implant. The first material can form an occlusion. The first material can include a hydrogel. The first material can include a fluid and an implant. The first material can be a mixture and/or a solution having the second material and/or a third material.

The second material can be a dissolving material. The second material can be a sodium bicarbonate solution. The second material can be configured to dissolve and/or disassociate the first material. The second material can be a liquid and/or a gas.

The method can include a third material or having a third material. The third material can be a fluid and/or an implant. The third material can be a mixture and/or a solution comprising the first material and/or the second material.

The method can include forming a third material via an interaction between the first material and the second material.

The method can include forming a third material in the body lumen via an interaction between the first material and the second material in the body lumen.

The method can include forming a third material via an interaction between the first material and the second material distal a distal terminal end of the sheath. The method can include forming the third material via an interaction between the first material and the second material distal a distal terminal end of the probe. Forming the third material via the interaction between the first material and the second material distal the distal terminal end of the sheath can include forming the third material forming the third material via the interaction between the first material and the second material between the distal terminal end of the sheath and a distal terminal end of the probe.

The method can include forming the third material via an interaction between the first material and the second material in the body lumen outside the sheath. The third material can be a solution comprising the first material and the second material. The third material can include a mixture of the first material and the second material. The third material can have a different physical property or a different chemical property than the first material and/or the second material.

The method can include forming a third material via the second material dissolving and/or disassociating the first material.

The method can include forming a third material via the second material dissolving and/or disassociating the first material distal a distal terminal end of the sheath. The method can include forming the third material via the second material dissolving and/or disassociating the first material distal a distal terminal end of the probe. Forming the third material via the second material dissolving and/or disassociating the first material distal the distal terminal end of the sheath can include forming the third material via the second material dissolving and/or disassociating the first material between the distal terminal end of the sheath and a distal terminal end of the probe.

The method can include forming a third material via the second material dissolving and/or disassociating the first material in the body lumen outside the sheath. The third material can be a solution comprising the first material and the second material. The third material can comprise a mixture of the first material and the second material. The third material can have a different physical property or a different chemical property than the first material and/or the second material.

The method can include forming a third material by altering a physical property and/or a chemical property of the first material via the second material.

The method can include forming a third material by altering a physical property and/or a chemical property of the first material via the second material distal a distal terminal end of the sheath. The method can include forming the third material by altering the physical property and/or the chemical property of the first material via the second material distal a distal terminal end of the probe. Forming the third material by altering the physical property and/or the chemical property of the first material via the second material distal the distal terminal end of the sheath can include forming the third material by altering the physical property and/or the chemical property of the first material via the second material between the distal terminal end of the sheath and a distal terminal end of the probe.

The method can include forming a third material by altering a physical property and/or a chemical property of the first material via the second material in the body lumen outside the sheath. The third material can be a solution comprising the first material and the second material. The third material can be a mixture of the first material and the second material.

The method can include dissolving and/or disassociating the first material with the second material.

The method can include dissolving and/or disassociating the first material with the second material in the body lumen. Dissolving and/or disassociating the first material with the second material in the body lumen can form a dissolved and/or disassociated first material in the body lumen. Removing the first material from the body lumen can include removing the dissolved and/or disassociated first material from the body lumen. Dissolving and/or disassociating the first material with the second material in the body lumen can form a mixture of the first material and the second material. Removing the first material from the body lumen can include removing the mixture of the first material and the second material from the body lumen. Dissolving and/or disassociating the first material with the second material in the body lumen can form a third material in the body lumen. The third material can be a solution comprising the first material and the second material. The third material can be a mixture of the first material and the second material. The third material can have a different physical property or a different chemical property than the first material and/or the second material. Removing the first material from the body lumen can include removing the third material from the body lumen. Removing the first material from the body lumen can include first forming the third material by dissolving and/or disassociating the first material with the second material in the body lumen and then removing the third material from the body lumen.

The method can include simultaneously irrigating the second material, agitating the first material, and removing the first material and the second material.

The method can include simultaneously removing the first material, the second material, and/or a third material from the body lumen.

The probe can have a protrusion, a bristle, a brush, an indentation, a coil, a loop, and/or an angulation. Agitating the first material in the body lumen with the probe can include agitating the first material in the body lumen with the protrusion, the bristle, the brush, the indentation, the coil, the loop, and/or the angulation.

The probe can have protrusions, bristles, brushes, indentations, coils, loops, and/or angulations. Agitating the first material in the body lumen with the probe can include agitating the first material in the body lumen with the protrusions, the bristles, the brushes, the indentations, the coils, the loops, and/or the angulations.

The probe can have one or multiple protrusions, one or multiple bristles, one or multiple brushes, one or multiple indentations, one or multiple coils, one or multiple loops, and/or one or multiple angulations. Agitating the first material in the body lumen with the probe can include agitating the first material in the body lumen with the one or multiple protrusions, the one or multiple bristles, the one or multiple brushes, the one or multiple indentations, the one or multiple coils, the one or multiple loops, and/or the one or multiple angulations.

Advancing the probe into the body lumen relative to the sheath can include advancing the probe out of the sheath and/or the method can include retracting the probe into the sheath.

Advancing the probe into the body lumen relative to the sheath can include advancing the probe into the body lumen relative to the sheath after inserting the sheath into the body lumen.

The method can include agitating the first material inside the body lumen from outside the body lumen with an agitator. The method can include applying the agitator to an external surface outside of the body lumen. The external surface can include an external surface of a scrotum. The agitator can be a vibrator.

Removing the first material from the body lumen can include removing the first material from the body lumen into the sheath.

The method can include irrigating the second material into the body lumen when the first material is distal a distal terminal end of the sheath and/or when the second material is 15.0 cm or less, 10.0 cm or less, or 5.0 cm or less from the distal terminal end of the sheath.

The method can include irrigating the second material into the body lumen when the first material is between a distal terminal end of the sheath and a distal terminal end of the probe.

Removing the first material from the body lumen can include aspirating the first material from the body lumen.

The method can include removing the second material from the body lumen. Removing the first material from the body lumen can include aspirating the first material from the body lumen. Removing the second material from the body lumen can include aspirating the second material from the body lumen. Removing the first material from the body lumen and removing the second material from the body lumen can include simultaneously aspirating the first material and the second material from the body lumen.

The method can include removing the second material and/or a third material from the body lumen. The third material can be a solution comprising the first material and the second material. The third material can be a mixture of the first material and the second material. The third material can have a different physical property or a different chemical property than the first material and/or the second material. The sheath can have a port. Irrigating the second material into the body lumen can include irrigating the second material into the body lumen through the port. Removing the first material, the second material, and/or the third material from the body lumen can include removing the first material, the second material, and/or the third material from the body lumen through the port. Removing the first material, the second material, and/or the third material from the body lumen can include aspirating the first material, the second material, and/or the third material from the body lumen through the port. The port can be a distal terminal opening of the sheath or an opening on a side of the sheath. The sheath can have an outflow port and an inflow port. Irrigating the second material into the body lumen can include irrigating the second material into the body lumen through the inflow port. Removing the first material, the second material, and/or the third material from the body lumen can include removing the first material, the second material, and/or the third material from the body lumen through the outflow port. Removing the first material, the second material, and/or the third material from the body lumen can include aspirating the first material, the second material, and/or the third material from the body lumen through the outflow port. The sheath can have an inflow channel and an outflow channel. A distal terminal end of the inflow channel can have the inflow port. A distal terminal end of the outflow channel can have the outflow port. The outflow port can be a first distal terminal opening of the sheath and/or a first opening on a side of the sheath. The inflow port can be a second distal terminal opening of the sheath and/or a second opening on a side of the sheath.

The sheath can have a first port. The probe can have a second port. Irrigating the second material into the body lumen can include irrigating the second material into the body lumen through the first port. Removing the first material, the second material, and/or the third material from the body lumen can include removing the first material, the second material, and/or the third material from the body lumen through the second port.

The sheath can have a first port. The probe can have a second port. Irrigating the second material into the body lumen can include irrigating the second material into the body lumen through the second port. Removing the first material, the second material, and/or the third material from the body lumen can include removing the first material, the second material, and/or the third material from the body lumen through the first port.

The probe can have an outflow port and/or an inflow port. Irrigating the second material into the body lumen can include irrigating the second material into the body lumen through the inflow port. Removing the first material, the second material, and/or the third material from the body lumen can include removing the first material, the second material, and/or the third material from the body lumen through the outflow port. Removing the first material, the second material, and/or the third material from the body lumen can include aspirating the first material, the second material, and/or the third material from the body lumen through the outflow port. The probe can have an inflow channel and an outflow channel. A distal terminal end of the inflow channel can have the inflow port. A distal terminal end of the outflow channel can have the outflow port. The outflow port can be a first distal terminal opening of the probe and/or a first opening on a side of the probe. The inflow port can be a second distal terminal opening of the probe and/or a second opening on a side of the probe.

A method of removing a first material from a body lumen is disclosed (e.g., as shown in the drawings and/or as described herein). The method can include inserting a sheath into the body lumen, inserting a probe into the body lumen, agitating the first material in the body lumen with the probe, irrigating a second material into the body lumen, and/or aspirating the first material and the second material from the body lumen.

Agitating the first material in the body lumen with the probe can include moving the probe in the body lumen. Moving the probe in the body lumen can include translating, rotating, and/or vibrating the probe in the body lumen.

Agitating the first material in the body lumen with the probe can include mechanically breaking down the first material with the probe.

The body lumen can be a lumen of a reproductive tract. The body lumen can be a lumen of a vas deferens.

The first material can be an implanted material. The first material can form an occlusion. The first material can be a hydrogel.

The second material can be a dissolving material. The second material can be configured to dissolve another material. The second material can be a sodium bicarbonate solution.

The method can include agitating the second material in the body lumen with the probe.

The method can include advancing the probe out of the sheath and/or retracting the probe into the sheath. The method can include agitating the first material in the body lumen with the probe after advancing the probe out of the sheath. Agitating the first material in the body lumen with the probe can be different from advancing the probe out of the sheath and/or retracting the probe into the sheath. Agitating the first material in the body lumen with the probe can include moving the probe in the body lumen relative to the sheath. The method can include moving the probe in the body lumen relative to the sheath after advancing the probe out of the sheath. Agitating the first material in the body lumen with the probe can include moving the probe in the body lumen relative to the sheath. Moving the probe in the body lumen relative to the sheath can be a different step from advancing the probe out of the sheath and/or retracting the probe into the sheath.

Agitating the first material in the body lumen with the probe can include moving the probe relative to the sheath in the body lumen. Moving the probe relative to the sheath in the body lumen can include translating, dottering, rotating, and/or vibrating the probe in the body lumen.

Agitating the first material in the body lumen with the probe can include mechanically breaking down the first material with the probe.

The lumen can be a lumen of a reproductive tract.

The method can include agitating the second material in the body lumen with the probe.

A method of removing a first material, a second material, and/or a third material from a body lumen is disclosed (e.g., as shown in the drawings and/or as described herein). The method can include inserting a sheath into the body lumen, inserting a probe into the body lumen, agitating the first material in the body lumen with the probe, irrigating the second material into the body lumen, and/or removing the first material, the second material, and/or the third material from the body lumen.

The method can include agitating the second material in the body lumen with the probe.

The method can include agitating the second material and the third material in the body lumen with the probe. Agitating the first material, the second material, and the third material in the body lumen with the probe can include mechanically agitating the first material, second material and the third material in the body lumen with the probe. Agitating the first material, the second material, and the third material in the body lumen with the probe can include moving the probe in the body lumen. Moving the probe in the body lumen can include translating, rotating, and/or vibrating the probe in the body lumen. Moving the probe in the body lumen can include a user and/or a motion source moving the probe. The motion source can be a vibratory motion source, an ultrasonic motion source, a translation motion source, and/or a rotational motion source. Moving the probe in the body lumen can include applying vibratory motion, a dottering motion, an ultrasonic motion, a translational motion, and/or a rotational motion to the probe.

Agitating the first material, the second material, and the third material in the body lumen with the probe can include forming the third material in the body lumen by mixing the first material and the second material together in the body lumen.

Agitating the first material, the second material, and the third material in the body lumen with the probe can include agitating the first material, the second material, and the third material in the body lumen while the probe is in contact with the first material, the second material, and/or the third material. Agitating the first material in the body lumen with the probe can include moving the probe into and out of contact with the first material.

Agitating the first material, the second material, and the third material in the body lumen with the probe can include mixing the first material and the second material together in the body lumen.

Agitating the first material, the second material, and the third material in the body lumen with the probe can include forcing the first material into the second material and/or forcing the second material into the first material.

Agitating the first material, the second material, and the third material in the body lumen with the probe can include mixing the first material into the second material and/or mixing the second material into the first material.

Agitating the first material, the second material, and the third material in the body lumen with the probe can include creating turbulence and/or flow in the second material and/or the third material in the body lumen. The second material can be a first fluid. The third material can be a second fluid. The third material can be a mixture of the first material and the second material and/or can comprise a different material than the first material and/or the second material.

Agitating the first material, the second material, and the third material in the body lumen with the probe can include moving the first material and/or the second material relative to the third material, moving the second material and/or the third material relative to the first material, and/or moving the first material and/or the third material relative to the second material.

Agitating the first material, the second material, and the third material in the body lumen with the probe can include moving the second material and/or the third material toward and/or away from the first material in the body lumen.

Agitating the first material, the second material, and the third material in the body lumen with the probe can include moving the second material and/or the third material while the second material is in contact with the first material in the body lumen. Agitating the first material, the second material, and the third material in the body lumen with the probe can include agitating the second material and/or the third material in the body lumen while the probe is in contact with the second material and/or the third material. Agitating the first material, the second material, and the third material in the body lumen with the probe can include agitating the second material and/or the third material in the body lumen while the probe is in contact with the first material, the second material, and the third material.

The first material can be an implanted material, an implant, and/or a hydrogel. The first material can form an occlusion.

The second material can be configured to dissolve and/or disassociate the first material.

The method can include forming the third material via an interaction between the first material and the second material in the body lumen. The third material can be a solution comprising the first material and the second material. The third material can comprise a mixture of the first material and the second material. The third material can have a different physical property or a different chemical property than the first material and/or the second material.

The method can include irrigating the second material into the body lumen when the first material is distal a distal terminal end of the sheath and/or when the second material is 15.0 cm or less, 10.0 cm or less, or 5.0 cm or less from the distal terminal end of the sheath.

The method can include irrigating the second material into the body lumen when the first material is between a distal terminal end of the sheath and a distal terminal end of the probe.

Removing the first material, the second material, and/or the third material from the body lumen can include aspirating the first material, the second material, and/or the third material from the body lumen.

The sheath can have a port. Irrigating the second material into the body lumen can include irrigating the second material into the body lumen through the port. Removing the first material, the second material, and/or the third material from the body lumen can include removing the first material, the second material, and/or the third material from the body lumen through the port. Removing the first material, the second material, and/or the third material from the body lumen can include aspirating the first material, the second material, and/or the third material from the body lumen through the port. The port can be a distal terminal opening of the sheath and/or an opening on a side of the sheath.

The sheath can have an outflow port and an inflow port. Irrigating the second material into the body lumen can include irrigating the second material into the body lumen through the inflow port. Removing the first material, the second material, and/or the third material from the body lumen can include removing the first material, the second material, and/or the third material from the body lumen through the outflow port. Removing the first material, the second material, and/or the third material from the body lumen can include aspirating the first material, the second material, and/or the third material from the body lumen through the outflow port. The sheath can have an inflow channel and an outflow channel. A distal terminal end of the inflow channel can have the inflow port. A distal terminal end of the outflow channel can have the outflow port. The outflow port can be a first distal terminal opening of the sheath and/or a first opening on a side of the sheath. The inflow port can be a second distal terminal opening of the sheath and/or a second opening on a side of the sheath.

The sheath can have a first port. The probe can have a second port. Irrigating the second material into the body lumen can include irrigating the second material into the body lumen through the first port. Removing the first material, the second material, and/or the third material from the body lumen can include removing the first material, the second material, and/or the third material from the body lumen through the second port.

The sheath can have a first port. The probe can have a second port. Irrigating the second material into the body lumen can include irrigating the second material into the body lumen through the second port. Removing the first material, the second material, and/or the third material from the body lumen can include removing the first material, the second material, and/or the third material from the body lumen through the first port.

The probe can have an outflow port and/or an inflow port. Irrigating the second material into the body lumen can include irrigating the second material into the body lumen through the inflow port. Removing the first material, the second material, and/or the third material from the body lumen can include removing the first material, the second material, and/or the third material from the body lumen through the outflow port. Removing the first material, the second material, and/or the third material from the body lumen can include aspirating the first material, the second material, and/or the third material from the body lumen through the outflow port. The probe can have an inflow channel and an outflow channel. A distal terminal end of the inflow channel can have the inflow port. A distal terminal end of the outflow channel can have the outflow port. The outflow port can be a first distal terminal opening of the probe and/or a first opening on a side of the probe. The inflow port can be a second distal terminal opening of the probe and/or a second opening on a side of the probe.

A device is disclosed (e.g., as shown in the drawings and/or as described herein). The device can have a sheath, a probe, a first material, and/or a first opening. The device can have a first configuration and a second configuration. More of the first material can be distal the first opening when the device is in the second configuration than when the device is in the first configuration. The first material can be closer to a second material when the device is in the second configuration than when the device is in the first configuration. The probe can have a retracted configuration and an advanced configuration. More of the probe can be distal the first opening when the probe is in the advanced configuration than when the probe is in the retracted configuration. When the probe is in the advanced configuration, the probe can be movable from a first position to a second position. When the device is in the second configuration and the probe is in the first position, the probe can be in contact with the first material. When the device is in the second configuration and the probe is in the second position, the probe can be in contact with the first material or a gap can be between the probe and the first material. A distal terminal end of the probe can be the same distance or a different distance from the first opening when the probe is in the second position than when the probe is in the first position.

The first material can be an irrigant.

The sheath can have the first opening.

More of the first material can be in contact with the second material when the device is in the second configuration than when the device is in the first configuration.

The first material can be in contact with the second material when the device is in the second configuration.

Some or none of the first material can be distal the first opening when the device is in the first configuration.

Some or none of the first material can be in contact with the second material when the device is in the first configuration.

More of a distal end of the probe can be inside of the sheath when the probe is in the retracted configuration than when the probe is in the advanced configuration.

When the probe is in the retracted configuration, a first distance can be between the sheath and the distal terminal end of the probe and the first opening. When the probe is in the advanced configuration, a second distance greater than the first distance can be between the distal terminal end of the probe and first opening. The second distance can be 1.0 cm to 15.0 cm greater than the first distance. When the probe is in the advanced configuration, 1.0 cm to 15.0 cm of the probe can be distal the first opening.

When the probe is in the advanced configuration, the probe can be movable from the second position to the first position.

When the probe is in the advanced configuration, the probe can be translatable and/or rotatable from the first position to the second position.

When the probe is in the advanced configuration, the probe can be translatable and/or rotatable back and forth between the first position and the second position.

When the probe is in the advanced configuration, the probe can be configured to oscillate back and forth between the first position and the second position.

When the probe is in the advanced configuration, the distal terminal end of the probe can be 0.01 mm to 5.00 mm farther from the first opening when the probe is in the second position than when the probe is in the first position.

When the probe is in the advanced configuration, the distal terminal end of the probe can be 0.1 mm to 5.0 mm farther from the first opening when the probe is in the second position than when the probe is in the first position.

When the probe is in the advanced configuration, the distal terminal end of the probe can be 0.5 mm to 5.0 mm farther from the first opening when the probe is in the second position than when the probe is in the first position.

When the device is in the second configuration and the probe is in the advanced configuration, the first material can surround the probe. When the device is in the second configuration and the probe is in the advanced configuration, the probe can be surrounded (e.g., circumferentially surrounded) by the first material.

When the device is in the second configuration and the probe is in the first position, the probe can be in contact with the second material.

When the device is in the second configuration and the probe is in the second position, the probe can be in contact with the second material.

The device can have a first material reservoir. The first material reservoir can be filled with the first material. The first material reservoir can have the first material. Less of the first material can be in the first material reservoir when the device is in the second configuration than when the device is in the first configuration. The sheath can have the first material reservoir. The first material reservoir can include a lumen of the sheath (e.g., an inflow lumen of the sheath).

The device can have a first material reservoir. The first material reservoir can be filled with the first material. The first material reservoir can have the first material. When the device is irrigating the first material, the first opening and/or a second opening can be in fluid communication with the first material reservoir. The first opening can be distal the second opening. The sheath can have the first opening and/or the second opening. The sheath can have a lumen. A first end of the lumen can have the first opening. A second end of the lumen can have the second opening.

The device can have a first material reservoir. The first material reservoir can be filled with the first material. The first material reservoir can have the first material. When the device is irrigating the first material, the first opening and/or a second opening can be in fluid communication with the first material reservoir.

The first configuration can be a first deployed configuration of the device and the second configuration can be a second deployed configuration of the device.

The device can have a third configuration. When the device is in the second configuration, the first material distal the first opening can be an irrigated first material. More of the irrigated first material can be proximal the first opening when the device is in the third configuration than when the device is in the second configuration.

The device can have a third configuration. When the device is in the second configuration, the first material distal the first opening can be an irrigated first material. More of the irrigated first material can be in a lumen of the sheath when the device is in the third configuration than when the device is in the second configuration.

The device can have a remover. The first material, second material, and/or a third material can be closer to the first opening when the device is in a third configuration than when the device is in the second configuration. The remover can be an aspirator. The device can have a third configuration. More of the second material and/or a third material can be in a lumen of the sheath when the device is in the third configuration than when the device is in the second configuration.

The first configuration can be a first deployed configuration of the device, the second configuration can be a second deployed configuration of the device, and the third configuration can be a third deployed configuration of the device.

The device can have a first reservoir and a second reservoir. When the device is delivering the first material to a space distal the first opening, the first opening can be in fluid communication with the first material reservoir. When the device is removing the first material, the second material, and/or a third material from the space distal the first opening, a second opening can be in fluid communication with the second reservoir. The sheath can have the first reservoir and/or the second reservoir. The first reservoir can include a first lumen of the sheath (e.g., an inflow lumen of the sheath) and/or the second reservoir can include a second lumen of the sheath (e.g., an outflow lumen sheath).

The device can have a first reservoir and a second reservoir. When the device is delivering the first material to a space distal the first opening, the first opening can be in fluid communication with the first material reservoir. When the device is removing the first material, the second material, and/or a third material from the space distal the first opening, the first opening can be in fluid communication with the second reservoir.

The device can have a mechanical agitation source connected to the probe. The mechanical agitation source can be a vibratory motion source, a dottering motion source, an ultrasonic motion source, a translational motion source, and/or a rotational motion source.

The probe can have a protrusion, a bristle, a brush, an indentation, a coil, a loop, and/or an angulation anywhere on the probe, for example, between a first end of the probe and a second end of the probe.

The probe can have protrusions, bristles, brushes, indentations, coils, loops, and/or angulations anywhere on the probe, for example, between a first end of the probe and a second end of the probe.

The probe can have one or multiple protrusions, one or multiple bristles, one or multiple brushes, one or multiple indentations, one or multiple coils, one or multiple loops, and/or one or multiple angulations anywhere on the probe, for example, between a first end of the probe and the second end of the probe.

The sheath can be a tube. The sheath can be a catheter.

The device can have a remover. The first material, the second material, and/or a third material can be closer to the first opening when the device is in a third configuration than when the device is in the second configuration.

The systems, devices, and/or methods disclosed herein can have any combination of features shown in the drawings and/or described herein (e.g., any combination of features between "A method of removing a first material from a body lumen is disclosed (e.g., as shown in the drawings and/or as described herein)" and "The probe can have one or multiple protrusions, one or multiple bristles, one or multiple brushes, one or multiple indentations, one or multiple coils, one or multiple loops, and/or one or multiple angulations anywhere on the probe, for example, between a first end of the probe and the second end of the probe" above).

A method for performing the delivery and/or removal of occlusion devices from a body space is disclosed (e.g., as shown in the drawings and/or as described herein). The method can include positioning a delivery and/or removal system within the body space. The delivery and/or removal system can have a probe within a penetrating element and a catheter configured to fit on the probe. The catheter can have a catheter lumen and a distal port at the distal end of the catheter lumen. A handle can be attached to the catheter. The method can include advancing the probe within the body space a distance of 1 cm to 15 cm, advancing the catheter over the probe once the translation of the probe reaches 1 cm to 15 cm, and delivering and/or removing an occlusion device within the body space through the catheter.

The body space can be, for example, a reproductive tract, a blood vessel, or a gastrointestinal tract.

The body space can be a body lumen, for example, a lumen of reproductive tract, a lumen of a blood vessel, or a lumen of a gastrointestinal tract.

The distance can be 5.0 cm.

The delivery and/or removal of the occlusion device can occur after the injection of media within the body space.

The delivery and/or removal of the occlusion device can occur after the removal of the probe from the body space.

The delivery and/or removal of the occlusion device can be followed by the injection of media to confirm the presence and/or absence of the occlusion device from the body space.

The advancement of the probe for confirmation of body space access (e.g., intraluminal access) can be a range from 1 cm to 10 cm.

The advancement of the probe for confirmation of body space access (e.g., intraluminal access) can be a range from 5 cm to 10 cm.

A system for performing the delivery and/or removal of occlusion devices from a body space is disclosed (e.g., as shown in the drawings and/or as described herein). The system can have a probe within a penetrating element. The penetrating element can have a needle or a component of a needle. The system can have a catheter configured to fit on the probe and a needle (e.g., a half needle). The catheter can have a catheter lumen and a distal port at the distal end of the catheter lumen. A handle can be attached to the catheter. The advancement of the probe within the body space a predetermined distance can allow for the remaining steps of delivery and/or removal to occur in the body space.

The penetrating element can have a half needle. The penetrating element can be a half needle.

The system can have a half needle. The half needle can be a component of a needle.

The body space can be, for example, a reproductive tract, a blood vessel, or a gastrointestinal tract.

The body space can be a body lumen, for example, a lumen of reproductive tract, a lumen of a blood vessel, or a lumen of a gastrointestinal tract.

The predetermined distance of the probe can be a translation of 5 cm of the probe, for example, relative to the catheter.

The predetermined distance of the probe can be a translation of 1 cm to 15 cm of the probe, for example, relative to the catheter.

A system for performing the removal of occlusion devices from a body space is disclosed (e.g., as shown in the drawings and/or as described herein). The system can have a catheter configured to fit on the probe and a needle or a component of a needle. The catheter can have a catheter lumen and a distal port at the distal end of the catheter lumen. A handle can be attached to the catheter. The system can have a probe with an irrigation source and an aspiration source. The irrigation source can have a dissolution media.

The needle or the component of the needle can be a half needle.

The system can have a half needle. The half needle can be a component of a needle.

The catheter can be configured to fit on the probe and a half needle.

Mechanical agitation can be applied to the probe to remove the occlusive device from the reproductive tract.

The mechanical agitation can include vibratory, dottering, ultrasonic motion, translational motion, and/or rotary motion.

The systems, devices, and/or methods disclosed herein can have any combination of features shown in the drawings and/or described herein (e.g., any combination of features between "A method for performing the delivery and/or removal of occlusion devices from a body space is disclosed (e.g., as shown in the drawings and/or as described herein)" and "The mechanical agitation can include vibratory, dottering, ultrasonic motion, translational motion, and/or rotary motion" above).

Any elements described herein as singular can be pluralized (i.e., anything described as "one" can be more than one). Any species element of a genus element can have the characteristics or elements of any other species element of that genus. The media delivered herein can be any of the fluids (e.g., liquid, gas, or combinations thereof) described herein. The patents and patent applications cited herein are all incorporated by reference herein in their entireties. Some elements may be absent from individual figures for reasons of illustrative clarity. The above-described configurations, elements or complete assemblies and methods and their elements for carrying out the disclosure, and variations of aspects of the disclosure can be combined and modified with each other in any combination. All devices, apparatuses, systems, and methods described herein can be used for medical (e.g., diagnostic, therapeutic or rehabilitative) or non-medical purposes.

Changes and modifications can be made to this disclosure, and equivalents employed, or combinations of any of the disclosed elements, characteristics, features, devices, tools, steps, or methods without departing from the spirit and scope of the disclosure. Any of the disclosed elements, characteristics, features, devices, tools, steps, or methods can be present as a singular or as a plurality regardless of whether the elements, characteristics, features, devices, steps, or methods are explicitly disclosed herein as being singular or as a plurality. Elements shown with any variation are exemplary for the specific variation and can be used on other variations within this disclosure. The terms about and approximately can include the exact values following such terms and can include, for example, a tolerance of plus or minus 1% of any such values, a tolerance of plus or minus 5%, or any other tolerance that one of ordinary skill in the art would understand. Any phrase involving an "A and/or B" construction or similar construction can mean (1) A alone, (2) B alone, (3) A and B together. Any range disclosed can include any subrange of the range disclosed, for example, a range of 1-10 units can include 2-10 units, 8-10 units, or any other subrange. The words "may" and "can" are interchangeable (e.g., "may" can be replaced with "can" and "can" can be replaced with "may"). All systems, devices, and methods described herein can be used for medical (e.g., diagnostic, therapeutic, or rehabilitative) or non-medical purposes. The above-described configurations, elements or complete assemblies and methods and their elements can be combined and modified with each other in any combination.

We claim:

1. A method of confirming intraluminal access of a lumen in a body comprising:
   inserting a sheath into the body;
   advancing a probe relative to the sheath by an advancing distance into the lumen;
   confirming the sheath has access to the lumen if the advancing distance is greater than or equal to a threshold distance;
   agitating a first material in the lumen with the probe;
   irrigating a second material into the lumen; and
   aspirating the first material from the lumen.

2. The method of claim 1, wherein advancing the probe relative to the sheath by the advancing distance into the lumen comprises advancing the probe out of the sheath by the advancing distance.

3. The method of claim 1, wherein confirming the sheath has access to the lumen if the advancing distance is greater than or equal to the threshold distance comprises confirming the sheath is in the lumen if the advancing distance is greater than or equal to the threshold distance.

4. The method of claim 1, wherein inserting the sheath into the body comprises inserting a port into the body, and wherein confirming the sheath has access to the lumen if the advancing distance is greater than or equal to the threshold distance comprises confirming the port has access to the lumen if the advancing distance is greater than or equal to the threshold distance.

5. The method of claim 1, further comprising delivering the first material into the lumen after confirming the sheath has access to the lumen, wherein the first material comprises a hydrogel or is configured to alter a physical property and/or a chemical property of an implant.

6. The method of claim 1, further comprising removing the first material from the lumen after confirming the sheath has access to the lumen, wherein the first material comprises a hydrogel, and wherein the second material is configured to alter a physical property and/or a chemical property of the hydrogel.

7. The method of claim 1, wherein the lumen comprises a lumen of a reproductive tract.

8. The method of claim 1, wherein the first material comprises a hydrogel.

9. The method of claim 1, wherein the second material is configured to physically and/or chemically alter the first material.

10. A method of confirming intraluminal access of a body lumen and removing a first material from the body lumen, the method comprising:
    inserting a sheath into a body having the body lumen;
    advancing a probe relative to the sheath by an advancing distance into the body lumen;
    confirming the sheath has access to the body lumen if the advancing distance is greater than or equal to a threshold distance;
    agitating the first material in the body lumen with the probe;
    irrigating a second material into the body lumen; and
    aspirating the first material and the second material from the body lumen.

11. The method of claim 10, wherein agitating the first material in the body lumen with the probe comprises moving the probe relative to the sheath in the body lumen.

12. The method of claim 11, wherein moving the probe relative to the sheath in the body lumen comprises translating, rotating, and/or vibrating the probe in the body lumen.

13. The method of claim 10, wherein agitating the first material in the body lumen with the probe comprises mechanically breaking down the first material with the probe.

14. The method of claim 10, wherein the lumen comprises a lumen of a reproductive tract.

15. The method of claim 10, further comprising agitating the second material in the body lumen with the probe.

16. A device comprising:
    a sheath; and
    a probe,
    wherein the probe is advanceable from a retracted configuration to an advanced configuration relative to the sheath,
    wherein when the probe is in the retracted configuration, a first distance is between the probe and the sheath,
    wherein when the probe is in the advanced configuration, a second distance greater than the first distance is between the probe and the sheath,
    wherein the first distance is less than a threshold distance, and
    wherein when the second distance is greater than or equal to the threshold distance, the advanced configuration of the probe comprises an indicator to a user that the device has access to a target site.

17. The device of claim 16, wherein when the second distance is greater than or equal to the threshold distance, the advanced configuration of the probe comprises an indicator to a user that the sheath and/or a port has access to the target site.

18. The device of claim 16, wherein the sheath comprises a sheath lumen, and wherein more of the probe is distal the sheath lumen when the probe is in the advanced configuration than when the probe is in the retracted configuration.

19. The device of claim 16, further comprising a material and a material reservoir, wherein a flow path extends between the material reservoir and a distal end of the sheath, wherein the device has a first configuration, a second configuration, and a third configuration, wherein before the second distance becomes greater than or equal to the threshold distance, the device has the first configuration, wherein when the second distance becomes greater than or equal to the threshold distance, the device has the second configuration or the device is changeable from the first configuration to the second configuration, wherein after the second distance becomes greater than or equal to the threshold distance, the device has the third configuration, wherein when the device is in the first configuration, the material is in the material reservoir and the flow path is open or closed, wherein when the device is in the second configuration, the material is between the material reservoir and a distal terminal end of the sheath and the flow path is open or closed, and wherein when the device is in the third configuration, the material is distal a distal terminal end of the sheath and the flow path is open or closed.

20. The device of claim 16, further comprising an irrigator and/or an aspirator, wherein a distal end of the sheath comprises a port, wherein when the irrigator is irrigating, the port is in fluid communication with the irrigator, and wherein when the aspirator is aspirating, the port is in fluid communication with the aspirator.

* * * * *